US012790366B2

(12) United States Patent
Micalizio

(10) Patent No.: US 12,790,366 B2
(45) Date of Patent: Nov. 10, 2026

(54) METHODS FOR TREATING A DISEASE OR CONDITION OF TETRACYCLIC COMPOUNDS WITH STEREOSELECTIVE C9-C10 BOND FORMATION

(71) Applicant: Trustees of Dartmouth College, Hanover, NH (US)

(72) Inventor: Glenn C. Micalizio, Norwich, VT (US)

(73) Assignee: Trustees of Dartmouth College, Hanover, NH (US)

(*) Notice: Subject to any disclaimer, the term of this patent is extended or adjusted under 35 U.S.C. 154(b) by 266 days.

(21) Appl. No.: 18/799,216

(22) Filed: Aug. 9, 2024

(65) Prior Publication Data

US 2024/0400607 A1 Dec. 5, 2024

Related U.S. Application Data

(60) Continuation of application No. 18/050,730, filed on Oct. 28, 2022, now Pat. No. 12,065,465, which is a division of application No. 17/191,281, filed on Mar. 3, 2021, now Pat. No. 11,512,107, which is a continuation-in-part of application No. PCT/US2019/049743, filed on Sep. 5, 2019.

(60) Provisional application No. 62/985,109, filed on Mar. 4, 2020, provisional application No. 62/833,291, filed on Apr. 12, 2019, provisional application No. 62/829,722, filed on Apr. 5, 2019, provisional application No. 62/728,163, filed on Sep. 7, 2018.

(51) Int. Cl.
*C07J 75/00* (2006.01)
*C07J 1/00* (2006.01)

(52) U.S. Cl.
CPC ........... *C07J 75/005* (2013.01); *C07J 1/0055* (2013.01)

(58) Field of Classification Search
CPC .............................. C07J 75/005; C07J 1/0055
See application file for complete search history.

(56) References Cited

U.S. PATENT DOCUMENTS

| | | | | |
|---|---|---|---|---|
| 5,464,866 | A | 11/1995 | Clark et al. | |
| 6,054,447 | A | 4/2000 | Levine et al. | |
| 6,072,062 | A | 6/2000 | Valles et al. | |
| 7,618,999 | B2 | 11/2009 | Guillan et al. | |
| 2006/0027084 | A1 | 2/2006 | Schneider | |
| 2008/0002723 | A1 | 1/2008 | Ng et al. | |
| 2020/0199171 | A1* | 6/2020 | Micalizio | A61P 25/00 |

FOREIGN PATENT DOCUMENTS

| | | | |
|---|---|---|---|
| CA | 2359660 | A1 | 8/2000 |
| CN | 1346364 | A | 4/2002 |
| GB | 560812 | A | 4/1944 |
| WO | 2020051329 | A1 | 3/2020 |

OTHER PUBLICATIONS

Petit et al., 21 Neuropsychopharmacol. 211-215 (2011) (Year: 2011).*
Kim et al., Nat. Chem., 10(1): 70-77 (2018).
Kim et al., Nature Communications, 10(1): 1-10 (2019).
O'Rourke et al., Tetrahedron, 72(45): 7093-7123 (2016).
The United States Patent and Trademark Office, International Search Report and Written Opinion in International Application No. PCT/US2019/049743 (Nov. 13, 2019).
Corey et al, J. Am. Chem. Soc., 121, 710-714, 1999.
Greszler et al, J. Am. Chem. Soc., 134, 2766-2774, 2012.
Greszler et al, J. Am. Chem. Soc., 134, supporting information, 2012.
Hanada et al, Chem. Pharm. Bull., 51(1), 104-106, 2003.
Kurosawa et al, Chem. Pharm. Bull., 26(5), 1533-1539, 1978.
Tietze et al., J. Am. Chem. Soc., 120, 8971-8977, 1998.

* cited by examiner

*Primary Examiner* — Timothy R Rozof
(74) *Attorney, Agent, or Firm* — Neal, Gerber & Eisenberg LLP

(57) ABSTRACT

The present disclosure relates to stereodefined polycyclic (e.g., tetracyclic) compounds that contain quaternary centers at one or multiple ring fusions, synthetic methods for preparing such compounds, and methods of using such compounds to treat a disease, such as a brain tumor and, particularly, a glioma.

16 Claims, 10 Drawing Sheets

U251

U87

METHODS FOR TREATING A DISEASE OR CONDITION OF TETRACYCLIC COMPOUNDS WITH STEREOSELECTIVE C9-C10 BOND FORMATION

CROSS REFERENCE TO RELATED APPLICATIONS

This patent application is a continuation application of U.S. patent application Ser. No. 18/050,730, filed on Oct. 28, 2022 as a divisional application of U.S. patent application Ser. No. 17/191,281, now U.S. Pat. No. 11,512,107, filed on Mar. 3, 2021 as a continuation-in-part of International Patent Application No. PCT/US2019/049743, filed on Sep. 5, 2019, which claims priority to U.S. Provisional Patent Application No. 62/728,163, filed on Sep. 7, 2018, to U.S. Provisional Patent Application No. 62/829,722, filed on Apr. 5, 2019, and to U.S. Provisional Patent Application No. 62/833,291, filed on Apr. 12, 2019. This patent application also claims priority to U.S. Provisional Patent Application No. 62/985,109, filed on Mar. 4, 2020. Each of the above-mentioned applications are fully incorporated herein by reference.

FEDERALLY SPONSORED RESEARCH OR DEVELOPMENT

This invention was made with government support under R01 GM080266 awarded by the National Institutes of Health. The government has certain rights in the invention.

FIELD OF THE INVENTION

The present disclosure provides concise synthetic methods for accessing stereodefined carbocycles that contain quaternary centers at one or multiple ring fusions, compounds accessible by such synthetic methods, and methods of using such compounds to treat a disease, such as a brain tumor and, particularly, a glioma.

BACKGROUND OF THE INVENTION

Steroids and tetracyclic terpenoids (more broadly), including unnatural variants, have had a transformative impact on medicine and society, playing vital roles as oral contraceptives, treatments for cancer (including anti-angiogenic agents), heart failure, inflammation, pain, and traumatic brain injuries, among others, and natural molecules in this class have served as important chemical precursors in drug discovery and development. Despite this rich history, substantial barriers persist that greatly limit the types of synthetic compositions of matter in this broad area of chemical space that can efficiently be prepared and explored as potential medicines and biological tools/probes.

Presently available synthetic and semisynthetic routes to molecules in this class are often complex, inefficient, and/or wholly incapable of producing advantageous collections (i.e., libraries) of highly oxygenated/functionalized target compositions necessary for advancement through modern drug development. Indeed, efficient de novo synthesis of "steroidal" systems, or tetracyclic terpenoid-inspired compositions of matter, remains a challenging problem in chemistry.

All of the more than 100 FDA-approved drugs in this area of chemical space are of the natural enantiomer (specific reference being made to the absolute stereochemistry at C13 of the steroidal skeleton)—a fact that is certainly influenced by the manner in which such compounds are prepared. In fact, it is typical that medicinal agents in this class are synthesized from naturally occurring steroids. As compared to steroidal compositions of matter that have the natural absolute stereochemistry at C13 ("nat-steroids"), synthetic ent-steroidal compounds (defined by an unnatural absolute stereochemistry) have complementary three-dimensional structures while offering similar "drug-like" physical properties. As a result, synthetic ent-steroids are privileged natural product-inspired scaffolds of great potential therapeutic relevance, and are distinct compositions in comparison to their natural isomers. (See, Akwa, Y., et al., Proc. Natl. Acad. Sci. U.S.A., 98, 14033-14037 [2001]; Green, P. S., et al., Endocrinology, 142, 400-406 [2001]; Biellmann, J. F., Chem. Rev., 103, 2019-2033 [2003]; Covey, D. F., Steroids, 74 (7): 577-585 [2009]; and Petit, G. H., et al., Eur. Neuropsychopharmacol., 21, 211-215 [2011]). However, investigations of the unnatural enantiomers of steroid-inspired compounds have been hampered in the past due to the great difficulty associated with preparing/accessing such compositions of matter. While semisynthetic routes to nat-steroids (i.e., those beginning with a readily available steroid or related natural product) have been incredibly powerful, such preparative methods are not suitable for producing non-naturally occurring ent-steroids because the starting material possesses a mirror image backbone inherent to natural molecules in the class. In summary, ent-steroids are an important class of privileged pharmaceutical drug-like molecules that presently cannot be fully leveraged in biological and pharmaceutical research efforts because these molecules are not readily available from natural sources and existing chemical synthesis pathways are inefficient and not flexible enough to produce diverse collections of such molecules suitable for drug discovery and development.

A practical method for efficient and stereospecific production of ent-steroids, as well as other unnatural stereoisomers and simply unique compositions of matter within the broad class of tetracyclic terpenoids, would enable scientists and physicians to better exploit the as yet untapped potential of new molecules within this pharmaceutically-privileged class (including ent-steroids) as useful tools and therapeutics. In fact, even within the nat-steroid family of potential medicines, the current state-of-the-art that relies heavily on semisynthesis (where synthesis proceeds from a readily available natural product) comes with significant limitations based on the structure of the abundant and readily available natural material (e.g., level of unsaturation, density of oxygenation, and degree of substitution of the starting material). As such, even with state-of-the-art approaches, vast regions of privileged chemical space for medicinal science remain difficult to explore. Accordingly, what is needed are efficient and step-economical (i.e., concise), flexible, convergent, and enantiospecific methods of synthesizing synthetic nat- and/or ent-steroids having varying stereochemistry and substitution, and/or functionality that facilitates subsequent molecular perturbation processes (i.e., manipulation of functionality in each ring of the characteristic tetracyclic nucleus) at research and/or production scale.

One example of a target for steroid and steroid-like compounds are estrogen receptors (ERα and ERβ), both of which can play roles in cancer.

Gliomas (Grade I-IV) are lethal primary brain tumors that make up eighty percent of all malignant brain tumors and about thirty percent of all central nervous system tumors. Low-grade gliomas (grade I & II) increase in time to become high-grade gliomas (Grade III & IV). These recur in more than 90% of cases and have a median survival rate of 14 months and a 5-year survival rate of less than 10%. They harbor diverse oncogenes and mutated tumor-suppressor genes whose pattern of alteration and expression vary considerably from tumor to tumor.

Most gliomas, however, express elevated levels of a particular estrogen receptor (ER) subtype, ERβ. Two subtypes of estrogen receptors, ERα and ERβ, have been identified. In spite of their significant sequence homology, there are notable differences in distribution and function of these receptors: ERα is predominantly expressed in bone, breast, prostate (stroma), uterus, ovary (thecal cells) and brain, whereas ERβ is usually present in ovary (granulose cells), bladder, colon, immune, cardiovascular and nervous systems. ERα activation is responsible for the classic function of estrogen, including uterine stimulation. ERβ activation may have anti-proliferative effects, including in many cancer types. Indeed, ERβ is an established tumor suppressor in several cancers; higher expression of ERβ is correlated to a better prognosis, and ERβ agonists induce apoptosis. Nevertheless, despite the tumor suppressive role of ERβ, 17β-estradiol (a potent but unselective agonist of ERα and ERβ) is not used as a therapy against gliomas as long-term treatment because it can result in cancers of the female reproductive system and prostate cancer in men. Thus, a selective ERβ agonist may be able to suppress cancer cell proliferation without stimulating the uterus.

However, the two subtypes of estrogen receptors are almost identical, with only two residues differing in the ligand binding pockets. Therefore, there is a significant challenge in obtaining subtype-selective ligands. For example, erteberel is a non-steroidal ERβ agonist that has been investigated and/or considered for the treatment of schizophrenia, benign prostatic hyperplasia, and glioblastoma. Erteberel has 14-fold binding selectivity for ERβ over ERα (Ki=0.19 nM versus 2.68 nM, respectively) and 32-fold functional selectivity for activation of ERβ over ERα ($EC_{50}$=0.66 nM versus 19.4 nM, respectively). However, erteberel's profile is insufficient for in vivo selectivity, being well recognized as an agonist of both ERβ and ERα in vivo and, consequently, has been described as producing effects such as suppression of gonadal testosterone production in men. Accordingly, what is needed are new highly selective ERβ agonists. Indeed, there is a dire need for novel drugs that selectively target ERβ, and in particular highly selective ERβ agonists, to, for example, treat gliomas (among other cancers).

SUMMARY OF THE INVENTION

The present disclosure relates to methods for producing stereodefined polycyclic ring compounds, including enantiodefined systems, through unique intermediates, synthesis strategies, and chemical reactions. More particularly, the present disclosure provides synthetic methods for producing a natural product-inspired complex polycyclic tetracycle, including, but not limited to, a compound having a "C19 steroidal scaffold." As used herein, the term "C19 steroidal scaffold" includes not only steroids, and compounds that could be defined as steroidal, that have 19 carbon atoms, but also includes compounds having additional carbon atoms, including, but not limited to C20, C21, C22, C23, C24, C25, C26, C27, C28, C29, C30, or C31 compounds. In certain embodiments, the methods involve a stereoselective intramolecular formation of the C9-C10 bond (for example, with a Friedel-Crafts alkylation, a Heck reaction, or a radical cyclization). In certain embodiments, the methods involve a stereospecific oxidative dearomatization that occurs with 1,2-migration (from the steroidal C9 carbon to the steroidal C10 carbon).

In particular, the present disclosure relates to a concise approach to the assembly of fused carbocyclic structures through a novel sequence of chemical transformations that includes a stereoselective intramolecular Heck reaction to forge the "steroidal" C9-C10 bond, establishing a quaternary center at C9.

The present disclosure also relates to steroidal compounds, including molecules with natural ("nat-") absolute stereochemistry and compounds with unnatural ("ent-") absolute stereochemistry, as well as synthetic variants based on such skeletons. In certain embodiments, the compounds have a C19 steroidal scaffold. In other embodiments, compounds having a C19 steroidal scaffold enable access to further compounds based on, or derived from, the C19 scaffold, such as non-natural antipodes of synthetic agents related to natural terpenoids (i.e., steroids, limonoids, bufadienolides, etc.). In certain embodiments, the compounds are synthetic C9-α and C9-β-alkyl as well as C10-α and C10-β-alkyl steroidal tetracycles.

The present disclosure also relates to the use of such compounds as biologically active (e.g., therapeutic) components in, for example, pharmaceutical compositions and/or directly as human and/or animal therapeutics and medicines. In certain embodiments, the compounds are ERβ selective agonists and/or may be used to treat or prevent conditions, disorders, or diseases such as cancer (e.g., breast cancer, prostate cancer, ovarian cancer, acute myeloid leukemia, and glioma, among others) or neurodegeneration. Currently there is no widely applicable cure for primary brain tumors. The compounds disclosed herein (e.g., Compounds 100 and 101) are potent and highly selective agonists of the Estrogen Receptor beta (ERβ) that inhibit growth of human glioblastoma cell lines as well as primary glioma tumor cells from patients.

In one aspect, this disclosure provides a method for treating a brain tumor by administering a compound disclosed herein or a pharmaceutically acceptable salt or prodrug thereof to a patient in need thereof. In some embodiments, the compound is Compound 100. In some embodiments, the compound is Compound 101. In some embodiments, the brain tumor is a glioma. In some embodiments, the compound is administered orally.

The compounds, pharmaceutical compositions comprising the compounds, and methods for treating or preventing conditions, disorders, or diseases by administering the compounds are further described herein.

These and other objects of the invention are described in the following paragraphs. These objects should not be deemed to narrow the scope of the invention.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art.

DESCRIPTION OF THE INVENTION

Figure 1:
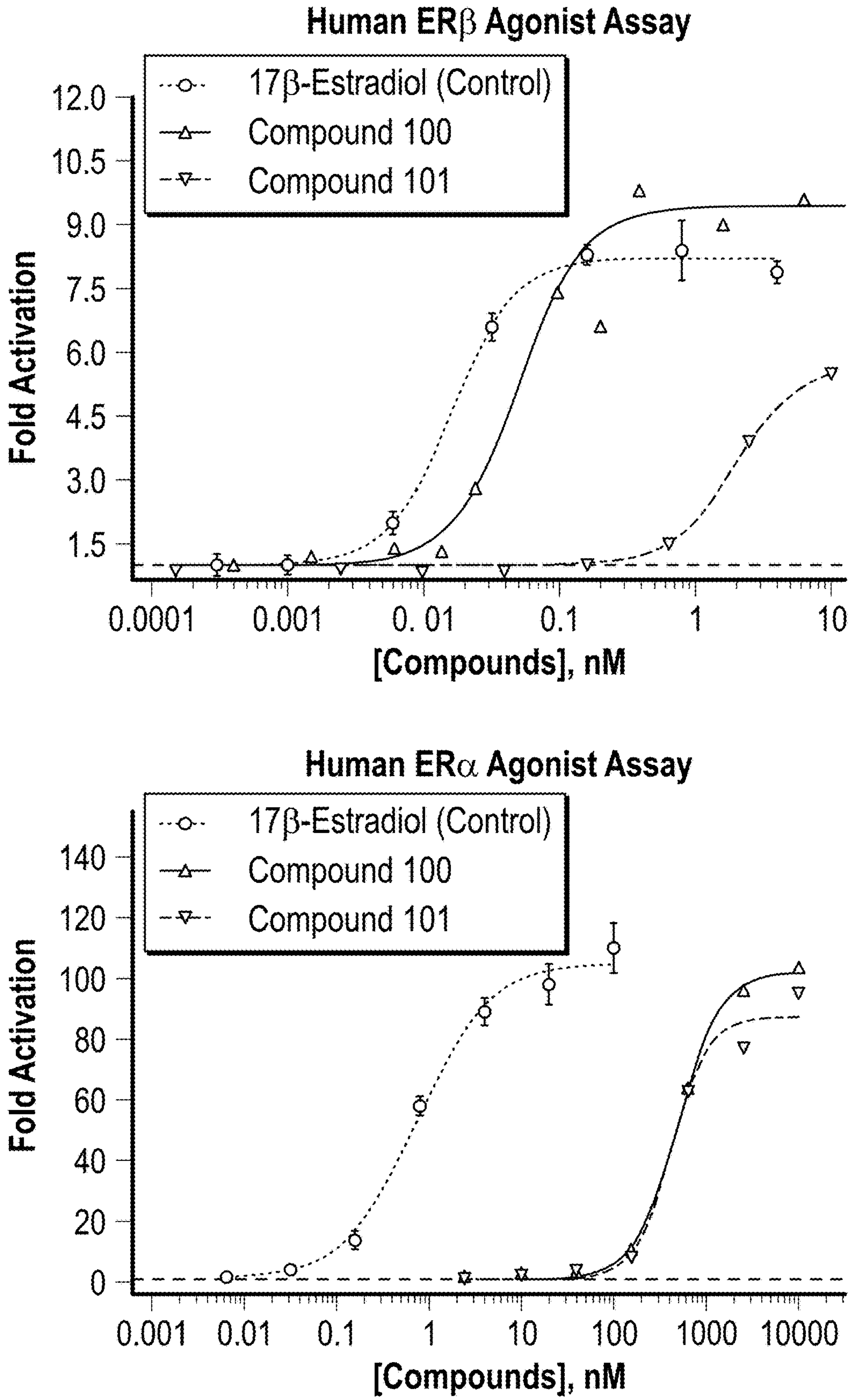
FIG. 1 is a set of line graphs showing the results of ERβ and ERα agonist assays for Compounds 100 and 101.

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

In certain aspects, the present disclosure relates to compounds (and methods of making such compounds, compositions comprising such compounds, and methods of using such compounds) comprising a generic tetracyclic steroidal (A, B, C, D) ring structure, as follows:

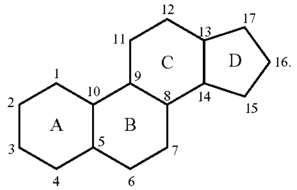

More particularly, the present disclosure relates to compounds (and methods of making such compounds, compositions comprising such compounds, and methods of using such compounds) comprising a generic C19 steroidal core skeleton of Formula (I) or Formula (II), where additional substitution about these base structures is intended to be within the scope of the invention:

(I)

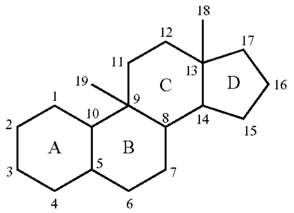

(II)

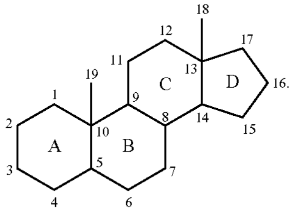

In one aspect, this disclosure provides a composition comprising a collection of synthetic stereoisomers having a chemical structure including a C19 steroidal core skeleton of Formula (I), said C19 steroidal core skeleton having a quaternary center at each of carbon C9 and carbon C13, including stereoisomeric variation among the collection of synthetic stereoisomers; wherein the composition comprises greater than about 70%, alternatively greater than about 75%, alternatively greater than about 80%, alternatively greater than about 85%, alternatively greater than about 90%, or alternatively greater than about 95% of a single C9/C13 stereoisomer relative to other C9/C13 stereoisomers.

In certain embodiments, the single C9/C13 stereoisomer is a diastereomer of a natural compound. In certain embodiments, the single C9/C13 stereoisomer is an enantiomer of a natural compound.

In certain embodiments, the single C9/C13 stereoisomer has a chemical structure including Formula (I-1.1), Formula (I-1.2), Formula (I-1.3), or Formula (I-1.4):

(I-1.1)

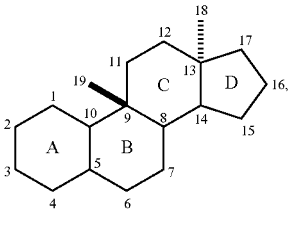

(I-1.2)

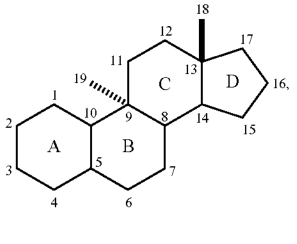

-continued (I-1.3)

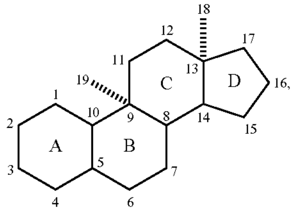

or (I-1.4)

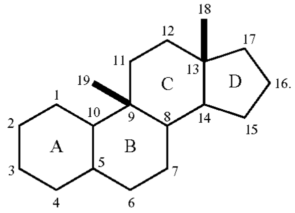

The C19 steroidal core skeleton depicted above in Formula (I-1.1), Formula (I-1.2), Formula (I-1.3), or Formula (I-1.4) encompasses, inter alia, a steroidal core skeleton, such as Formula (I-2.1), Formula (I-2.2), Formula (I-2.3), or Formula (I-2.4):

(I-2.1)

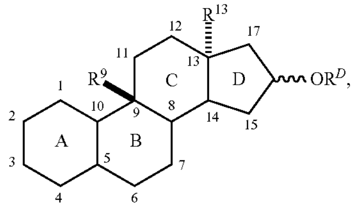

(I-2.2)

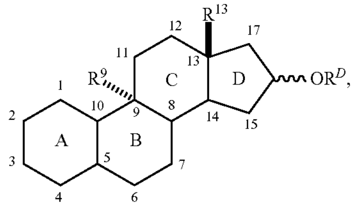

(I-2.3)

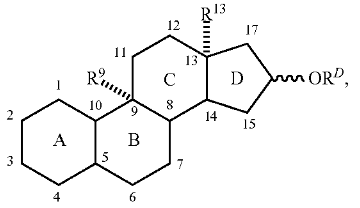

or (I-2.4)

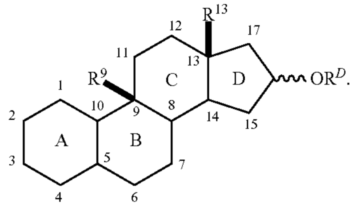

In another aspect, this disclosure provides a composition comprising a collection of synthetic stereoisomers having a chemical structure including a C19 steroidal core skeleton of Formula (II), said C19 steroidal core skeleton having a quaternary center at each of carbon C10 and carbon C13, including stereoisomeric variation among the collection of synthetic stereoisomers; wherein the composition comprises greater than about 70%, alternatively greater than about 75%, alternatively greater than about 80%, alternatively greater than about 85%, alternatively greater than about 90%, or alternatively greater than about 95% of a single C10/C13 stereoisomer relative to other C10/C13 stereoisomers.

In certain embodiments, the single C10/C13 stereoisomer is a diastereomer of a natural compound. In certain embodiments, the single C10/C13 stereoisomer is an enantiomer of a natural compound.

In certain embodiments, the single C10/C13 stereoisomer has a chemical structure including Formula (II-1.1), Formula (II-1.2), Formula (II-1.3), or Formula (II-1.4):

(II-1.1)

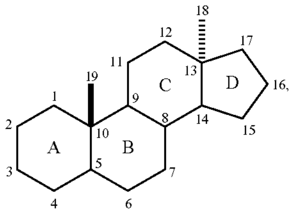

(II-1.2)

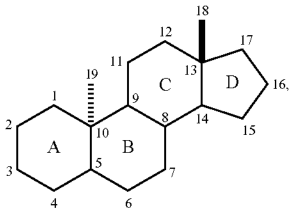

(II-1.3)

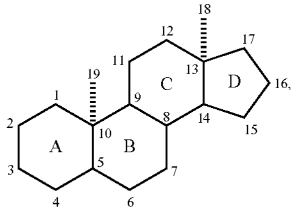

or (II-1.4)

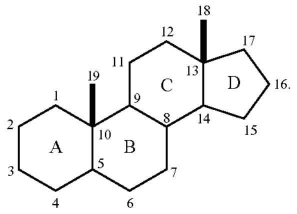

The C19 steroidal core skeleton depicted above in Formula (II-1.1), Formula (II-1.2), Formula (II-1.3), or Formula (II-1.4) encompasses, inter alia, a steroidal core skeleton, such as Formula (II-2.1), Formula (II-2.2), Formula (II-2.3), or Formula (II-2.4):

(II-2.1)

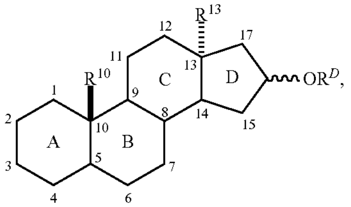

(II-2.2)

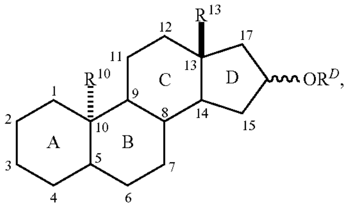

(II-2.3)

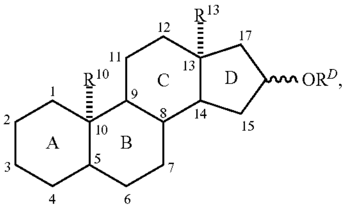

or (II-2.4)

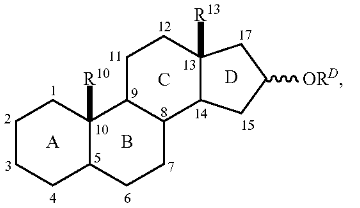

The C19 steroidal core skeletons depicted above encompasses, inter alia, a C20 steroidal core skeleton, such as:

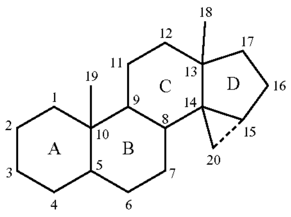

or

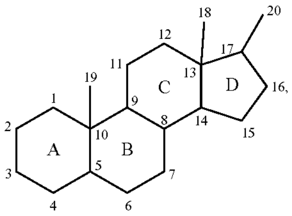

where the dashed bond between C15 and C20 represents an optional bond forming a fused cyclopropane.

The numbering convention throughout the present disclosure is in accordance with numbered structures above.

In reference to the generic tetracyclic steroidal (A, B, C, D) ring structure and the generic C19 and C20 steroidal core skeletons, it will be well appreciated that in view of the disclosure contained herein as well as the teachings in the relevant fields of art, the compounds, compositions, and methods of the present disclosure are not limited to any particular respective constituent (R) group(s) at the various numbered carbon atoms. For example, an R group may be hydrogen, a $C_{1-10}$-aliphatic group, a $C_{6-10}$ aromatic group, carboxylic acid, carboxylic acid ester, hydroxyl, or halogen. Moreover, it will be well appreciated that in view of the disclosure contained herein as well as the teachings in the relevant fields of art, the compounds, compositions, and methods of the present disclosure may comprise ones in which the A ring can be saturated, partially unsaturated, or completely unsaturated (i.e., aromatic); likewise, the B ring can be saturated, partially unsaturated, or completely unsaturated.

In an exemplary embodiment, with reference to Formula (I-2.1), Formula (I-2.2), Formula (I-2.3), or Formula (I-2.4), each of C1, C2, C3, C4, C6, C7, C10, C11, C12, C14, and C17 is independently substituted with hydrogen, $C_{1-10}$-alkyl, $C_{2-10}$-alkenyl, $C_{2-10}$-alkynyl, $C_{1-10}$-haloalkyl, halogen, oxo, hydroxy, $C_{1-6}$-alkoxy, —O—$C_{1-10}$-alkyl, —O—$C_{2-10}$-alkenyl, —O—$C_{2-10}$-alkynyl, —O—$C_{1-10}$-haloalkyl, —O—$C_{6-10}$-aryl, —O-5- to 10-membered heteroaryl, —O—C(O)—$C_{1-10}$-alkyl, —O—C(O)—$C_{6-10}$-aryl, —O—C(O)-5- to 10-membered heteroaryl, $C_{6-10}$-aryl, or 5- to 10-membered heteroaryl and $R^9$, $R^{13}$, and $R^D$ are defined herein.

In an exemplary embodiment, with reference to Formula (II-2.1), Formula (II-2.2), Formula (II-2.3), or Formula (II-2.4), each of $C_1$, C2, C3, C4, C6, C7, C9, C11, C12, C14, and C17 is independently substituted with hydrogen, $C_{1-10}$-alkyl, $C_{2-10}$-alkenyl, $C_{2-10}$-alkynyl, $C_{1-10}$-haloalkyl, halogen, oxo, hydroxy, $C_{1-6}$-alkoxy, —O—$C_{1-10}$-alkyl, —O—$C_{2-10}$-alkenyl, —O—$C_{2-10}$-alkynyl, —O—$C_{1-10}$-haloalkyl, —O—$C_{6-10}$-aryl, —O-5- to 10-membered heteroaryl, —O—C(O)—$C_{1-10}$-alkyl, —O—C(O)—$C_{6-10}$-aryl, —O—C(O)-5- to 10-membered heteroaryl, $C_{6-10}$-aryl, or 5- to 10-membered heteroaryl and $R^{10}$, $R^{13}$, and $R^D$ are defined herein.

A. DEFINITIONS

As used in the specification and the appended claims, unless specified to the contrary, the following terms have the meaning indicated:

The term "about" as used herein, means approximately, and in most cases within 10% of the stated value.

The term "aliphatic" as used herein, includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups. In some embodiments, one or more units (e.g., methylene units) of an aliphatic may be replaced with —O—, —$NR^x$—, —C(O)—, or —$S(O)_n$—, where $R^x$ is hydrogen or $C_{1-6}$-alkyl and n is 0, 1, or 2. As will be appreciated by one of ordinary skill in the art, "aliphatic" is intended herein to include alkyl, alkenyl, alkynyl, cycloalkyl, and cycloalkenyl moieties.

The term "brain tumor" includes a glioma, such as an astrocytoma, glioblastoma, ependymoma (e.g., anaplastic ependymoma or myxopapillary ependymoma), oligodendroglioma (e.g., anaplastic oligodendroglioma or anaplastic oligoastrocytoma), and all gliomas classified under WHO Grade 1 to Grade 4.

The term "pharmaceutically acceptable" is used adjectivally to mean that the modified noun is appropriate for use as a pharmaceutical product for human use or as a part of a pharmaceutical product for human use.

The term "prodrug" refers to a compound that can be readily converted (e.g., metabolized) in vivo to yield a parent compound. Prodrugs include, but are not limited to, compounds having a substituent, such an ester moiety, attached to a hydroxy group at C3 (steroid numbering), which yield a parent compound having a phenolic A ring upon in vivo conversion. Suitable C3 substituents are identified in US2007/0015740 A1, which is herein incorporated by reference in its entirety. Exemplary ester moieties include, but are not limited to, an alkyl ester (e.g., —O—$C_{1-6}$-alkyl), a carbonate ester (e.g., —O—C(O)—O—$C_{1-10}$-alkyl), a carbamate ester (e.g., —O—C(O)—$NR^{Z1}R^{Z2}$), and a sulfamate ester (e.g., —O—$S(O)_2NR^{Z1}R^{Z2}$). Additionally or alternatively, prodrugs may have a substituent, such as an optionally substituted 5- to 10-membered heteroaryl, attached to carbon C17 (steroid numbering), such as those identified in US2014/0371181 A1, which is herein incorporated by reference in its entirety. Prodrugs also include, but are not limited to, di-steroidal prodrugs such as those disclosed in U.S. Pat. No. 7,067,505, which is herein incorporated by reference in its entirety.

The terms "treat", "treating" and "treatment" refer to a method of alleviating or abrogating a condition, disorder, or disease and/or the attendant symptoms thereof.

B. SYNTHETIC METHODS AND INTERMEDIATE COMPOUNDS

In one aspect, the present disclosure provides: (1) a stereoselective intramolecular reaction to forge the steroidal C9-C10 bond (for example, by Friedel-Crafts reaction, Heck reaction, or radical cyclization) and/or (2) an oxidative dearomatization reaction that is terminated by a suprafacial 1,2-shift, in some cases also including loss of a proton, to deliver a fused polycyclic system containing a quaternary center at the ring fusion (at the steroidal C10 carbon). In certain embodiments, the present disclosure provides synthetic methods that allow for the enantiospecific construction of a C19 steroidal core skeleton, preferably from an inexpensive, commercially available starting material, such as epichlorohydrin. In certain embodiments, the present disclosure provides synthetic methods that enable access to non-natural antipodes of synthetic agents related to natural terpenoids (i.e., steroids, limonoids, bufadienolides, etc.).

In one aspect, the present disclosure provides a method for manufacturing a tetracyclic compound. In certain embodiments, the method comprises a step of converting an unsaturated hydrindane to a steroidal tetracycle by intramolecular formation of the C9-C10 bond (for example, by Friedel-Crafts, Heck, or radical cyclization reaction). In some such embodiments, the converting step is carried out in the presence of a chiral catalyst or reagent. In certain embodiments, the method comprises shifting a substituent of a steroidal tetracycle from C9 to C10.

In one aspect, the present disclosure provides a method for converting an unsaturated hydrindane to a steroidal tetracycle. In certain embodiments, the unsaturated hydrindane has a structure corresponding to:

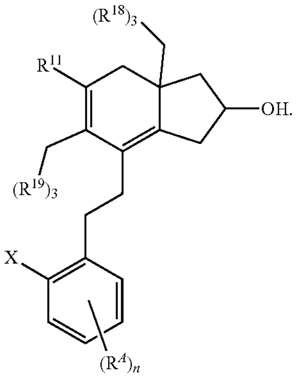

In certain embodiments, the unsaturated hydrindane is converted to the steroid tetracycle by a Heck reaction or radical cyclization. In some such embodiments, the unsaturated hydrindane is converted to the steroid tetracycle by a Heck reaction. Double asymmetric Friedel-Crafts cyclization proved most effective for establishing anti-relative stereochemistry (with respect to C13), while an intramolecular Heck reaction reliably delivered the syn-diastereomers with high selectivity.

In one aspect, the present disclosure provides a method for converting a hydrindane to a steroidal tetracycle via a Heck reaction. As used herein, the term "Heck reaction" includes a standard Heck reaction or a reductive Heck reaction mediated by palladium as well as other metals known to those of skill in the art. The present disclosure demonstrates that ring closure that proceeds by Heck reaction (as opposed to the Friedel-Crafts-based approach) has proven to be both site-selective and stereoselective. Indeed, the major stereoisomer obtained from the Heck reaction is the opposite of what is expected from the Friedel-Crafts-based approach. Moreover, the product contains "C-ring" functionality of potential broad relevance due to the host of functional group manipulations that are available for transforming alkenes into other motifs (e.g., dihydroxylation, epoxidation, hydroboration, etc.).

As disclosed herein, use of an intramolecular Heck cyclization to forge the C9-C10 bond is highly stereoselective for the production of the otherwise elusive C9/C13 syn-stereoisomers. In certain embodiments, the use of the intramolecular Heck cyclization to forge the C9-C10 bond, also delivers products bearing unsaturation at steroidal carbons C11 and C12.

In certain embodiments, the method further comprises an oxidative rearrangement reaction where the C9 substituent can be migrated to C10 in a suprafacial manner.

The following general scheme is representative of a particular embodiment of the method:

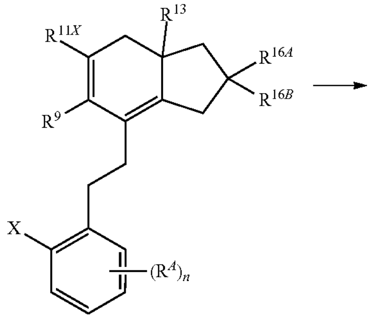

-continued

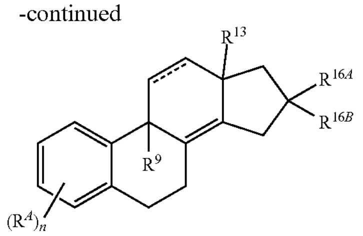

wherein X is a group suitable for a Heck reaction, such as halogen or trifluoromethanesulfonate (—OTf) and $R^{11X}$ is hydrogen or an organosilicon substituent such as trimethylsilyl (TMS), or alternatively an organotin or organogermanium substituent. $R^A$, $R^9$, $R^{13}$, $R^{16A}$, and $R^{16B}$ may be any substituent described herein. In certain embodiments, X is —OTf. In certain embodiments, $R^{11X}$ is TMS. In certain embodiments, one of $R^{16A}$ and $R^{16B}$ is —$OR^D$ and the other is hydrogen.

In another aspect, the present disclosure provides a method for converting a silyl-substituted hydrindane to a steroidal tetracycle. The following general scheme is representative of a particular embodiment of the method:

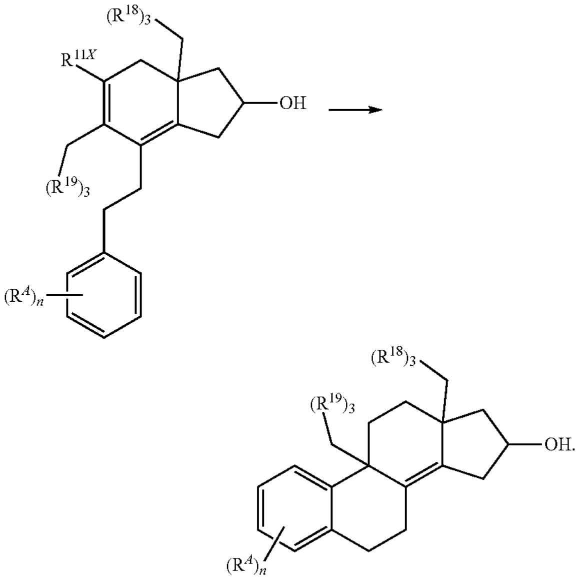

In certain embodiments, $R^{11X}$ represents an organosilicon, or alternatively an organotin or organogermanium, substituent. In certain embodiments, $R^{11X}$ is —$Si(R^M)_3$.

In certain embodiments, a tandem acid-mediated reaction is employed to induce protodesilylation at C11 (steroid numbering) and initiate a site- and stereoselective intramolecular Friedel-Crafts alkylation to generate the steroidal tetracycle. It is understood that substitution at C6 or C7 may be tolerated, if not preferred, not only for varying the biological profile of the molecules produced, but also for controlling the stereoselectivity of the ring-forming event.

In certain embodiments, the method is carried out in the presence of a catalyst or reagent, such as a Brønstead or Lewis acid. Examples of catalysts include one or more halides (e.g., chlorides, bromides, fluorides or iodides) of a transition metal (e.g., iron, aluminum, antimony, tin, or titanium). Specific examples of catalysts include, but are not limited to, $SbCl_5$, $SnCl_4$, and $TiCl_4$, and these may be used in the presence of a proton source like an alcohol or phenol.

In certain embodiments, the catalyst or reagent is a chiral catalyst or reagent. In some such embodiments, the chiral catalyst or reagent is 1,1'-Bi-2-naphthol (Binol) or a Binol derivative. In some such embodiments, the chiral catalyst or reagent is (R)-Binol or (S)-Binol, used in combination with a Lewis acid including $SnCl_4$.

Use of one enantiomer of Binol as the chiral catalyst or reagent may bias the reaction to favor a particular enantiomeric or diastereomeric tetracycle. For example, when (R)-Binol is employed with a particular enantiomer of the hydrindane starting material, as in Example 1-1, the reaction proceeds to deliver the Steroid 4 with very high levels of diastereoselection (≥20:1).

In certain embodiments, the stereoselectivity of the method is tuned by utilizing a single enantiomer of a chiral catalyst or reagent, and/or protecting/removing free hydroxy groups present in the cyclization substrate.

In certain embodiments, the method (e.g., including an appropriate cyclization step as described herein) produces a stereoisomer with high selectivity (i.e., dr>10:1 and even >20:1). In some such embodiments, the method produces a composition having at least 80%, at least 85%, at least 90%, at least 95%, at least 97%, or at least 99% diastereomeric purity. In some such embodiments, the method does not include a chiral purification step (e.g., resolution by crystallization or chromatography). In some such embodiments, the method produces a composition having at least 85% of one diastereomer and not more than 15% of any other diastereomer. In some such embodiments, the method produces a composition having at least 90% of one diastereomer and not more than 10% of any other diastereomer. In some such embodiments, the method produces a composition having at least 95% of one diastereomer and not more than 5% of any other diastereomer. In some such embodiments, the method produces a composition having at least 97% of one diastereomer and not more than 3% of any other diastereomer. In some such embodiments, the method produces a composition having at least 99% of one diastereomer and not more than 1% of any other diastereomer. In certain embodiments, a chiral purification step may be employed to access enantioenriched/pure products as needed based on the optical purity of the chiral intermediates employed. In certain embodiments, the method employs an optically pure starting material. Thus, in certain embodiments, the desired purity can be achieved without the use of a chiral purification step.

In certain embodiments, the method proceeds with an enantioenriched hydrindane (for example, prepared from an inexpensive chiral starting material like epichlorohydrin) and produces a composition having at least 80%, at least 85%, at least 90%, at least 95%, at least 97%, or at least 99% enantiomeric purity. In some such embodiments, the method does not include a chiral purification step (e.g., resolution by crystallization or chromatography). In some such embodiments, the method produces a composition having at least 85% of one enantiomer and not more than 15% of the other enantiomer without employing a chiral purification step. In some such embodiments, the method produces a composition having at least 90% of one enantiomer and not more than 10% of the other enantiomer without employing a chiral purification step. In some such embodiments, the method produces a composition having at least 95% of one enantiomer and not more than 5% of the other enantiomer without employing a chiral purification step. In some such embodiments, the method produces a composition having at least 97% of one enantiomer and not more than 3% of the other enantiomer without employing a chiral purification step. In some such embodiments, the method produces a composition having at least 99% of one enantiomer and not more than 1% of the other enantiomer without employing a chiral purification step. In certain embodiments, a chiral purification step may be employed to removal residual enantiomeric impurities or to resolve a racemic product (for example, a diastereomerically enriched, or pure, product derived from a racemic starting material).

The following general scheme is representative of a particular embodiment of the method and allows for concise and stereoselective synthesis of "C19" tetracyclic compounds:

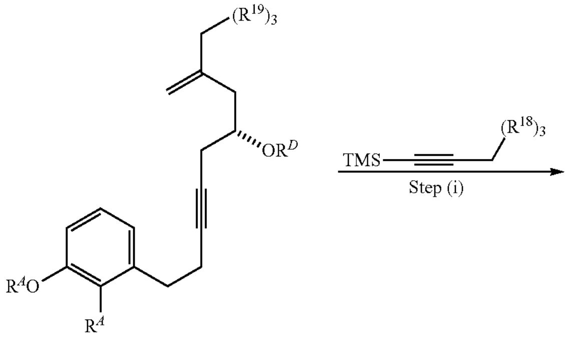

Enyne (a)

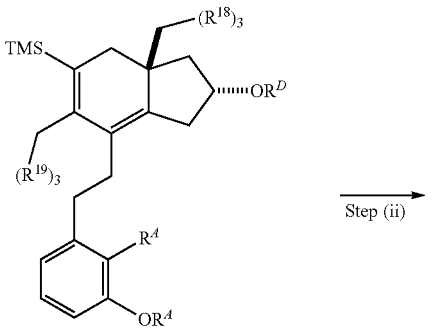

Hydrindane (a)

-continued

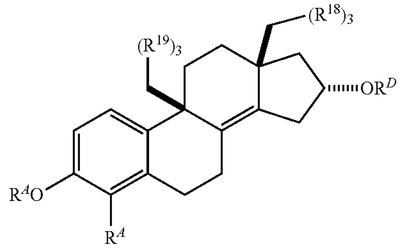

Steroid (a)-anti

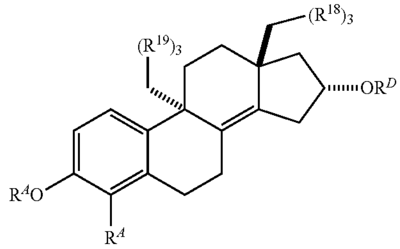

Steroid (a)-syn

Step (i) is a metallacycle-mediated annulation reaction between readily available Enyne (a) and an optionally substituted alkyne (e.g., in the presence of $Ti(Oi\text{-}Pr)_4$, n-BuLi, and PhMe) to provide Hydrindane (a), which possesses the C13 quaternary center. While step (i) depicts an optionally substituted trimethylsilypropyne, alternative compounds such as those having a simple internal alkyne (without a TMS) or an alternative to the silyl group (or stannyl group, for example) on the alkyne may also be used.

Step (ii) is a diastereoselective cyclization, which may comprise acid-mediated protodesilylation, followed by a second regioselective protonation of the diene to deliver a presumed transient fully substituted allylic cation intermediate (not depicted), and intramolecular regio- and stereoselective Friedel-Crafts alkylation to establish the fused C19 tetracyclic compounds named in the Scheme as "Steroid (a)-anti" and "Steroid (a)-syn".

The following general scheme depicts exemplary methods for converting a substituted hydrindane to a steroidal tetracycle:

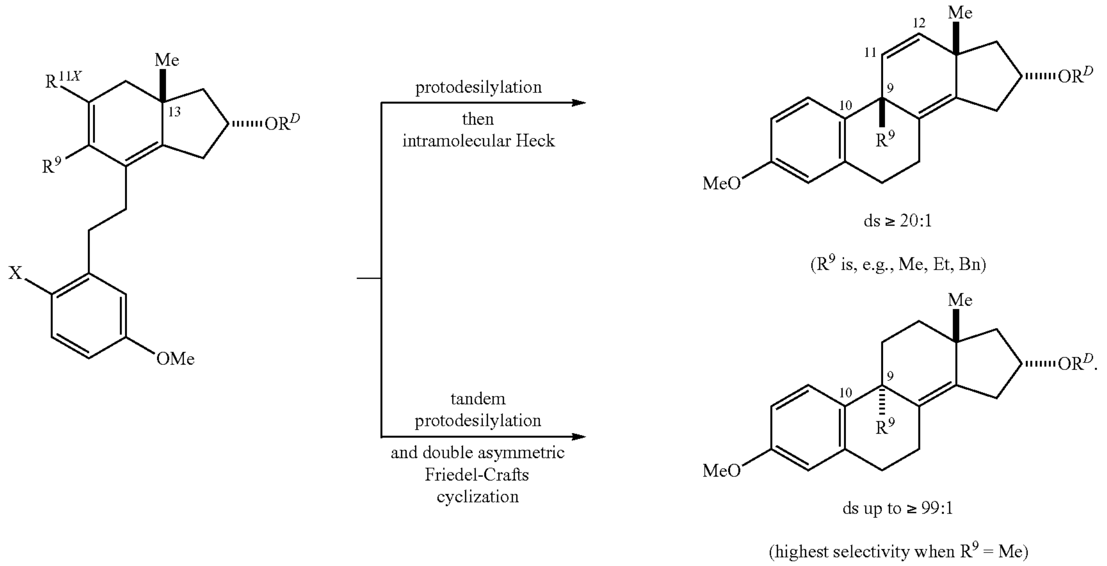

$R^9$ = $C_{1-6}$-alkyl such as Me or Et, $-(CH_2)_m-C_{6-10}$-aryl such as Bn or Ph X = H or group suitable for intramolecular Heck reaction such as OTf $R^D$ = H or $C_{1-6}$-alkyl $R^{11X}$ = organosilicon substituent such as TMS In certain embodiments, the present disclosure provides a method for forming a steroidal C9-C10 bond to yield a 9β, 13β syn-isomer, the method comprising the steps of (a) providing a hydrindane of Formula (Y1) and (b) converting the hydrindane of Formula (Y1) to a tetracyclic compound by intramolecular formation of the C9-C10 bond, wherein step (b) comprises an intramolecular Heck reaction:

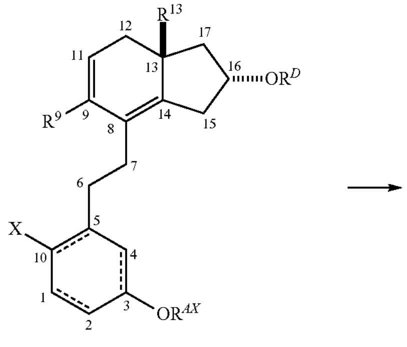

(Int. Hydrindane Y1)

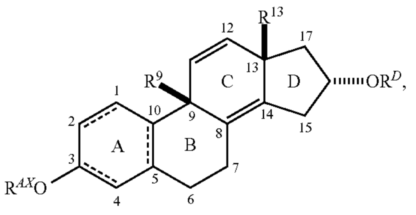

9beta, 13beta syn-iomer wherein X is a functionality suitable for a Heck reaction (e.g., halogen or trifluoromethanesulfonate) and $R^{AX}$, $R^9$, $R^{13}$, and $R^D$ are defined herein.

In certain embodiments, the present disclosure provides a method for forming a steroidal C9-C10 bond to yield a 9α, 13α syn-isomer, the method comprising the steps of (a) providing a hydrindane of Formula (Y2) and (b) converting the hydrindane of Formula (Y2) to a tetracyclic compound by intramolecular formation of the C9-C10 bond, wherein step (b) comprises an intramolecular Heck reaction:

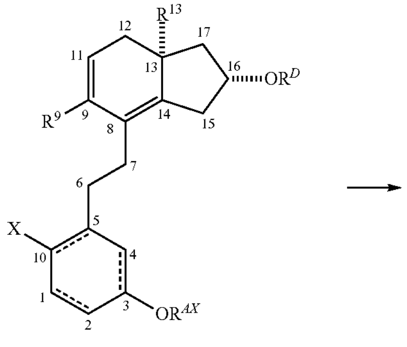

(Int. Hydrindane Y2)

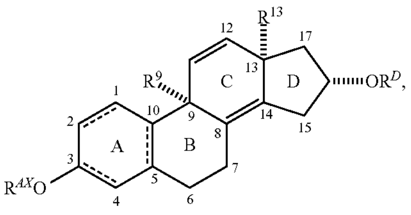

9alpha, 13alpha syn-iomer wherein X is a functionality suitable for a Heck reaction (e.g., halogen or trifluoromethanesulfonate) and $R^{AX}$, $R^{10}$, $R^{13}$, and $R^D$ are defined herein.

The examples presented herein demonstrate the ability to generate a variety of tetracyclic terpenoid motifs through a sequence of alkoxide-directed metallacycle-mediated annulative cross-coupling, followed by cyclization through C9-C10 bond-formation either by double asymmetric Friedel-Crafts cyclization of stereoselective Heck cyclization. These two cyclization technologies are distinct, with one generally producing tetracycles with C9/C13-anti stereochemistry and saturation at C11 and C12, while the other selectively generates tetracycles with C9/C13-syn-stereochemistry and an additional unsaturation between C11 and C12. In general, the syn-selective cyclizations appear more predictable across a varied substrate scope, with all examples leading to products with ds≥20:1, while the anti-selective reactions appear more sensitive to changes in substrate structure (particularly C9 and C16). Finally, the tetracyclic products obtained from these reactions could be smoothly advanced to rearranged tetracyclic products bearing C10/C13 quaternary centers, demonstrating that the oxidative rearrangement is compatible with varying C9 substitution.

In one aspect, the present disclosure provides a method for shifting a substituent of a steroidal tetracycle from C9 to C10. The following general scheme is representative of a particular embodiment of the method:

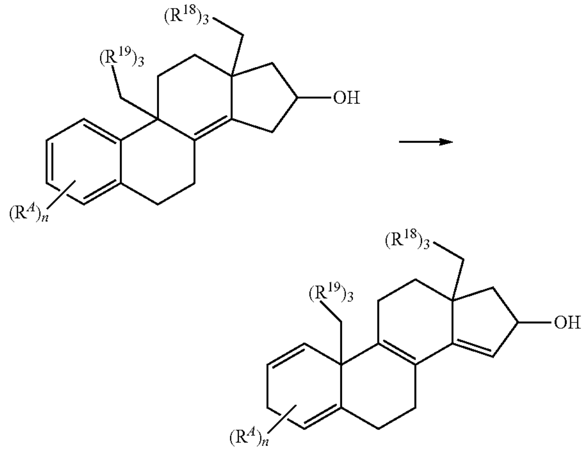

In certain embodiments, an oxidative rearrangement marked by a 1,2-alkyl shift from C9 to C10 is employed. In some such embodiments, concomitant establishment of an A-ring dienone is achieved.

In certain embodiments, the method is carried out in the presence of an oxidant. In certain embodiments, the oxidant is an aryliodine(II) carboxylate, such as is phenyliodo(III) diacetate (PIDA) or (bis(trifluoroacetate)iodo)benzene (PIFA). In some such embodiments, the oxidant is phenyliodo(III)diacetate (PIDA).

In one aspect, the present disclosure provides a method for manufacturing a tetracyclic compound, such as a compound having the generic C19 steroidal core skeleton described herein. The method comprises converting a silyl-substituted hydrindane to a steroidal tetracycle. The method further comprises shifting a substituent of the steroidal tetracycle from the carbon atom at position 9 (C9) to the carbon atom at position 10 (C10). The following general scheme is representative of a particular embodiment of the method:

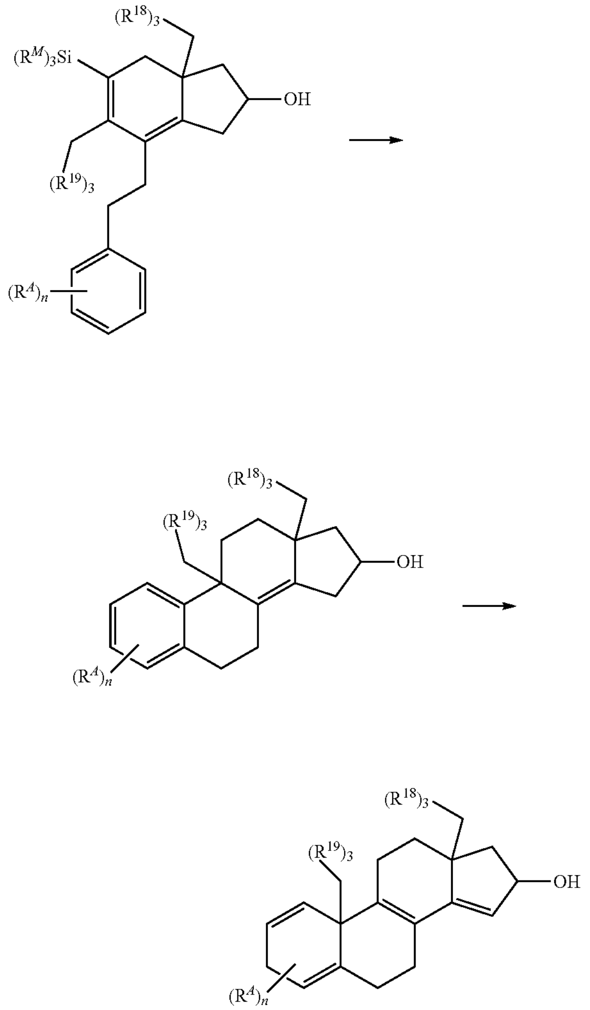

In one aspect, the present disclosure includes intermediate compounds useful in the preparation of, inter alia, steroidal tetracycles disclosed herein.

In one particular aspect, the present disclosure provides an intermediate compound that has a structure corresponding to:

(INT-A-1)

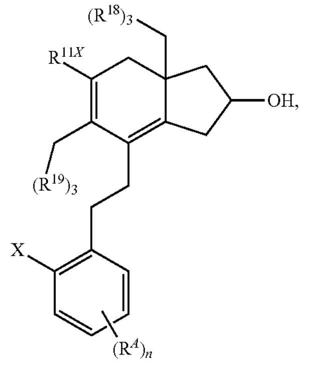

-continued (INT-A-2)

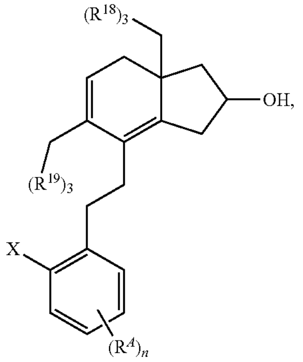

(INT-A-3)

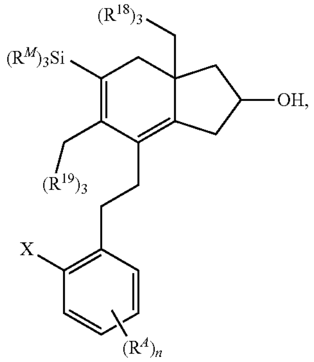

or (INT-A-4)

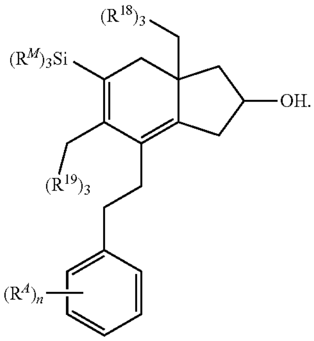

In any aspect or embodiment described herein, variables shown in generic schemes and intermediates may have the following meanings:

each $R^M$ is independently selected from the group consisting of hydrogen, $C_{1-6}$-alkyl, trimethylsilyl, $C_{6-10}$-aryl, 5- to 10-membered heteroaryl, arylalkyl, and —$OR^{MX}$, wherein $R^{MX}$ is hydrogen, $C_{1-6}$-alkyl, or $C_{6-10}$-aryl; and X is halogen or trifluoromethanesulfonate (—OTf) or other functionality suitable for a Heck reaction or radical cyclization.

In another particular aspect, the present disclosure provides an intermediate compound that has a structure corresponding to:

(INT-B)

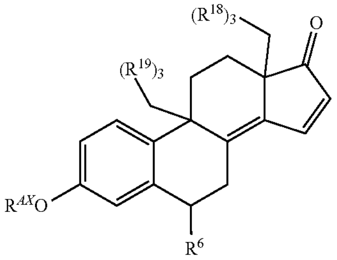

(INT-B')

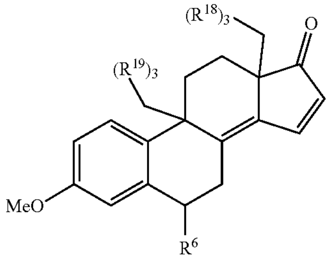

(INT-B'')

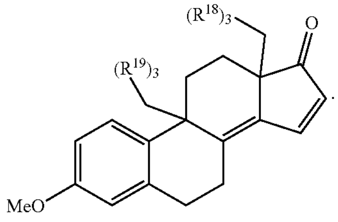

In certain particular embodiments, the intermediate compound has a structure corresponding to:

(INT-B-1)

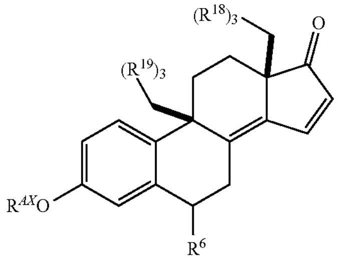

(INT-B'-1)

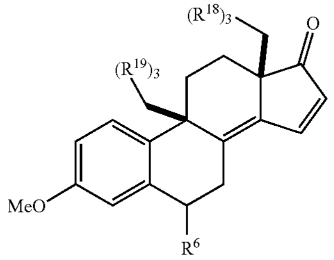

-continued (INT-B″-1)

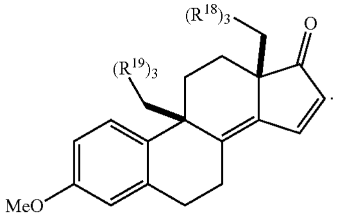

C. EXEMPLARY COMPOUNDS

In one aspect, this disclosure provides a compound, intermediate, or salt thereof, wherein the compound either has a structure corresponding to Formula (I-A) or Formula (II-A), or could be transformed to such structures by methods well known to those skilled in the art of synthetic organic chemistry:

(I-A)

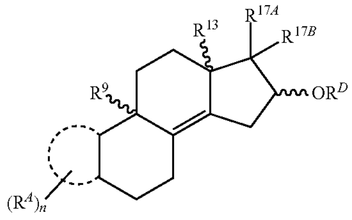

(II-A)

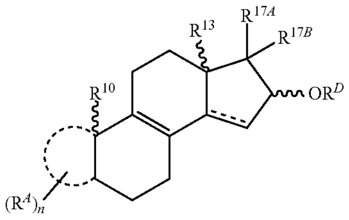

In certain embodiments, the compound either has a structure corresponding to Formula (I-A') or Formula (II-A'), or could be transformed to such structures by methods well known to those skilled in the art of synthetic organic chemistry:

(I-A')

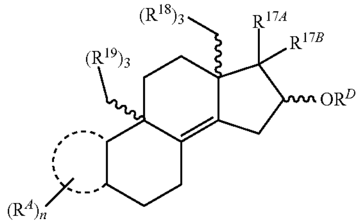

-continued (II-A')

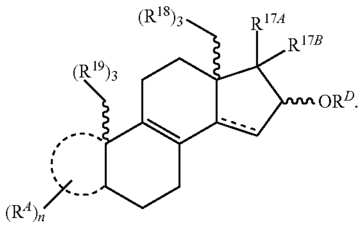

In certain embodiments, the substituents of Formula (I-A) or Formula (I-A') attached to carbon C9 and carbon C13 by have the same orientation (e.g., both or both ). In certain other embodiments, the substituents of Formula (I-A) or Formula (I-A') attached to carbon C9 and carbon C13 by have different orientations (e.g., one and the other ).

In certain embodiments, the substituents of Formula (II-A) or Formula (II-A') attached to carbon C10 and carbon C13 by have the same orientation (e.g., both or both ). In certain other embodiments, the substituents of Formula (II-A) or Formula (II-A') attached to carbon C10 and carbon C13 by have different orientations (e.g., one and the other ).

In some such embodiments, the compound either has a structure corresponding to Formula (I-A1), (I-A2), (I-A3), (I-A4), (I-A5), or (I-A6), or could be transformed to such structures by methods well known to those skilled in the art of synthetic organic chemistry:

(I-A1)

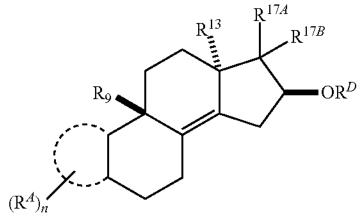

(I-A2)

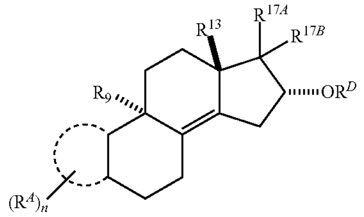

(I-A3)

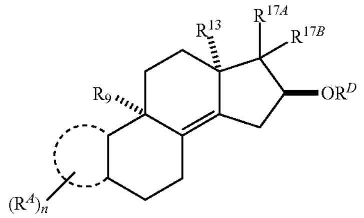

-continued (I-A4)

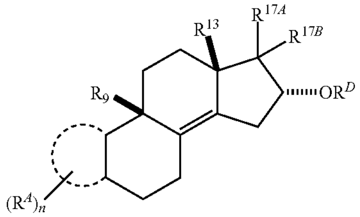

(I-A5)

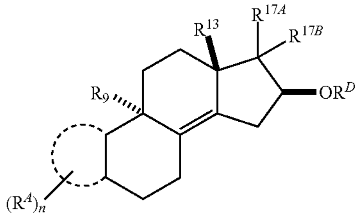

(I-A6)

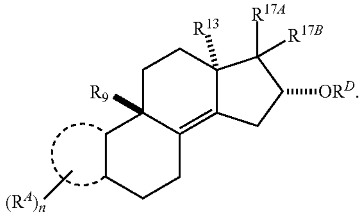

In some such embodiments, the compound either has a structure corresponding to Formula (I-A1.1), (I-A2.1), (I-A3.1), (I-A4.1), (I-A5.1), or (I-A6.1), or could be transformed to such structure by methods well known to those skilled in the art of synthetic organic chemistry:

(I-A1.1)

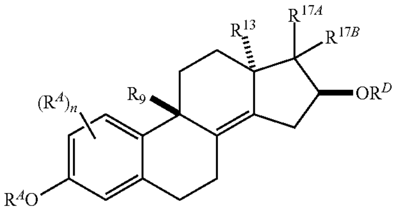

(I-A2.1)

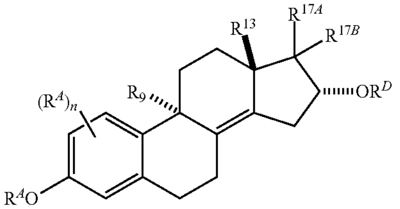

(I-A3.1)

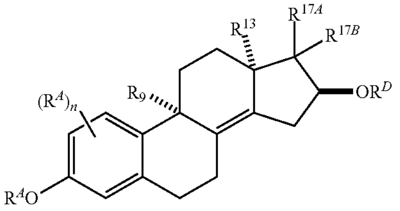

-continued (I-A4.1)

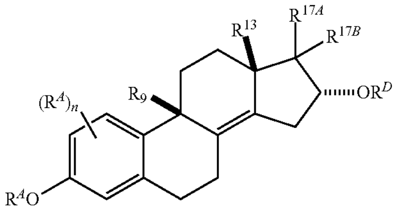

(I-A5.1)

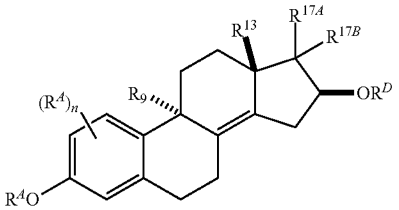

(I-A6.1)

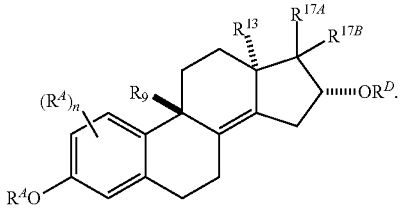

In some such embodiments, the compound either has a structure corresponding to Formula (I-A1.2), (I-A2.2), (I-A3.2), (I-A4.2), (I-A5.2), or (I-A6.2), or could be transformed to such structure by methods well known to those skilled in the art of synthetic organic chemistry:

(I-A1.2)

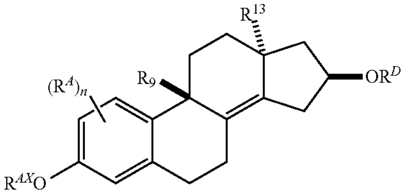

(I-A2.2)

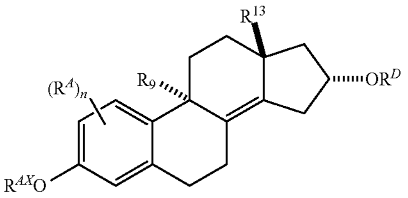

(I-A3.2)

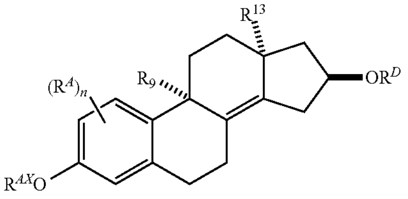

-continued (I-A4.2)

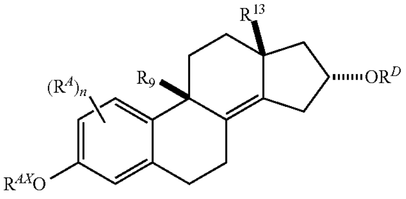

(I-A5.2)

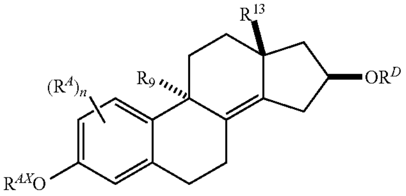

(I-A6.2)

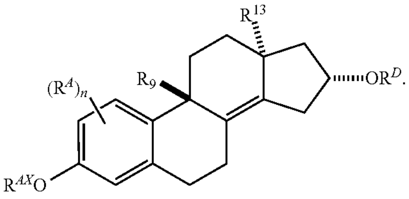

In some such embodiments, the compound either has a structure corresponding to Formula (II-A1), (II-A2), (II-A3), (II-A4), (II-A5), or (II-A6), or could be transformed to such structure by methods well known to those skilled in the art of synthetic organic chemistry:

(II-A1)

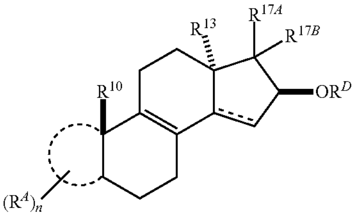

(II-A2)

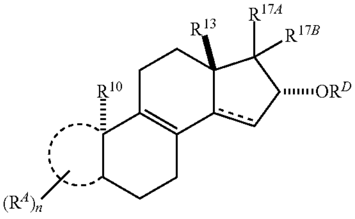

(II-A3)

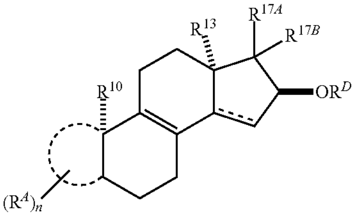

-continued (II-A4)

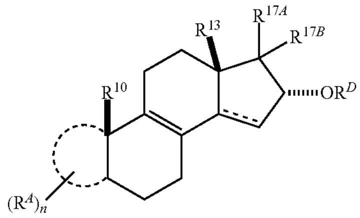

(II-A5)

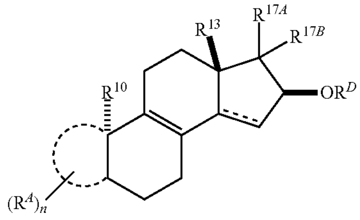

(II-A6)

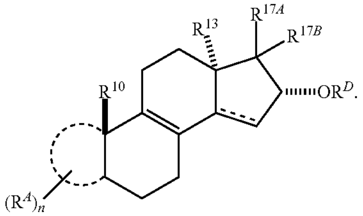

In some such embodiments, the compound either has a structure corresponding to Formula (II-A1.1), (II-A2.1), (II-A3.1), (II-A4.1), (II-A5.1), or (II-A6.1), or could be transformed to such structure by methods well known to those skilled in the art of synthetic organic chemistry:

(II-A1.1)

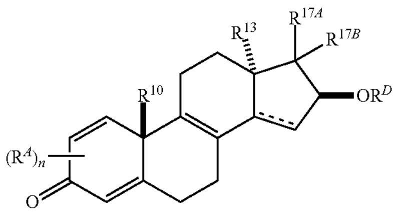

(II-A2.1)

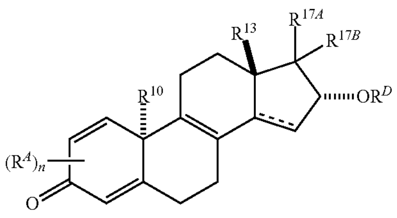

(II-A3.1)

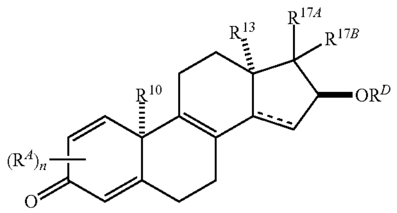

-continued (II-A4.1)

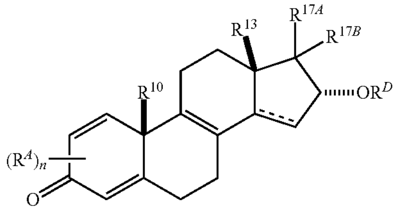

(II-A5.1)

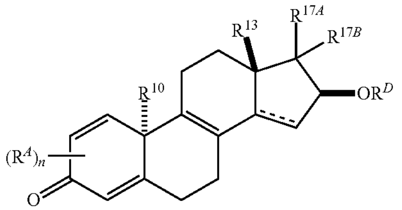

(II-A6.1)

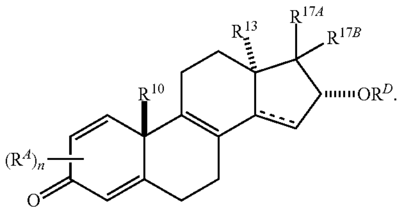

In some such embodiments, the compound either has a structure corresponding to Formula (II-A1.2), (II-A2.2), (II-A3.2), (II-A4.2), (II-A5.2), or (II-A6.2), or could be transformed to such structure by methods well known to those skilled in the art of synthetic organic chemistry:

(II-A1.2)

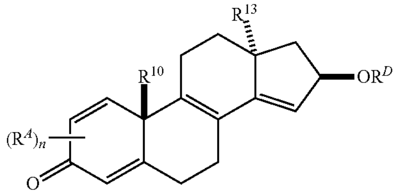

(II-A2.2)

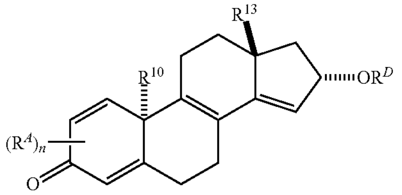

(II-A3.2)

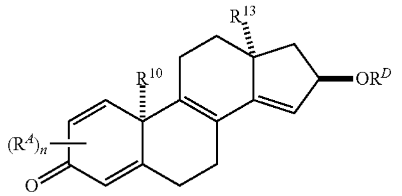

-continued (II-A4.2)

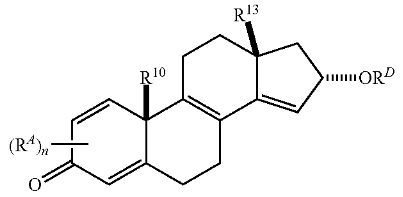

(II-A5.2)

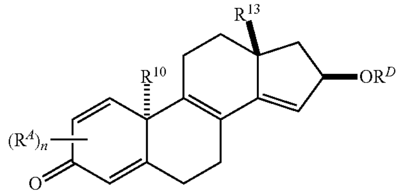

(II-A6.2)

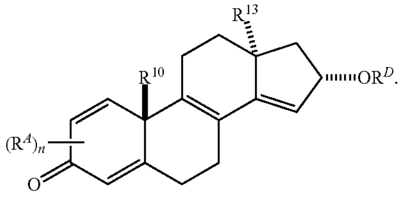

In another aspect, this disclosure provides a compound, intermediate, or salt thereof, wherein the compound either has a structure corresponding to Formula (III-A), or could be transformed to such structure by methods well known to those skilled in the art of synthetic organic chemistry:

(III-A)

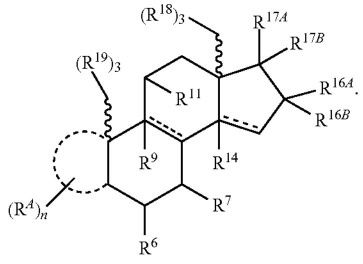

In certain embodiments, the substituents attached to carbon C10 and carbon C13 by have the same orientation (e.g., both or both ). In certain other embodiments, the substituents attached to carbon C10 and carbon C13 by have different orientations (e.g., one and the other ).

In some such embodiments, the compound of Formula (III) is a synthetic androstane or pregnane, and variants thereof accessible from such intermediates by methods well known to those skilled in the art of synthetic organic chemistry.

In certain embodiments, the compound either has a structure corresponding to Formula (III-B), or could be transformed to such structure by methods well known to those skilled in the art of synthetic organic chemistry:

(III-B)

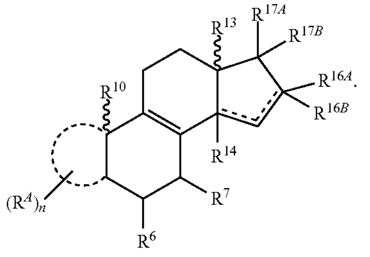

The compound of Formula (III-B) includes a double bond between carbon C8 and carbon C9 (i.e., 8,9-unsaturated) and, optionally, (i) a double bond between carbon C14 and carbon C15 (i.e., 8,9,14,15-unsaturated) or (ii) a double bond between carbon C15 and carbon C16, provided that if the bond between carbon C14 and carbon C15 is a double bond, then $R^{14}$ is absent.

In certain embodiments, the substituents of Formula (III-B) attached to carbon C10 and carbon C13 by have the same orientation (e.g., both or ). In certain other embodiments, the substituents of Formula (III-B) attached to carbon C10 and carbon C13 by have different orientations (e.g., one and the other ).

In some such embodiments, the compound either has a structure corresponding to Formula (III-B1) or Formula (III-B2), or could be transformed to such structures by methods well known to those skilled in the art of synthetic organic chemistry:

(III-B1)

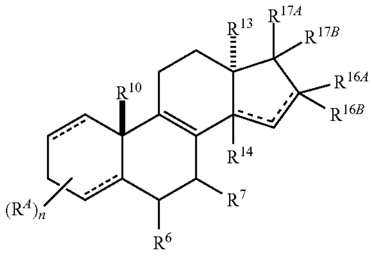

(III-B2)

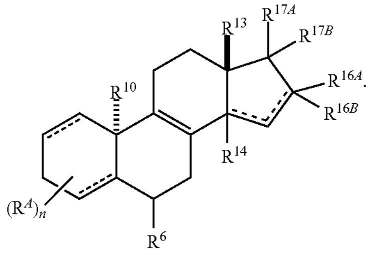

In certain embodiments, the compound either has a structure corresponding to Formula (III-C), or could be transformed to such structure by methods well known to those skilled in the art of synthetic organic chemistry:

(III-C)

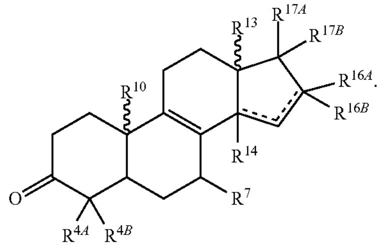

In certain embodiments, the substituents of Formula (III-C) attached to carbon C10 and carbon C13 by have the same orientation (e.g., both or both ). In certain other embodiments, the substituents of Formula (III-C) attached to carbon C10 and carbon C13 by have different orientations (e.g., one and the other ).

In certain embodiments, the compound either has a structure corresponding to Formula (III-D) or Formula (III-E), or could be transformed to such structure by methods well known to those skilled in the art of synthetic organic chemistry:

(III-D)

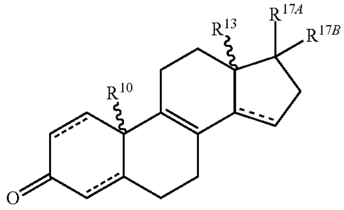

(III-E)

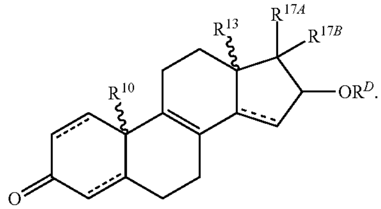

The compound of Formula (III-D) or Formula (III-E) includes a double bond between carbon C8 and carbon C9 (i.e., 8,9-unsaturated) and, optionally, a double bond between carbon C14 and carbon C15 (i.e., 8,9,14,15-unsaturated). In addition, the compound of Formula (III-D) or Formula (III-E) optionally includes double bonds between carbon C1 and carbon C2 and/or carbon C4 and carbon C5.

In certain embodiments, the substituents of Formula (III-D) or Formula (III-E) attached to carbon C10 and carbon C13 by have the same orientation (e.g., both or both ). In certain other embodiments, the substituents of Formula (III-D) attached to carbon C10 and carbon C13 by have different orientations (e.g., one and the other ).

In one particular embodiment, the substituents attached to carbon C10 and carbon C13 of Formula (III-D) or Formula (III-E) are both in the same orientation (e.g., both ). For example, the compound may have a structure corresponding to Formula (III-D1), Formula (III-D2), Formula (III-D3), Formula (III-D4), Formula (III-E1), Formula (III-E2), Formula (III-E3), or Formula (III-E4):

(III-D1)

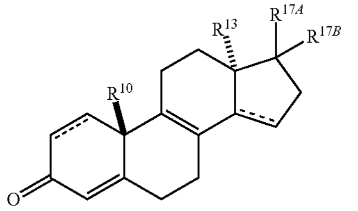

(III-E1)

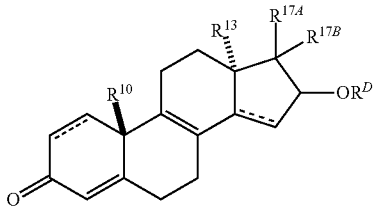

(III-D2)

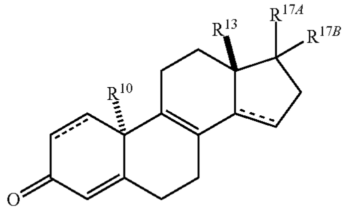

(III-E2)

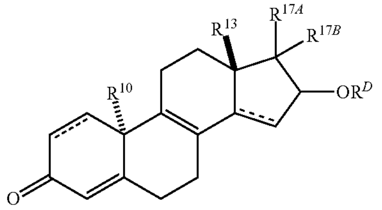

(III-D3)

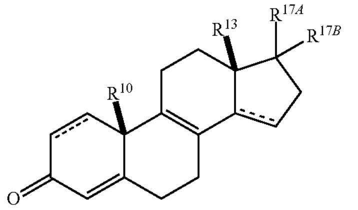

(III-E3)

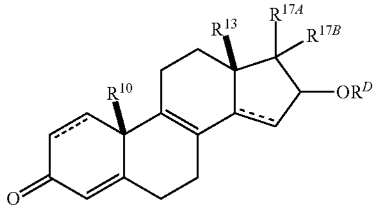

(III-D4)

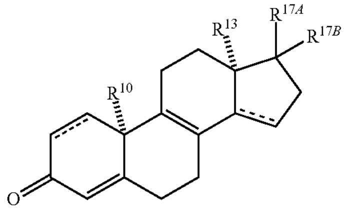

-continued (III-E4)

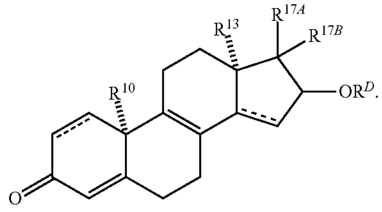

In certain embodiments, the compound may have a structure corresponding to Formula (III-D1), Formula (III-D2), Formula (III-D3), Formula (III-D4), Formula (III-E1), Formula (III-E2), Formula (III-E3), or Formula (III-E4), where $R^{10}$ is methyl, $R^{13}$ is methyl, $R^{17A}$ and $R^{17B}$ are selected from the group consisting of hydrogen, $C_{1-6}$-alkyl, hydroxy, $C_{1-6}$-alkoxy, and —C(O)—$C_{1-10}$-alkyl, and $R^D$ is hydrogen or $C_{1-6}$-alkyl.

In another aspect, this disclosure provides a compound, intermediate, or salt thereof, wherein the compound either has a structure corresponding to Formula (X-A) of (X-B), or could be transformed to such structure by methods well known to those skilled in the art of synthetic organic chemistry:

(X-A)

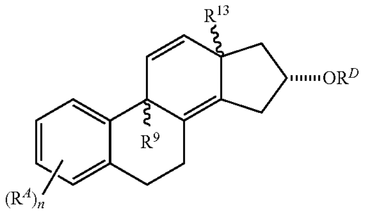

or (X-B)

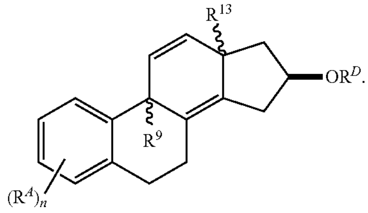

In certain embodiments, the substituents of Formula (X-A) or (X-B) attached to carbon C9 and carbon C13 by  have the same orientation and are both . In certain other embodiments, the substituents of Formula (X-A) or (X-B) attached to carbon C9 and carbon C13 by  have the same orientation and are both .

In one particular embodiment, the substituents attached to carbon C9 and carbon C13 of Formula (X-A) are both in the same orientation (e.g., both ). For example, the compound may have a structure corresponding to Formula (X-A1):

(X-A1)

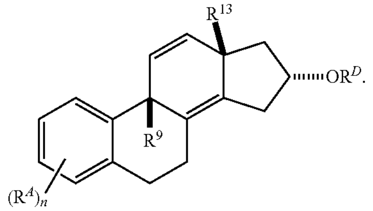

In one particular embodiment, the substituents attached to carbon C9 and carbon C13 of Formula (X-A) are both in the same orientation (e.g., both ıııııııı). For example, the compound may have a structure corresponding to Formula (X-A2):

(X-A2)

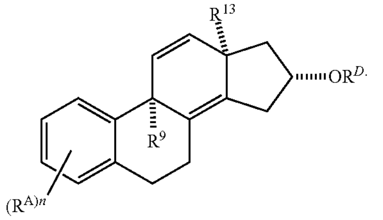

In any aspect or embodiment described herein, a dashed semi-circle (e.g., representing the A ring) represents a saturated or unsaturated carbocyclic or heterocyclic ring containing 5 or 6 carbon ring atoms. In some such embodiments, the A ring is optionally substituted benzene. In other such embodiments, the A ring is an optionally substituted 6-membered carbocyclic ring that is saturated or partially unsaturated. In still other such embodiments, the A ring is a 5- or 6-membered heterocyclic ring, such as thiophene or furan.

In any aspect or embodiment described herein, variables shown in generic structures may have the following meanings:

n is an integer selected from the group consisting of 0, 1, 2, 3, 4, 5, 6, 7, and 8;

m is an integer selected from the group consisting of 0, 1, 2, and 3;

each $R^A$ is independently selected from the group consisting of hydrogen, $C_{1-10}$-alkyl, $C_{2-10}$-alkenyl, $C_{2-10}$-alkynyl, $C_{1-10}$-haloalkyl, halogen, oxo, —$OR^{AX}$, —$SR^{AY}$, —$S(O)_2NR^{Z1}R^{Z2}$, —$S(O)_2R^{Z1}$, —S(O) $R^{Z1}$, —$NR^{Z1}R^{Z2}$, —$N(R^{Z1})$ C(O) $R^{Z2}$, —$N(R^{21})$ $S(O)_2R^{Z2}$, $C_{6-10}$-aryl, and 5- to 10-membered heteroaryl, wherein $R^{AX}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, —$S(O)_2NR^{Z1}R^{Z2}$, —$S(O)_2R^{21}$, $C_{6-10}$-aryl, or 5- to 10-membered heteroaryl, wherein $R^{AY}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, $C_{6-10}$-aryl, or 5- to 10-membered heteroaryl, wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy;

X is a halogen, trifluoromethanesulfonate (—OTf), or other functionality suitable for a Heck reaction;

each of $R^{4A}$ and $R^{4B}$ are independently selected from the group consisting of hydrogen, $C_{1-10}$-alkyl, $C_{2-10}$-alkenyl, $C_{2-10}$-alkynyl, $C_{1-10}$-haloalkyl, and halogen;

$R^6$ is selected from the group consisting of hydrogen, $C_{1-10}$-alkyl, $C_{2-10}$-alkenyl, $C_{2-10}$-alkynyl, $C_{1-10}$-haloalkyl, and halogen;

$R^7$ is selected from the group consisting of hydrogen, $C_{1-10}$-alkyl, $C_{2-10}$-alkenyl, $C_{2-10}$-alkynyl, $C_{1-10}$-haloalkyl, halogen, hydroxy, and oxo;

$R^9$ is selected from the group consisting of hydrogen, $C_{1-10}$-alkyl, $C_{2-10}$-alkenyl, $C_{2-10}$-alkynyl, $C_{1-10}$-haloalkyl, halogen, —$(CH_2)_m$—$C_{6-10}$-aryl, and —$(CH_2)_m$— 5- to 10-membered heteroaryl;

$R^{10}$ is selected from the group consisting of hydrogen, $C_{1-10}$-alkyl, $C_{2-10}$-alkenyl, $C_{2-10}$-alkynyl, $C_{1-10}$-haloalkyl, halogen, —$(CH_2)_m$—$C_{6-10}$-aryl, and —$(CH_2)_m$— 5- to 10-membered heteroaryl;

$R^{11}$ is selected from the group consisting of hydrogen, $C_{1-10}$-alkyl, $C_{2-10}$-alkenyl, $C_{2-10}$-alkynyl, $C_{1-10}$-haloalkyl, halogen, hydroxy, and $OR^{CX}$, wherein $R^{CX}$ is $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, $C_{6-10}$-aryl, or 5- to 10-membered heteroaryl;

$R^{11X}$ is hydrogen or an organosilicon substituent such as trimethylsilyl (TMS), or alternatively an organotin or organogermanium substituent;

$R^{13}$ is selected from the group consisting of $C_{1-10}$-alkyl, $C_{2-10}$-alkenyl, $C_{2-10}$-alkynyl, $C_{1-10}$-haloalkyl, —$(CH_2)_m$—$C_{6-10}$-aryl, and —$(CH_2)_m$— 5- to 10-membered heteroaryl;

$R^{14}$ is selected from the group consisting hydrogen, $C_{1-10}$-alkyl, $C_{2-10}$-alkenyl, $C_{2-10}$-alkynyl, $C_{1-10}$-haloalkyl, and halogen;

each of $R^{16A}$ and $R^{16B}$ are independently selected from the group consisting hydrogen, $C_{1-10}$-alkyl, $C_{2-10}$-alkenyl, $C_{2-10}$-alkynyl, $C_{1-10}$-haloalkyl, halogen, hydroxy, and $OR^D$;

$R^D$ is selected from the group consisting of hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, $C_{6-10}$-aryl, and 5- to 10-membered heteroaryl;

each of $R^{17A}$ and $R^{17B}$ are independently selected from the group consisting of hydrogen, $C_{1-10}$-alkyl, $C_{2-10}$-alkenyl, $C_{2-10}$-alkynyl, $C_{1-10}$-haloalkyl, halogen, hydroxy, $C_{1-6}$-alkoxy, $C_{1-10}$-alkyl-C(O), —C(O)—$C_{1-10}$-alkyl, —C(O)—$C_{1-10}$-hydroxyalkyl, —C(O)—$C_{1-10}$-alkyl-$C_{6-10}$-aryl, —C(O)—$C_{1-10}$-alkyl-heteroaryl, —C(O)—$C_{6-10}$-aryl, —C(O)-heteroaryl, —O—C(O)—$C_{1-6}$-alkyl, $C_{6-10}$-aryl, and 5- to 10-membered heteroaryl, or $R^{17A}$ and $R^{17B}$ together form an oxo;

each $R^{18}$ is independently selected from the group consisting hydrogen, $C_{1-10}$-alkyl, $C_{2-10}$-alkenyl, $C_{2-10}$-alkynyl, $C_{1-10}$-haloalkyl, halogen, $C_{6-10}$-aryl, and 5- to 10-membered heteroaryl;

each $R^{19}$ is independently selected from the group consisting hydrogen, $C_{1-10}$-alkyl, $C_{2-10}$-alkenyl, $C_{2-10}$-alkynyl, $C_{1-10}$-haloalkyl, halogen, $C_{6-10}$-aryl, and 5- to 10-membered heteroaryl; and each ---- independently represents a single bond or a double bond;

wherein any $C_{6-10}$-aryl or 5- to 10-membered heteroaryl is optionally substituted with one or more halogen, hydroxy, $C_{1-6}$-alkyl, $C_{1-6}$-haloalkyl, or $C_{1-6}$-alkoxy.

In certain preferred embodiments, n is 1 or 2. In some such preferred embodiments, n is 1. In some such preferred embodiments, n is 2.

In certain preferred embodiments, m is 0 or 1. In some such preferred embodiments, m is 0. In some such preferred embodiments, m is 1.

In certain preferred embodiments, $R^A$ is —OH, —O—$C_{1-6}$-alkyl, or oxo. In some such preferred embodiments, $R^A$ is —OH or oxo.

In certain preferred embodiments, n is 2 and one $R^A$ is —OH or —O—$C_{1-6}$-alkyl and the other $R^A$ is $C_{1-10}$-alkyl, such as methyl, or —$OR^{AX}$ wherein $R^{AX}$ is $C_{1-6}$-alkyl, such as methyl.

In certain preferred embodiments, X is a halogen or trifluoromethanesulfonate (—OTf).

In certain preferred embodiments, $R^{4A}$ is hydrogen or $C_{1-10}$-alkyl. In some such preferred embodiments, $R^{4A}$ is methyl. In certain preferred embodiments, $R^{4B}$ is hydrogen or $C_{1-10}$-alkyl. In some such preferred embodiments, $R^{4B}$ is methyl.

In certain preferred embodiments, each of $R^{4A}$ and $R^{4B}$ are methyl.

In certain preferred embodiments, $R^6$ is hydrogen, $C_{1-10}$-alkyl, $C_{1-10}$-haloalkyl, or halogen. In some such preferred embodiments, $R^6$ is hydrogen or methyl. In some such preferred embodiments, $R^6$ is hydrogen.

In certain preferred embodiments, $R^7$ is hydrogen, hydroxy, or oxo. In some such preferred embodiments, $R^7$ is hydrogen or oxo. In some such preferred embodiments, $R^7$ is hydrogen.

In certain preferred embodiments, $R^9$ is hydrogen, $C_{1-10}$-alkyl, $C_{1-10}$-haloalkyl, halogen, or —$(CH_2)_m$—$C_{6-10}$-aryl. In some such preferred embodiments, $R^9$ is hydrogen or halogen. In some such preferred embodiments, $R^9$ is hydrogen. In some such preferred embodiments, $R^9$ is $C_{1-10}$-alkyl, such as methyl, ethyl, or propyl. In some such preferred embodiments, $R^9$ is —$(CH_2)_m$—$C_{6-10}$-aryl, wherein m is 0 or 1. For example, $R^9$ may be phenyl or benzyl.

In certain preferred embodiments, $R^{10}$ is hydrogen, $C_{1-10}$-alkyl, $C_{1-10}$-haloalkyl, halogen, or —$(CH_2)_m$—$C_{6-10}$-aryl. In some such preferred embodiments, $R^{10}$ is hydrogen. In some such preferred embodiments, $R^{10}$ is $C_{1-10}$-alkyl, such as methyl, ethyl, or propyl. In some such preferred embodiments, $R^{10}$ is —$(CH_2)_m$—$C_{6-10}$-aryl, wherein m is 0 or 1. For example, $R^{10}$ may be phenyl or benzyl.

In certain preferred embodiments, $R^{11}$ is hydrogen, hydroxy, or $OR^{CX}$ wherein $R^{CX}$ is $C_{1-6}$-alkyl. In some such preferred embodiments, $R^{11}$ is hydrogen or hydroxy. In some such preferred embodiments, $R^{11}$ is hydrogen.

In certain preferred embodiments, $R^{11X}$ is an organosilicon substituent. For example, in some such embodiments, $R^{11X}$ is —$Si(R^M)_3$, wherein each $R^M$ is independently selected from the group consisting of hydrogen, $C_{1-6}$-alkyl, trimethylsilyl, $C_{6-10}$-aryl, 5- to 10-membered heteroaryl, arylalkyl, and —$OR^{MX}$, wherein $R^{MX}$ is hydrogen, $C_{1-6}$-alkyl, or $C_{6-10}$-aryl. In some such embodiments, $R^{11X}$ is trimethylsilyl (TMS).

In certain preferred embodiments, $R^{13}$ is $C_{1-10}$-alkyl, $C_{1-10}$-haloalkyl, or —$(CH_2)_m$—$C_{6-10}$-aryl. In some such preferred embodiments, $R^{13}$ is $C_{1-10}$-alkyl, such as methyl, ethyl, or propyl. In some such preferred embodiments, $R^{13}$ is —$(CH_2)_m$—$C_{6-10}$-aryl, wherein m is 0 or 1. For example, $R^{13}$ may be phenyl or benzyl.

In certain preferred embodiments, $R^{14}$ is hydrogen or $C_{1-10}$-alkyl. In some such preferred embodiments, $R^{14}$ is methyl. In some such preferred embodiments, $R^{14}$ is hydrogen.

In certain preferred embodiments, both $R^{16A}$ and $R^{16B}$ are hydrogen, $R^{16A}$ is hydrogen and $R^{16B}$ is $C_{1-10}$-alkyl, $R^{16A}$ is hydrogen and $R^{16B}$ is $C_{1-10}$-haloalkyl, or $R^{16A}$ is hydrogen and $R^{16B}$ is $OR^D$ wherein $R^D$ is hydrogen or $C_{1-6}$-alkyl. In some such preferred embodiments, $R^{16A}$ is hydrogen and $R^{16B}$ is hydrogen or $C_{1-10}$-alkyl. In some such preferred embodiments, $R^{16A}$ is hydrogen and $R^{16B}$ is hydrogen. In some such preferred embodiments, $R^{16A}$ is hydrogen and $R^{16B}$ is $OR^D$ where $R^D$ is hydrogen. In some such preferred embodiments, $R^{16A}$ is hydrogen and $R^{16B}$ is $OR^D$ where $R^D$ is $C_{1-6}$-alkyl.

In certain preferred embodiments, $R^D$ is hydrogen.

In certain preferred embodiments, $R^{17A}$ is hydrogen, $C_{1-10}$-alkyl, hydroxy, $C_{1-6}$-alkoxy, —C(O)—$C_{1-10}$-alkyl, —C(O)—$C_{1-10}$-hydroxyalkyl, or —O—C(O)—$C_{1-6}$-alkyl. In some such preferred embodiments, $R^{17A}$ is hydrogen, $C_{1-10}$-alkyl, hydroxy, or $C_{1-6}$-alkoxy.

In certain preferred embodiments, $R^{17B}$ is hydrogen, $C_{1-10}$-alkyl, hydroxy, $C_{1-6}$-alkoxy, —C(O)—$C_{1-10}$-alkyl, —C(O)—$C_{1-10}$-hydroxyalkyl, or —O—C(O)—$C_{1-6}$-alkyl. In some such preferred embodiments, $R^{17B}$ is hydrogen, $C_{1-10}$-alkyl, hydroxy, or $C_{1-6}$-alkoxy.

In certain preferred embodiments, $R^{17A}$ and $R^{17B}$ together form an oxo.

In certain preferred embodiments, each of $R^{17A}$ and $R^{17B}$ are hydrogen.

In certain preferred embodiments, each $R^{18}$ is hydrogen. In other preferred embodiments, two $R^{18}$ are hydrogen and one $R^{18}$ is $C_{1-10}$-alkyl, such as —$CH_3$ or —$CH_2CH_3$. In other preferred embodiments, two $R^{18}$ are hydrogen and one $R^{18}$ is $C_{6-10}$-aryl, such as phenyl.

In certain preferred embodiments, each $R^{19}$ is hydrogen. In other preferred embodiments, two $R^{19}$ are hydrogen and one $R^{19}$ is $C_{1-10}$-alkyl, such as —$CH_3$ or —$CH_2CH_3$. In other preferred embodiments, two $R^{19}$ are hydrogen and one $R^{19}$ is $C_{6-10}$-aryl, such as phenyl.

It is to be understood that any preferred embodiment for a variable (e.g., n, $R^A$, $R^{4A}$, $R^{4B}$, $R^6$, $R^7$, $R^9$, $R^{10}$, $R^{11}$, $R^{13}$, $R^{14}$, $R^{16A}$, $R^{16B}$, $R^D$, $R^{17A}$, $R^{17B}$, $R^{18}$, and $R^{19}$) may be combined with any preferred embodiment for any other variable(s) described herein. Exemplary combinations for compounds having a structure corresponding to Formula (I-A1), (I-A2), (I-A3), (I-A4), (I-A1.1), (I-A2.1), (I-A3.1), (I-A4.1), includes, but is not limited to: n is 0, 1, or 2; each $R^A$, if present, is $C_{1-6}$-alkyl or hydroxy; $R^9$ is $C_{1-6}$-alkyl or —$(CH_2)_m$—$C_{6-10}$-aryl where m is 0 or 1; $R^{13}$ is $C_{1-6}$-alkyl or —$(CH_2)_m$—$C_{6-10}$-aryl where m is 0 or 1; each $R^{17}$ is hydrogen; and $R^D$ is hydrogen or $C_{1-6}$-alkyl. Exemplary combinations for compounds having a structure corresponding to Formula (II-A1), (II-A2), (II-A3), (II-A4), (II-A1.1), (II-A2.1), (II-A3.1), (II-A4.1), includes, but is not limited to: n is 0, 1, or 2; each $R^A$, if present, is $C_{1-6}$-alkyl or oxo; $R^{10}$ is $C_{1-6}$-alkyl or —$(CH_2)_m$—$C_{6-10}$-aryl where m is 0 or 1; $R^{13}$ is $C_{1-6}$-alkyl or —$(CH_2)_m$—$C_{6-10}$-aryl where m is 0 or 1; each $R^{17}$ is hydrogen; and $R^D$ is hydrogen or $C_{1-6}$-alkyl.

In one aspect, this disclosure provides a compound or salt or prodrug thereof, wherein the compound has a structure corresponding to one of the following compounds:

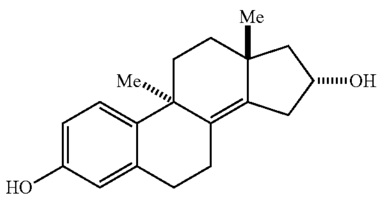

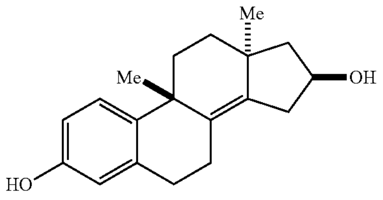

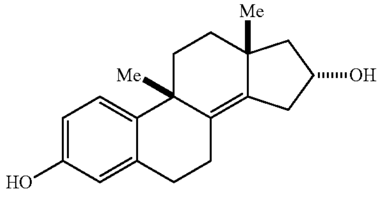

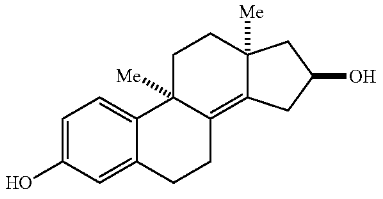

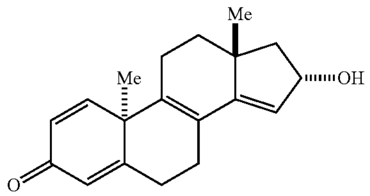

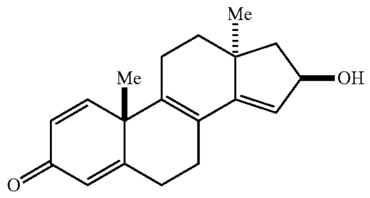

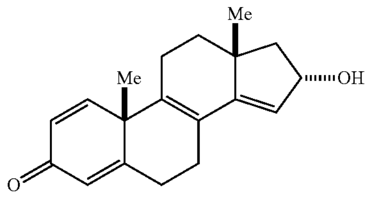

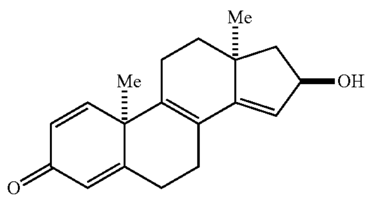

-continued

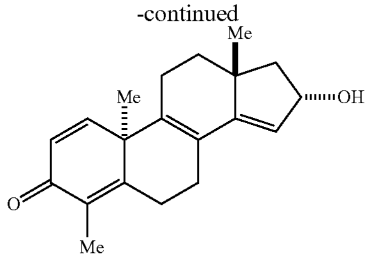

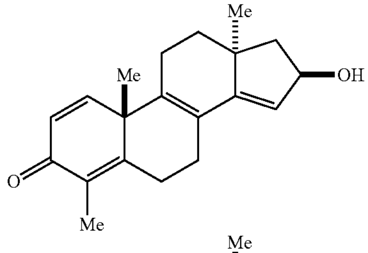

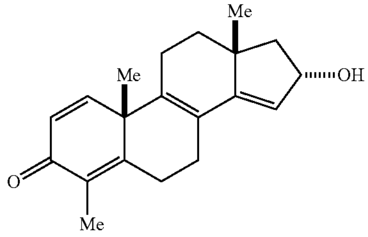

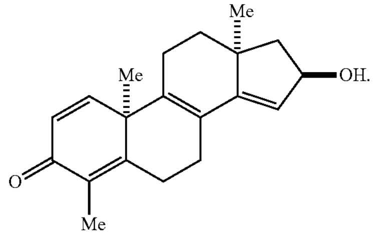

D. METHODS OF USE

In at least one aspect, the present disclosure includes a method for treating or preventing a proliferative disease in a subject in need of such treatment or prevention. Exemplary proliferative diseases include cancers (i.e., "malignant neoplasms"), benign neoplasms, angiogenesis, inflammatory diseases, and autoimmune diseases. In particular, exemplary cancers that may be treated or prevented include breast cancer, prostate cancer, ovarian cancer, acute myeloid leukemia, and glioma.

Thus, one aspect of the present disclosure includes a method for treating a brain tumor. The method comprises administering to a patient in need thereof a therapeutically effective amount of a compound described herein (including, but not limited to, Compound 100 or 101) or a pharmaceutically acceptable salt or prodrug thereof. In some such embodiments, the compound is a selective ERβ agonist. In some embodiments, the compound is Compound 100. In some embodiments, the compound is Compound 101. In some embodiments, the compound (or pharmaceutically acceptable salt thereof) is administered orally. In some embodiments, the brain tumor is a glioma, such as a glioblastoma. In some such embodiments, the brain tumor is selected from the group consisting of astrocytoma, glioblastoma, ependymoma (e.g., anaplastic ependymoma or myxopapillary ependymoma), and oligodendroglioma (e.g., anaplastic oligodendroglioma or anaplastic oligoastrocytoma). In at least one aspect, the present disclosure includes a compound disclosed herein or a pharmaceutically acceptable salt or prodrug thereof for use in a method for treating a cancer, particularly a brain tumor.

In certain embodiments, the compound has a structure corresponding to Formula (I-A1.2), (I-A2.2), (I-A3.2), (I-A4.2), (I-A5.2), or (I-A6.2):

(I-A1.2)

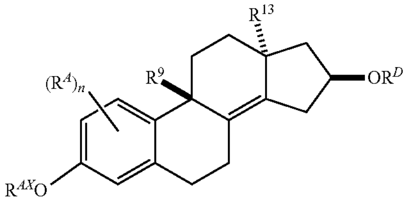

(I-A2.2)

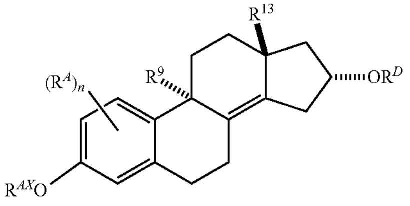

(I-A3.2)

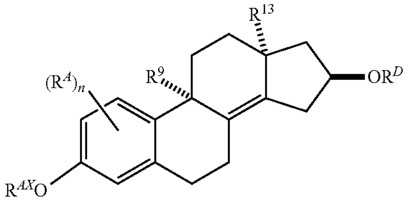

(I-A4.2)

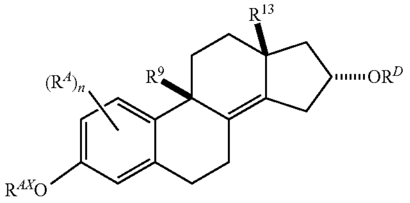

(I-A5.2)

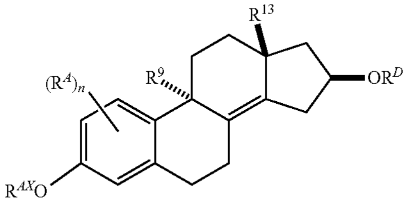

(I-A6.2)

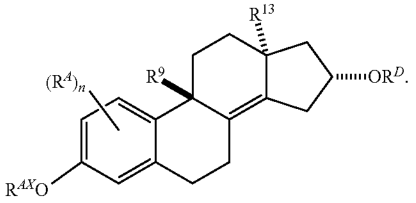

In certain preferred embodiments, n is 1 or 2. In some such preferred embodiments, n is 1. In some such preferred embodiments, n is 2.

In certain preferred embodiments, $R^A$ is $C_{1-10}$-alkyl, such as methyl,

In certain preferred embodiments, $R^{AX}$ is hydrogen or $C_{1-6}$-alkyl. In some such preferred embodiments, $R^{AX}$ is hydrogen.

In certain preferred embodiments, $R^9$ is $C_{1-10}$-alkyl, $C_{1-10}$-haloalkyl, halogen, or $-(CH_2)_m-C_{6-10}$-aryl. In some such preferred embodiments, $R^9$ is halogen. In some such preferred embodiments, $R^9$ is $C_{1-10}$-alkyl, such as methyl, ethyl, or propyl. In some such preferred embodiments, $R^9$ is $-(CH_2)_m-C_{6-10}$-aryl, wherein m is 0 or 1. For example, $R^9$ may be phenyl or benzyl.

In certain preferred embodiments, $R^{13}$ is $C_{1-10}$-alkyl, $C_{1-10}$-haloalkyl, or $-(CH_2)_m-C_{6-10}$-aryl. In some such preferred embodiments, $R^{13}$ is $C_{1-10}$-alkyl, such as methyl, ethyl, or propyl. In some such preferred embodiments, $R^{13}$ is $-(CH_2)_m-C_{6-10}$-aryl, wherein m is 0 or 1. For example, $R^{13}$ may be phenyl or benzyl.

In certain preferred embodiments, $R^D$ is hydrogen or $C_{1-6}$-alkyl.

In some such embodiments, the compound has a structure corresponding to Formula (II-A1.2), (II-A2.2), (II-A3.2), (II-A4.2), (II-A5.2), or (II-A6.2):

(II-A1.2)

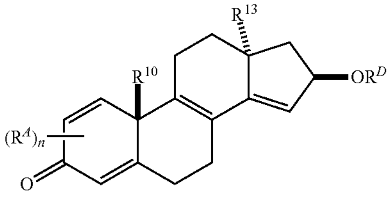

(II-A2.2)

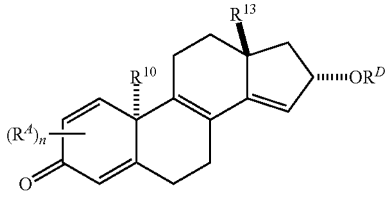

(II-A3.2)

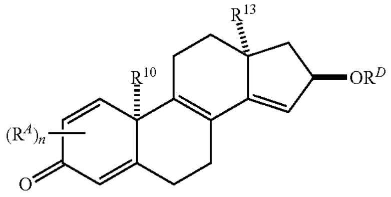

(II-A4.2)

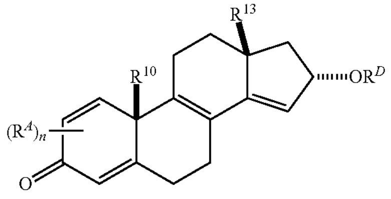

(II-A5.2)

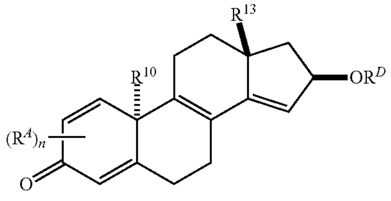

-continued (II-A6.2)

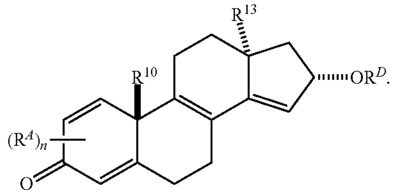

In certain preferred embodiments, n is 1 or 2. In some such preferred embodiments, n is 1. In some such preferred embodiments, n is 2.

In certain preferred embodiments, $R^A$ is $C_{1-10}$-alkyl, such as methyl,

In certain preferred embodiments, $R^{10}$ is $C_{1-10}$-alkyl, $C_{1-10}$-haloalkyl, halogen, or $—(CH_2)_m—C_{6-10}$-aryl. In some such preferred embodiments, $R^{10}$ is halogen. In some such preferred embodiments, $R^{10}$ is $C_{1-10}$-alkyl, such as methyl, ethyl, or propyl. In some such preferred embodiments, $R^{10}$ is $—(CH_2)_m—C_{6-10}$-aryl, wherein m is 0 or 1. For example, $R^{10}$ may be phenyl or benzyl.

In certain preferred embodiments, $R^{13}$ is $C_{1-10}$-alkyl, $C_{1-10}$-haloalkyl, or $—(CH_2)_m—C_{6-10}$-aryl. In some such preferred embodiments, $R^{13}$ is $C_{1-10}$-alkyl, such as methyl, ethyl, or propyl. In some such preferred embodiments, $R^{13}$ is $—(CH_2)_m—C_{6-10}$-aryl, wherein m is 0 or 1. For example, $R^{13}$ may be phenyl or benzyl.

In certain preferred embodiments, $R^D$ is hydrogen or $C_{1-6}$-alkyl.

In certain embodiments, the compound is Compound 100. In certain embodiments, the compound is Compound 101. In certain embodiments both compounds (100 and 101) can be used in combination with each other or other pharmaceutically active agents.

Another aspect of the present disclosure includes a method for treating or preventing schizophrenia in a subject in need of such treatment or prevention.

Still another aspect of the present disclosure includes a method for treating or preventing neurodegeneration in a subject in need of such treatment or prevention. In some such embodiments, the human subject is suffering from or at risk for a neurodegenerative disease such as spinal cord injury (SCI), multiple sclerosis (MS), Parkinson's disease (PD), and Alzheimer's disease (AD).

Yet another aspect of the present disclosure includes a method for treating or preventing neuropathic pain in a subject in need of such treatment or prevention.

One aspect of the present disclosure includes a method for treating or preventing a disease or condition that is at least partially mediated or affected by ERβ in a subject in need of such treatment or prevention.

Another aspect of the present disclosure includes a method for treating or preventing a disease or condition treatable or preventable by selectively modulating ERβ in a subject in need of such treatment or prevention.

In certain embodiments, for any of the aforementioned aspects, the subject is a mammal. In some such embodiments, the mammal is a human.

In certain embodiments, for any of the aforementioned aspects, the methods comprise administering to the subject a therapeutically effective amount of a compound described herein (including, but not limited to, Compound 100 or 101) or a pharmaceutically acceptable salt or prodrug thereof as single agent or in combination with another chemotherapeutic compound. In some such embodiments, the methods comprise administering to the subject a therapeutically effective amount of Compound 100 or a pharmaceutically acceptable salt or prodrug thereof, preferably Compound 100. In other such embodiments, the methods comprise administering to the subject a therapeutically effective amount of Compound 101 or a pharmaceutically acceptable salt or prodrug thereof, preferably Compound 101. In certain embodiments, the compound is administered orally.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). In certain embodiments, dosage unit compositions contain such amounts or submultiples thereof to make up the daily dose. In many instances, the administration of the compound or salt will be repeated a plurality of times. In certain embodiments, multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

The activity of a compound can be determined using various known methods. For example, the anti-proliferative activity of a compound can be determined using various known methods, including in vitro and in vivo antiproliferative assays using cancer cell lines such as U251 and/or U87 (human glioblastoma-derived cell lines), DU-145 (prostate cancer cell line), MDA-MB-231 (human breast adenocarcinoma), AsPC-1 (human pancreas adenocarcinoma ascites metastasis), and A549 (lung carcinoma).

E. COMPOSITIONS

In at least one aspect, the present disclosure includes compositions comprising a compound described herein (including, but not limited to, Compound 100 or 101) or a pharmaceutically acceptable salt or prodrug thereof. In certain embodiments, the composition comprises one or more conventional pharmaceutically acceptable excipients.

In at least one aspect, the present disclosure includes compositions comprising an enantiomeric compound described herein. In certain embodiments, the composition is enantiomerically pure or enriched. For example, the composition may comprise at least 85% of one enantiomer and not more than 15% of the other enantiomer; alternatively, at least 90% of one enantiomer and not more than 10% of the other enantiomer; alternatively, at least 95% of one enantiomer and not more than 5% of the other enantiomer; alternatively, at least 97% of one enantiomer and not more than 3% of the other enantiomer; or alternatively, at least 99% of one enantiomer and not more than 1% of the other enantiomer. In certain embodiments, the composition is substantially free of enantiomeric impurities. In some such embodiments, the composition is free of any detectable amount of an enantiomeric impurity.

Pharmaceutical compositions disclosed herein comprise a compound disclosed herein or a pharmaceutically acceptable salt or prodrug thereof, preferably Compound 100 or Compound 101. In some embodiments, the pharmaceutical composition is an oral dosage form, preferably a solid oral dosage form (e.g., a tablet). In some such embodiments, the solid oral dosage form may comprise pharmaceutically acceptable excipients such as excipients that function as binders, glidants, lubricants, and fillers. Thus, a solid oral dosage form comprising a compound disclosed herein or a pharmaceutically acceptable salt thereof further optionally comprises one or more conventional pharmaceutically acceptable excipients.

In some embodiments, a compound is co-administered with a chemotherapeutic agent. In some such embodiments, the chemotherapeutic agent is an agent used to treat a brain tumor, such as temozolomide (TMZ).

In some embodiments, the chemotherapeutic agent and the compound of the present disclosure are co-administered to the patient in a substantially simultaneous manner (e.g., or within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some embodiments, the chemotherapeutic agent and the compound of the present disclosure are administered in separate pharmaceutical compositions. In some embodiments, the chemotherapeutic agent and the compound of the present disclosure are administered in the same pharmaceutical composition.

In at least one aspect, the present disclosure includes a pharmaceutical composition for treating a brain tumor, the composition comprising a compound disclosed herein or a pharmaceutically acceptable salt thereof and a pharmaceutically acceptable excipient. In certain embodiments, the compound is Compound 100. In certain embodiments, the compound is Compound 101.

It will be readily apparent to those skilled in the art that other suitable modifications and adaptations of the compositions and methods of the invention described herein may be made using suitable equivalents without departing from the scope of the invention or the embodiments disclosed herein.

The compounds, compositions, and methods described herein will be better understood by reference to the following examples, which are included as an illustration of and not a limitation upon the scope of the invention.

F. EXAMPLES

Materials and Methods

All reactions were conducted in flame-dried glassware under a nitrogen atmosphere with dry solvents, unless otherwise noted. All reagents and starting materials were purchased from commercial sources and used as supplied, unless otherwise indicated.

Anhydrous diethyl ether ($Et_2O$), tetrahydrofuran (THF), toluene (PhMe), and methylene chloride ($CH_2Cl_2$) were obtained by a Glass Contour Solvent Purification System. (R)-BINOL and (S)-BINOL were purchased from Chem Impex. Titanium isopropoxide ($Ti(Oi\text{-}Pr)_4$) was purchased from Acros, and distilled before use. Solutions of n-BuLi (2.5 M in hexanes) were purchased from Aldrich and titrated against N-benzylbenzamide. Yields refer to chromatographically purified and isolated products unless otherwise stated. Flash column chromatography was performed on the BIOTAGE® Automated Liquid Chromatography System ISOLERA™ One using BIOTAGE® SNAP KPM Sil 10-100 g silica gel cartridges and BIOTAGE® SNAP HP-Sphere ultra 10-100 g silica gel cartridges. TLC analyses were performed on EMD TLC Silica gel 60 F254 Glass Plates and the spots were visualized by UV-light (254 nm), an aqueous solution of phosphomolybdic acid, ceric sulfate, and sulfuric acid, or a solution of ethanol, surfuric acid, glacial acetic acid, and p-anisaldehyde. $^1H$ NMR data were recorded on Bruker Avance III 500 and 600 MHz spectrometer (TBI probe) with calibration of spectra to residual $CDCl_3$ (7.26 ppm), $CD_3OD$ (3.31 ppm) and $CD_2Cl_2$ (5.32 ppm). $^{13}C$ NMR data were recorded at 125 MHz and 150 MHz on Bruker Avance III 500 and 600 MHz spectrometer (TBI probe) with calibration to the central line of $CDCl_3$ (77.16 ppm), $CD_3OD$ (49.0 ppm) and $CD_2Cl_2$ (53.8 ppm). Infrared spectra were recorded on a JASCO FT/IRM4100 Fourier Transform Infrared Spectrometer. Optical rotations were measured with a JASCO P-2000 polarimeter, and the concentration (c) is reported in g/mL. HRMS (ESI or EI) analyses were performed at the Mass Spectrometry Laboratory of University of Illinois at Urbana-Champaign. All compounds purified by chromatography were sufficiently pure for use in further experiments, unless indicated otherwise. For abbreviations, diisobutylaluminum hydride (DIBAL-H), phenyliodonium diacetate or (diacetoxyiodo) benzene (PIDA), 1,1,1,3,3,3-hexafluoro-2-propanol (HFIP).

Preparation of Intermediates

Synthesis of Enyne 1

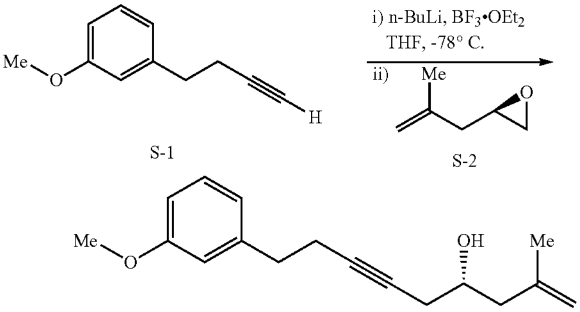

S-1
S-2
1

Enyne 1: To a stirring solution of S-1 (0.30 g, 1.9 mmol, 2.5 equiv) in 5 mL THF at −78° C. under $N_2$ atmosphere was added n-BuLi (2.4 M in hexanes. 0.47 ml, 1.1 mmol, 1.5 equiv) dropwise. The resulting mixture was stirred at the same temperature for 44 min, and then $BF_3{\cdot}OEt_2$ was added dropwise. The mixture was stirred for 33 min, and then a solution of S-2 (74 mg, 0.75 mmol, 1.0 equiv) in 1 ml THF was added dropwise. The mixture was stirred for 39 min, and the reaction was quenched with 5 mL saturated sodium bicarbonate solution at −78° C. The mixture was warmed to rt, diluted with 20 mL ethyl acetate, and the organic layer was separated. The aqueous layer was extracted with 25 mL ethyl acetate. The combined organic layers were dried over $Na_2SO_4$, filtered, and then the filtrate was concentrated in vacuo. $SiO_2$ flash column chromatography afforded 0.14 g of the title compound 1 as a pale yellow oil (74% isolated yield).

Spectral data for 1: $^1H$ NMR (600 MHZ, Chloroform-d) δ7.21 (t, J=7.8 Hz, 1H), 6.81 (d, J=7.9 Hz, 1H), 6.79-6.75 (m, 2H), 4.86 (t, J=1.8 Hz, 1H), 4.81-4.76 (m, 1H), 3.85-3.80 (m, 1H), 3.79 (s, 3H), 2.80 (t, J=7.5 Hz, 2H), 2.49 (tt, J=7.5, 2.4, 2.4 Hz, 2H), 2.40-2.29 (m, 2H), 2.25 (dd, J=14.1, 4.9 Hz, 1H), 2.17 (dd, J=13.8, 8.5 Hz, 1H), 2.01 (d, J=4.0 Hz, 1H), 1.75 (s, 3H); $^{13}C$ NMR (151 MHz, Chloroform-d) δ 159.69, 142.45, 142.42, 129.39, 120.86, 114.39, 113.44, 111.54, 82.32, 77.08, 67.85, 55.17, 44.79, 35.39, 27.24, 22.54, 20.88; IR (thin film): 3452, 2933, 2835, 1602, 1585, 1491, 1452, 1153 $cm^{-1}$; HRMS (ESI-TOF): calculated for $C_{17}H_{23}O_2$ [M+H$^+$] 259.1698. found 259.1702;

$$[\alpha]_D^{23} = -1.7\ (c\ 0.084\ g/mL,\ CHCl_3).$$

Synthesis of Hydrindane 2

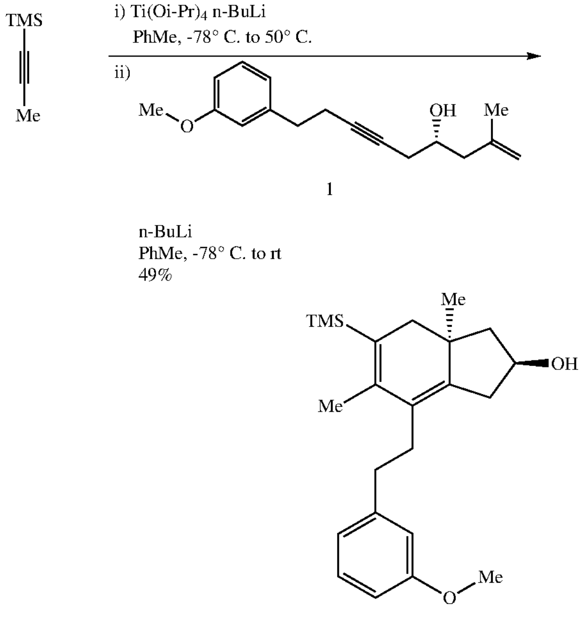

1

2

Hydrindane 2: To a stirring solution of 1-(Trimethylsilyl) propyne (7.8 g, 69 mmol, 3.3 equiv) and $Ti(Oi\text{-}Pr)_4$ (19.8 g, 69.7 mmol, 3.3 equiv) in 350 mL anhydrous toluene at −78° C. under $N_2$ atmosphere was added n-BuLi (2.4 M in hexanes, 58 mL, 140 mmol, 6.5 equiv) dropwise. After the addition, the cooling bath was removed, and the resulting dark brown mixture was warmed to rt, and then further warmed to 50° C. The reaction mixture was stirred for 1 hr at the same temperature without a reflux condenser, and then cooled to rt. A separate round bottom flask charged with a solution of 1 (5.5 g, 21 mmol, 1.0 equiv) in 100 mL anhydrous toluene at −78° C. was added n-BuLi (2.4 M in hexanes, 8.9 mL, 21 mmol, 1.0 equiv) dropwise. The resulting solution was warmed to rt, cannulated into the above dark brown mixture, and then stirred overnight at rt under $N_2$ atmosphere (approx. 12 hr). After this period, 150 mL saturated sodium bicarbonate solution was added to the reaction mixture. The organic layer was separated, and the aqueous layer was extracted with 250 mL×4 diethyl ether. The combined organic layers were dried with $Na_2SO_4$, filtered, and the filtrate was concentrated in vacuo. The crude product was purified by dry column vacuum chromatography using 7 cm×6.5 cm (height×diameter) $SiO_2$ column, and 5% ethyl acetate, 10% ethyl acetate, and 15%-24% (1% gradient/fraction) ethyl acetate in hexanes as the eluent (200 mL/fraction) to afford 3.9 g of the title compound 2 as a thick yellow oil (49% isolated yield).

Spectral Data for 2: $^1H$ NMR (500 MHZ, Chloroform-d) δ7.19 (t, J=7.8 Hz, 1H), 6.77-6.72 (m, 2H), 6.69 (dd, J=2.6, 1.6 Hz, 1H), 4.36 (p, J=6.8 Hz, 1H), 3.79 (s, 3H), 2.69-2.60 (m, 2H), 2.57-2.43 (m, 2H), 2.38-2.30 (m, 1H), 2.17 (d, J=15.8 Hz, 1H), 2.04-1.95 (m, 3H), 1.93 (d, J=2.6 Hz, 3H), 1.39 (dd, J=12.3, 7.7 Hz, 1H), 1.28 (s, 1H), 0.79 (s, 3H), 0.16 (s, 9H); $^{13}C$ NMR (150 MHz, Chloroform-d) δ159.61, 144.48, 143.85, 141.23, 129.28, 129.26, 128.47, 121.31, 114.84, 111.07, 72.05, 55.28, 51.25, 41.57, 39.45, 38.45, 35.72, 31.60, 21.34, 19.18, 0.15; IR (thin film): 3348, 2949, 2857, 1602, 1584, 1454, 1248, 1058, 835 $cm^{-1}$; HRMS (ESI-TOF): calculated for $C_{23}H_{35}O_2Si$ [M+H$^+$] 371.2406. found 371.2393;

$$[\alpha]_D^{22} = -44.0\ (c\ 0.022\ g/mL,\ CHCl_3).$$

Example 1-1

Compound 100—(9S,13R,16S)-9,13-dimethyl-7,9,11,12,13,15,16,17-octahydro-6H-cyclopenta[a]phenanthrene-3,16-diol

Compound 101—(9R,13S,16R)-9,13-dimethyl-7,9,11,12,13,15,16,17-octahydro-6H-cyclopenta[a]phenanthrene-3,16-diol Compound 100

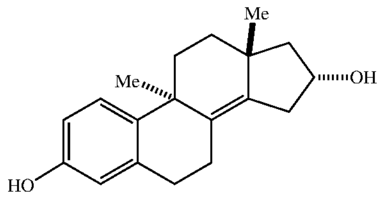

Compound 101

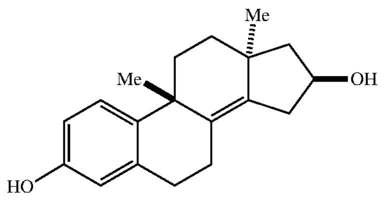

Compounds 100 and 101 are enantiomers—mirror images of one another.

Compound 100 was prepared in 3 steps from the enantiomer of ent-Enyne 1, which is available in just 3 steps from epichlorohydrin.

Preparation of Compound 100 from ent-Enyne 1

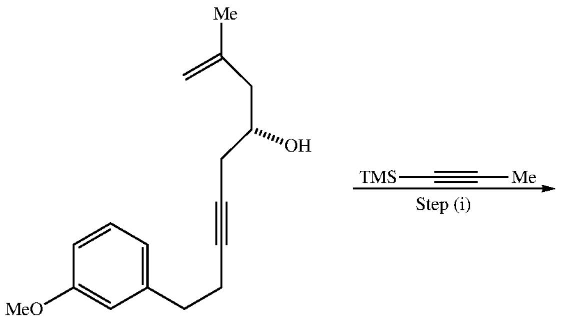

ent-Enyne 1

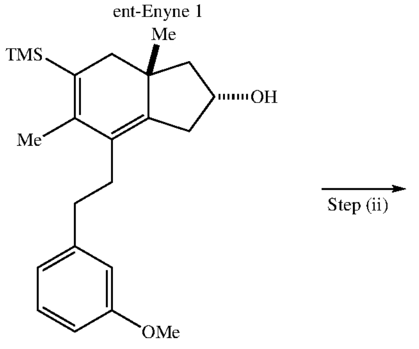

ent-Hydrindane 2

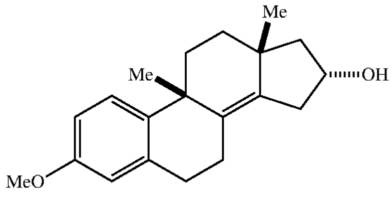

Steroid 3

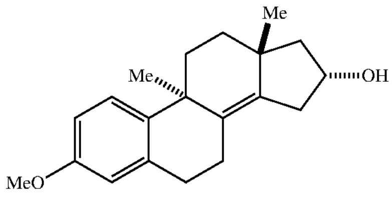

Steroid 4

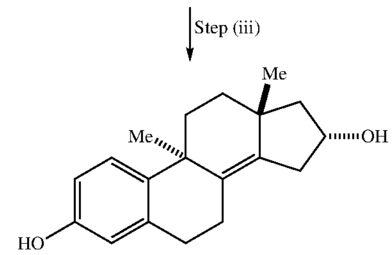

Compound 100

The first step was a titanium-mediated annulation reaction as generally described above to provide the stereodefined ent-Hydrindane 2.

In the second step, ent-Hydrindane 2, which is a silyl-substituted diene, can be reacted with (R)-Binol or (S)-Binol and $SnCl_4$ at −78° C. to deliver tetracyclic steroid products 3 and 4. These are examples of matched and mismatched double asymmetric reaction processes; the matched double asymmetric reaction proceeds with much higher levels of stereoselectivity than the mismatched double asymmetric reaction.

Matched Double Asymmetric Reaction for Cyclization of ent-Hydrindane 2: To a stirring suspension of (R)-Binol (10.7 g, 37.4 mmol, 1.2 equiv) in 200 mL of dichloromethane at −78° C. under $N_2$ atmosphere was added a solution of $SnCl_4$ (1.0 M in dichloromethane, 31 mL, 31 mmol, 1.0 equiv) dropwise using a syringe. The resulting mixture was stirred for 23 min at −78° C. and then a solution of ent-Hydrindane 2 (11.5 g, 31 mmol, 1.0 equiv) in 80 mL of dichloromethane was added dropwise then stirred at −78° C. for 1 hr and then warmed to rt. The reaction was then quenched by the addition of 400 mL sat. aqueous ammonium chloride, and the resulting mixture was stirred for 40 min. The organic layer was separated and extracted with dichloromethane. The combined organic layers were dried over $Na_2SO_4$, filtered, and the resulting filtrate was concentrated in vacuo (analyses of crude material from this matched double asymmetric reaction process typically reveal ds for the cyclization to be ≥20:1). Purification of the crude product by $SiO_2$ flash column chromatography afforded 6.6 g of Steroid 4 (71% isolated yield). Mismatched Double Asymmetric Reaction for Cyclization of ent-Hydrindane 2: To a stirring suspension of (S)-BINOL (16 g, 56 mmol, 1.2 equiv) in 280 mL dichloromethane at −78° C. under $N_2$ atmosphere was added a solution of $SnCl_4$ (1.0 M in dichloromethane, 56 mL, 56 mmol, 1.2 equiv) dropwise using syringe. The resulting mixture was stirred for 25 min at −78° C., and then a solution of ent-Hydrindane 2 (17 g, 46 mmol, 1.0 equiv) in 230 mL dichloromethane was added dropwise over 1 hr via cannula. The resulting mixture was stirred for 2 hr at −78° C., and then warmed to rt. The reaction was judged to be complete by TLC-analysis. 500 mL saturated solution of $NaHCO_3$ was added, stirred vigorously for 3 hr. The organic layer was separated, and the aqueous layer was extracted with 300 mL×3 DCM. The combined organic layers were dried over $MgSO_4$, filtered, and the filtrate was concentrated in vacuo. The crude product was obtained as a 1.3:1 mixture of Steroid 3 and Steroid 4. A subsequent purification by $SiO_2$ flash column chromatography afforded 5.4 g of Steroid 3 (39% isolated yield, 61% combined yield of Steroid 3 and Steroid 4) as yellow solid.

Spectral data for Steroid 3: $^1H$ NMR (600 MHZ, Chloroform-d) δ7.25 (d, J=8.7 Hz, 1H), 6.72 (dd, J=8.7, 2.9 Hz, 1H), 6.57 (d, J=2.7 Hz, 1H), 4.62-4.48 (m, 1H), 3.77 (s, 3H), 2.90-2.81 (m, 3H), 2.46 (dt, J=13.3, 4.5 Hz, 1H), 2.42-2.34 (m, 1H), 2.29 (dd, J=16.7, 5.1 Hz, 1H), 2.23 (ddd, J=14.3, 5.6, 3.5 Hz, 1H), 2.02 (dd, J=12.1, 6.5 Hz, 1H), 1.91 (ddd, J=14.7, 12.3, 3.6 Hz, 1H), 1.57 (ddd, J=12.9, 5.6, 3.5 Hz, 1H), 1.39 (s, 1H), 1.33 (s, 3H), 1.30-1.23 (m, 2H), 1.05 (s, 3H). $^{13}C$ NMR (150 MHz, Chloroform-d) δ157.3, 138.9, 138.6, 137.1, 133.6, 126.4, 113.6, 112.1, 71.1, 55.3, 51.5, 41.3, 39.1, 38.1, 34.4, 34.2, 33.0, 31.9, 25.9, 24.9; IR (thin film): 3320, 2954, 2912, 2846, 1598, 1482, 1447, 1270, 1240, 1037 $cm^{-1}$; HRMS (ESI-TOF): calculated for $C_{20}H_{27}O_2$ $[M+H]^+$299.2013. found 299.2011;

$$[\alpha]_D^{22} = -117.2\ (c\ 0.0086,\ CHCl_3).$$

In the third step, demethylation was performed using DIBAL to provide Compound 100.

Compound 101 was prepared in an identical manner, except beginning with Enyne 1 (also readily available from epichlorohydrin).

Preparation of Compound 101 from Enyne 1

The first step was a titanium-mediated annulation reaction as generally described above to provide the stereodefined Hydrindane 2.

In the second step, Hydrindane 2, which is a silyl-substituted diene, was reacted with (R)- or (S)-Binol and $SnCl_4$; as discussed previously with ent-Hydrindane 2, these reactions are also mismatched and matched double asymmetric processes. Overall, independent of which Binol isomer is used, this chemical reaction induces a protodesilylation of the diene, followed by an intramolecular Friedel-Crafts alkylation to deliver tetracyclic Steroids 5 and 6.

Mismatched Double Asymmetric Reaction for Cyclization of Hydrindane 2:

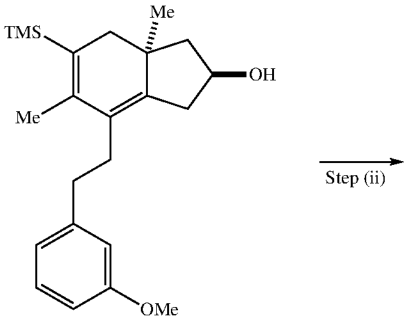

Hydrindane 2

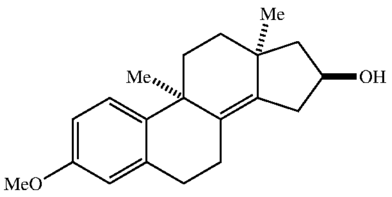

Steroid 5

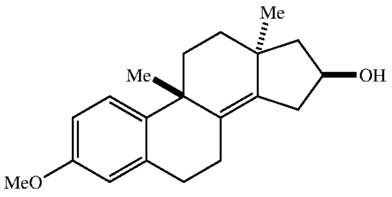

Steroid 6

To a stirring suspension of (R)-BINOL (1.0 g, 3.6 mmol, 5.4 equiv) in 36 mL dichloromethane at −78° C. under $N_2$ atmosphere was added a solution of $SnCl_4$ (1.0 M in dichloromethane, 3.6 mL, 3.6 mmol, 5.4 equiv) dropwise using syringe. The resulting mixture was stirred for 21 min at −78° C., and then a solution of Hydrindane 2 (0.25 g, 0.68 mmol, 1.0 equiv) in 13 mL dichloromethane was added dropwise over 3 min via syringe. The resulting mixture was stirred for 1 hr 45 min at −78° C., and then warmed to rt over 8 min. The reaction was judged to be complete by TLC-analysis. 50 mL saturated sodium bicarbonate solution was added, stirred for 18 min, and then further diluted with 100 ml dichloromethane. The organic layer was separated, and the aqueous layer was extracted with 100 mL×2 dichloromethane. The combined organic layers were dried over $Na_2SO_4$, filtered, and the filtrate was concentrated in vacuo. The crude product was obtained as a 1:1.2 mixture of Steroid 5 and Steroid 6. A subsequent purification by $SiO_2$ flash column chromatography afforded 40 mg of compound 5 as a thick yellow film (20% isolated yield), and 71 mg of 4:1 mixture of 5 and 6 as a thick yellow film (36% isolated yield, 56% combined yield of 5 and 6).

Spectral data for 5: $^1$H NMR (500 MHZ, Methylene Chloride-$d_2$) δ7.24 (d, J=8.7 Hz, 1H), 6.70 (dd, J=8.7, 2.9 Hz, 1H), 6.56 (d, J=2.9 Hz, 1H), 4.56-4.47 (m, 1H), 3.74 (s, 3H), 2.86-2.78 (m, 3H), 2.50-2.42 (m, 1H), 2.41-2.32 (m, 1H), 2.29-2.18 (m, 2H), 1.99 (dd, J=12.0, 6.5 Hz, 1H), 1.91 (ddd, J=14.2, 12.3, 3.5 Hz, 1H), 1.57 (ddd, J=12.8, 5.6, 3.5 Hz, 1H), 1.44 (d, J=5.3 Hz, 1H), 1.31 (s, 3H), 1.25-1.17 (m, 2H), 1.04 (s, 3H); $^{13}$C NMR (151 MHZ, Chloroform-d) δ157.27, 138.94, 138.61, 137.06, 133.61, 126.42, 113.62, 112.11, 71.13, 55.28, 51.49, 41.33, 39.08, 38.10, 34.38, 34.17, 32.99, 31.88, 25.94, 24.87; IR (thin film): 3335, 2950, 2919, 2861, 1607, 1497, 1451, 1272, 1231, 1039 $cm^{-1}$; HRMS (EI-TOF): calculated for $C_{20}H_{26}O_2$ [M+] 298.1933. found 298.1938;

$$[\alpha]_D^{23} = +139.7\ (c\ 0.0065\ \text{g/mL},\ \text{CHCl}_3).$$

Matched Double Asymmetric Reaction for Cyclization of Hydrindane 2:

To a stirring suspension of (S)-BINOL (12.5 g, 43.7 mmol, 5.31 equiv) in 450 mL dichloromethane at −78° C. under $N_2$ atmosphere was added a solution of $SnCl_4$ (1.0 M in dichloromethane, 44 mL, 44 mmol, 5.4 equiv) dropwise using syringe. (At room temperature, (S)-BINOL was fully dissolved in dichloromethane. The suspension was observed when the solution was cooled to −78° C.) The resulting mixture was stirred for 18 min at −78° C., and then a solution of Hydrindane 2 (3.05 g, 8.23 mmol, 1 equiv) in 150 mL dichloromethane was added dropwise over 1 hr 20 min via cannula transfer. The resulting mixture was stirred for an additional 1 hr at −78° C., and then warmed to rt over 52 min. The reaction was judged to be complete by TLC-analysis. A 100 mL saturated sodium bicarbonate solution was added, and the resulting mixture was further diluted with 200 mL dichloromethane. The organic layer was separated, and the aqueous layer was extracted with 500 mL×2 ethyl acetate. The combined organic layers were dried over $Na_2SO_4$, filtered, and the filtrate was concentrated in vacuo. The crude product (formed with typically very high levels of stereoselection; ds≥20:1) was purified by dry column vacuum chromatography using 7 cm×6.5 cm (height× diameter) $SiO_2$ column, and 1% ethyl acetate-10% ethyl acetate (1% gradient/fraction) in dichloromethane as the eluent (200 mL/fraction) to afford 1.22 g of the Steroid 6 as a thick yellow oil (50% isolated yield).

Spectral Data for 6 $^1$H NMR (500 MHZ, Chloroform-d) δ7.21 (d, J=8.7 Hz, 1H), 6.76 (dd, J=8.7, 2.6 Hz, 1H), 6.58 (d, J=2.8 Hz, 1H), 4.65-4.56 (m, 1H), 3.78 (s, 3H), 2.90-2.81 (m, 2H), 2.72 (dddt, J=16.1, 12.2, 6.0, 1.1 Hz, 1H), 2.46-2.32 (m, 2H), 2.27 (dd, J=16.8, 4.2 Hz, 1H), 2.17 (dd, J=12.0, 6.7 Hz, 1H), 2.09 (dt, J=13.1, 3.3 Hz, 1H), 1.88-1.80 (m, 1H), 1.76-1.68 (m, 2H), 1.58 (s, 1H), 1.38-1.30 (m, 4H), 0.90 (s, 3H); $^{13}$C NMR (150 MHz, Chloroform-d) δ157.1, 140.1, 137.3, 136.4, 132.0, 127.3, 113.1, 112.5, 71.6, 55.3, 52.0, 41.6, 38.1, 37.7, 34.4, 33.4, 32.3, 31.4, 25.9, 25.0; IR (thin film): 3375, 2933, 2853, 1608, 1498, 1273, 1233, 1035, 732 $cm^{-1}$; HRMS (ESI-TOF): calculated for $C_{20}H_{27}O_2$ [M+$H^+$] 299.2011. found 299.2012;

$$[\alpha]_D^{22} = -223.0\ (c\ 0.014,\ CHCl_3).$$

When (R)-Binol is used to induce the cyclization of Hydrindane 2, an equimolar ratio of the diasteromeric tetracycles results in ~60% yield (dr~1:1), but when (S)-Binol is employed this reaction proceeds to deliver the diastereomer 6 with very high levels of diastereoselection (dr≥20:1).

In the third step, demethylation was performed using DIBAL to provide Compound 101.

To a stirring solution of Steroid 6 (0.17 g, 0.57 mmol, 1 equiv) in 5 mL anhydrous toluene at rt under $N_2$ atmosphere was added DIBAL-H (1.0 M in hexanes, 5.7 mL, 5.7 mmol, 10 equiv). The resulting mixture was warmed to 100° C., refluxed overnight (approx. 20 hr), and then cooled to rt. Small chunks of ice was slowly added, and the resulting mixture was acidified with 3M aqueous hydrochloric acid (3 mL). The organic layer was separated, and the aqueous layer was extracted with 50 mL×3 ethyl acetate. The combined organic layers were dried over $Na_2SO_4$, filtered, and then the filtrate was concentrated in vacuo. The crude product was purified with $SiO_2$ flash column chromatography to afford 0.15 g of Compound 101 as an amorphous white solid (94% isolated yield).

Compounds 100 and 101 possess a quaternary center at $C_9$ and an unsaturation between $C_8$ and $C_{14}$. Compound 101 possesses "unnatural" absolute stereochemistry (relative to estradiol, referring to the absolute stereochemistry at C13).

Compounds 100 and 101 were evaluated for their functional activity at estrogen receptors (both ERα and ERβ). 17β-estradiol was used as a control, as it is appreciated to be a potent agonist of both ERα and ERβ.

As illustrated in FIG. 1, the enantiomeric tetracycles Compound 100 and Compound 101 were found to be impressive agonists of ERβ.

Compound 100 is a uniquely selective and highly potent full agonist of ERβ with an $EC_{50}$ of 0.05 nM, and substantial selectivity (~>260-fold) over ERα (relative to 17β-estradiol; with the assumption that 17β-estradiol is not thought to have significant selectivity in agonizing either ER).

Compound 101 is a partial agonist of ERβ with an $EC_{50}$ value of 1.9 nM, and ~6-fold selectivity over ERα (relative to 17β-estradiol).

Example 1-2

Compound 102—(9R,13S,16R)-3-methoxy-4,9,13-trimethyl-7,9,11,12,13, 15, 16, 17-octahydro-6H-cyclopenta[a]phenanthren-16-ol Compound 103—(9S,13S,16R)-3-methoxy-4,9,13-trimethyl-7,9,11,12,13,15,16,17-octahydro-6H-cyclopenta[a]phenanthren-16-ol Compounds 102 and 103 were prepared as above, except beginning with Enyne 7.

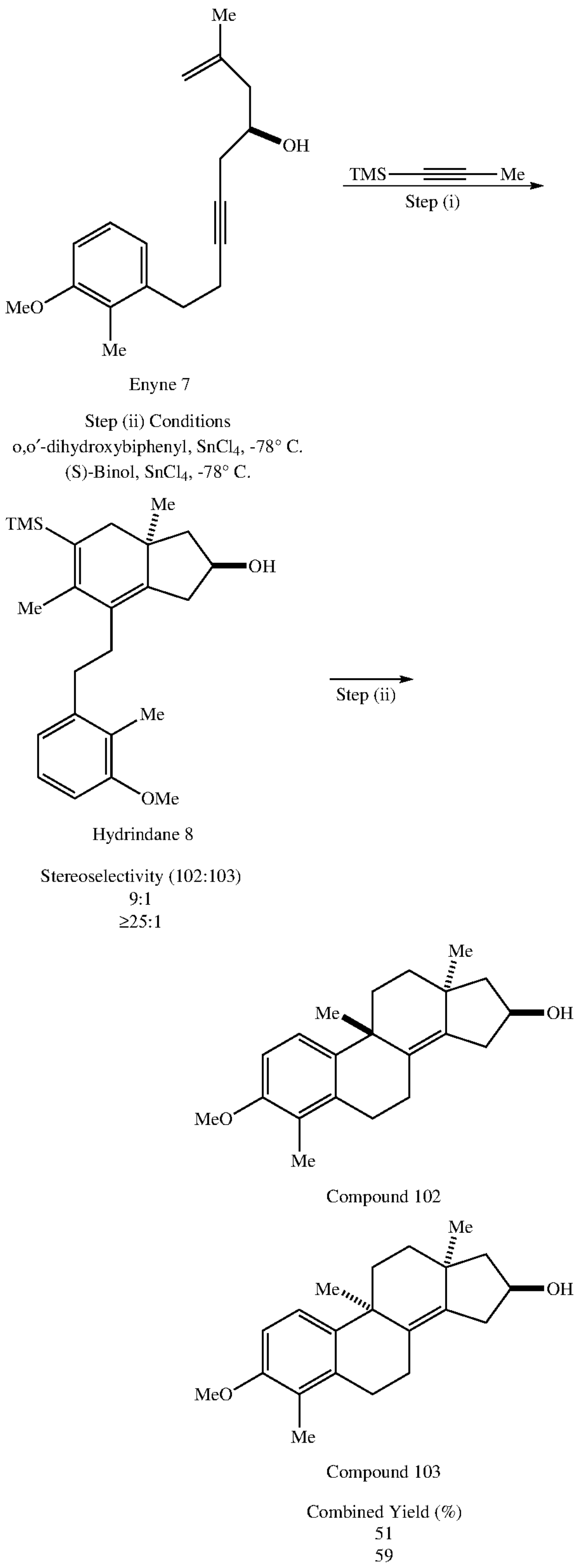 [SMILES: C=C(C)C[C@@H](O)CC#CCCc1cccc(OC)c1C ; CC#C[Si](C)(C)C ; COc1cccc(CCC2=C3C[C@H](O)C[C@]3(C)CC([Si](C)(C)C)=C2C)c1C ; COc1ccc2c(c1C)CCC1=C3C[C@H](O)C[C@]3(C)CC[C@]12C ; COc1ccc2c(c1C)CCC1=C3C[C@H](O)C[C@]3(C)CC[C@@]12C]

Enyne 7 was synthesized from Epoxide 7a and Alkyne 7b as shown below:

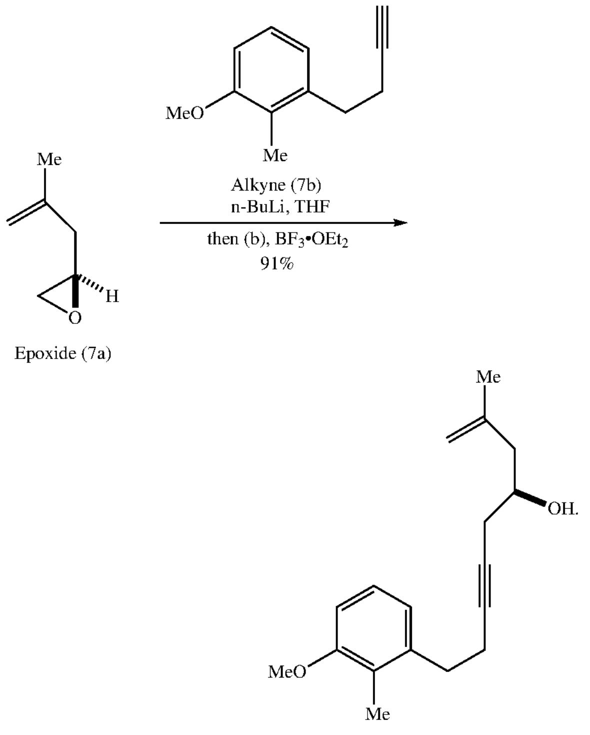

Epoxide (7a)

Enyne 7

Enyne 7: To a stirring solution of Alkyne (7b) (5.4 g, 31 mmol, 2.0 equiv) in 90 mL THF at −78° C. under $N_2$ atmosphere was added n-BuLi (2.5 M in hexanes, 10 mL, 25 mmol, 1.6 equiv) dropwise over 3 min, and the resulting mixture was stirred for 30 min at the same temperature. After the specified period of time, $BF_3{\cdot}OEt_2$ (4.0 g, 28 mmol, 1.8 equiv) was added dropwise to the reaction mixture followed by Epoxide (7a) (1.5 g, 15 mmol, 1.0 equiv). The resulting mixture was stirred at −78° C. under $N_2$ atmosphere for 55 min, and then quenched with 50 mL saturated solution of $NaHCO_3$ at the same temperature. The resulting biphasic solution was warmed to rt, and then further diluted with 50 mL ethyl acetate. The organic layer was separated, dried over $Na_2SO_4$, filtered, and then the filtrate was concentrated in vacuo. $SiO_2$ flash column chromatography afforded the title Enyne 7 as a clear oil (3.9 g, 91%); Spectral Data for Enyne 7: $^1$HNMR (600 MHZ, Chloroform-d): δ7.13 (t, J=7.9 Hz, 1H), 6.85 (d, J=1.1 Hz, 1H), 6.76 (d, J=1.1 Hz, 1H), 4.92-4.86 (m, 1H), 4.86-4.80 (m, 1H), 3.89-3.84 (m, 1H), 3.83 (s, 3H), 2.87 (t, J=7.7 Hz, 2H), 2.47 (tt, J=7.6, 2.4 Hz, 2H), 2.43-2.33 (m, 2H), 2.29 (ddd, J=13.9, 4.9, 1.2 Hz, 1H), 2.25-2.18 (m, 4H), 2.16 (s, 1H), 1.79 (s, 3H); $^{13}$C NMR (150 MHz, Chloroform-d): δ157.7, 142.4, 140.1, 126.0, 124.5, 121.4, 113.3, 108.3, 82.3, 76.8, 67.8, 55.4, 44.7, 32.9, 27.2, 22.5, 19.8, 11.2; IR (thin film): 3441, 2933, 2835, 1585, 1463, 1439, 1258, 1101 $cm^{-1}$; HRMS (ESI-TOF) calculated for $C_{18}H_{25}O_2$ $[M+H]^+$ 273.1855. found 273.1855;

$$[\alpha]_D^{22} = -1.1\ (c\ 0.05,\ CHCl_3).$$

Hydrindane 8: To a stirring solution of 1-(trimethylsilyl) propyne (4.5 g, 40 mmol, 3.1 equiv) and $Ti(Oi\text{-}Pr)_4$ (11 g, 38 mmol, 3.0 equiv) in 200 mL anhydrous toluene at −78° C. under $N_2$ atmosphere was added n-BuLi (2.3 M in hexanes, 33 mL, 76 mmol, 5.9 equiv) dropwise. After the addition, the cooling bath was removed, and the resulting dark brown mixture was warmed to rt, and then further warmed to 50° C. The reaction mixture was stirred for 50 min at the same temperature without a reflux condenser, and then cooled to rt. A separate round bottom flask charged with a solution of Enyne 7 (3.5 g, 13 mmol, 1.0 equiv) in 50 mL anhydrous toluene at −78° C. under $N_2$ atmosphere was added n-BuLi (2.3 M in hexanes, 5.5 mL, 13 mmol, 1.0 equiv) dropwise. The resulting solution was warmed to rt, cannulated into the above dark brown mixture, and then stirred overnight at rt under $N_2$ atmosphere (approx. 12 hr). After this period, 100 ml saturated solution of $NH_4Cl$ was added, and the mixture was further diluted with 100 mL ethyl acetate. The organic layer was separated, and the aqueous layer was extracted with 250 ml×2 ethyl acetate. The combined organic layers were dried with $Na_2SO_4$, filtered, and the filtrate was concentrated in vacuo. $SiO_2$ flash column chromatography afforded the title Hydrindane 8 as a yellow oil (2.6 g, 53% isolated yield); Spectral Data for Hydrindane 8: $^1$H NMR (500 MHZ, Chloroform-d): δ7.07 (t, J=7.9 Hz, 1H), 6.71 (d, J=7.9 Hz, 2H), 4.41-4.31 (m, 1H), 3.81 (s, 3H), 2.73-2.62 (m, 2H), 2.57 (dt, J=13.5, 8.0 Hz, 1H), 2.44-2.37 (m, 1H), 2.35-2.27 (m, 1H), 2.20 (s, 3H), 2.16 (d, J=15.5 Hz, 1H), 2.05-1.97 (m, 3H), 1.95 (app d, J=2.7 Hz, 3H), 1.40 (dd, J=12.4, 7.5 Hz, 1H), 1.20 (s, 1H), 0.79 (s, 3H), 0.16 (s, 9H); $^{13}$C NMR (150 MHz, Chloroform-d): δ157.8, 144.4, 141.8, 141.3, 129.5, 128.5, 126.0, 124.8, 122.3, 108.0, 72.1, 55.7, 51.3, 41.6, 39.4, 38.5, 33.2, 30.5, 21.4, 19.2, 11.4, 0.2; IR (thin film): 3349, 2950, 1585, 1465, 14371102, 1063, 1063, 835 $cm^{-1}$; HRMS (ESI-TOF): calculated for $C_{24}H_{37}O_2Si$ $[M+H]^+$385.2563. found 385.2563;

$$[\alpha]_D^{22} = -39.3\ (c\ 0.014,\ CHCl_3).$$

Example 1-3

Compound 104—(9R,13S,16R)-3,16-dimethoxy-4, 9,13-trimethyl-7,9,11, 12, 13, 15, 16,17-octahydro-6H-cyclopenta[a]phenanthrene

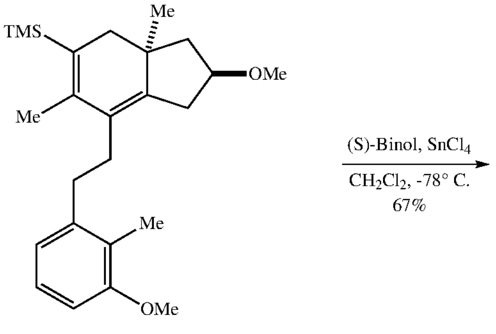

Hydrindane 9

-continued

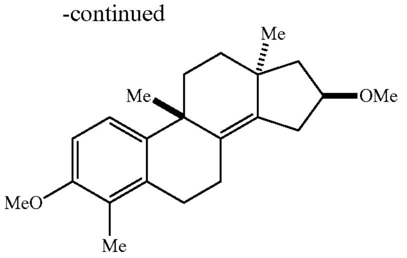

Compound 104

Following the procedures outlined herein, Hydrindane 9 (C16 methyl ether) was smoothly converted to a stereodefined tetracycle (Compound 104) in 67% yield, and with exquisite levels of stereocontrol (ds≥20:1), demonstrating that the C16 (D-ring) alcohol is not required for stereocontrol in the acid mediated cyclization reaction.

Example 1-4

General Procedure for Synthesis of A-Ring Aromatic Tetracycles: Metallacycle-mediated annulative cross-coupling, followed by double asymmetric Brønstead acid-mediated Friedel-Crafts cyclization and demethylation.

Annulative Cross-Coupling: Activation of the TMS-alkyne—To a flask containing TMS-alkyne (3.3 equiv.) in anhydrous toluene (0.3 M) at room temperature was added $Ti(Oi\text{-}Pr)_4$ (3.3 equiv.). The flask was cooled to −78° C., and n-BuLi (2.5 M in hexanes, 6.5 equiv.) was added dropwise. After the addition of n-BuLi was complete, the flask was warmed to room temperature, and then heated to 50° C. for 1 hr. After the indicated time, the flask was re-cooled to room temperature.

Meanwhile, n-BuLi (2.5 M in hexanes, 1.0 equiv.) was added to a precooled separate flask (cooled in −78° C. dry ice/acetone bath) containing a solution of enyne S10 (1.0 g, 1.0 equiv.) in anhydrous toluene (0.3 M). The resulting solution of lithium-alkoxide (at rt) was transferred via cannula to the solution resulting from the procedure above ("activation of the TMS-alkyne"). The resulting mixture was stirred, with gradual warming to room temperature overnight (approximately 15 hr). The reaction was then quenched by the addition of benzaldehyde (3.3 equiv.) followed by introduction of a saturated aqueous solution of $NaHCO_3$ (~one third of total volume of the reaction mixture). The aqueous and organic layers were separated, and the aqueous layer was extracted with ethyl acetate (×3). The combined organic layers were dried over anhydrous $Na_2SO_4$, filtered and concentrated in vacuo to afford a crude

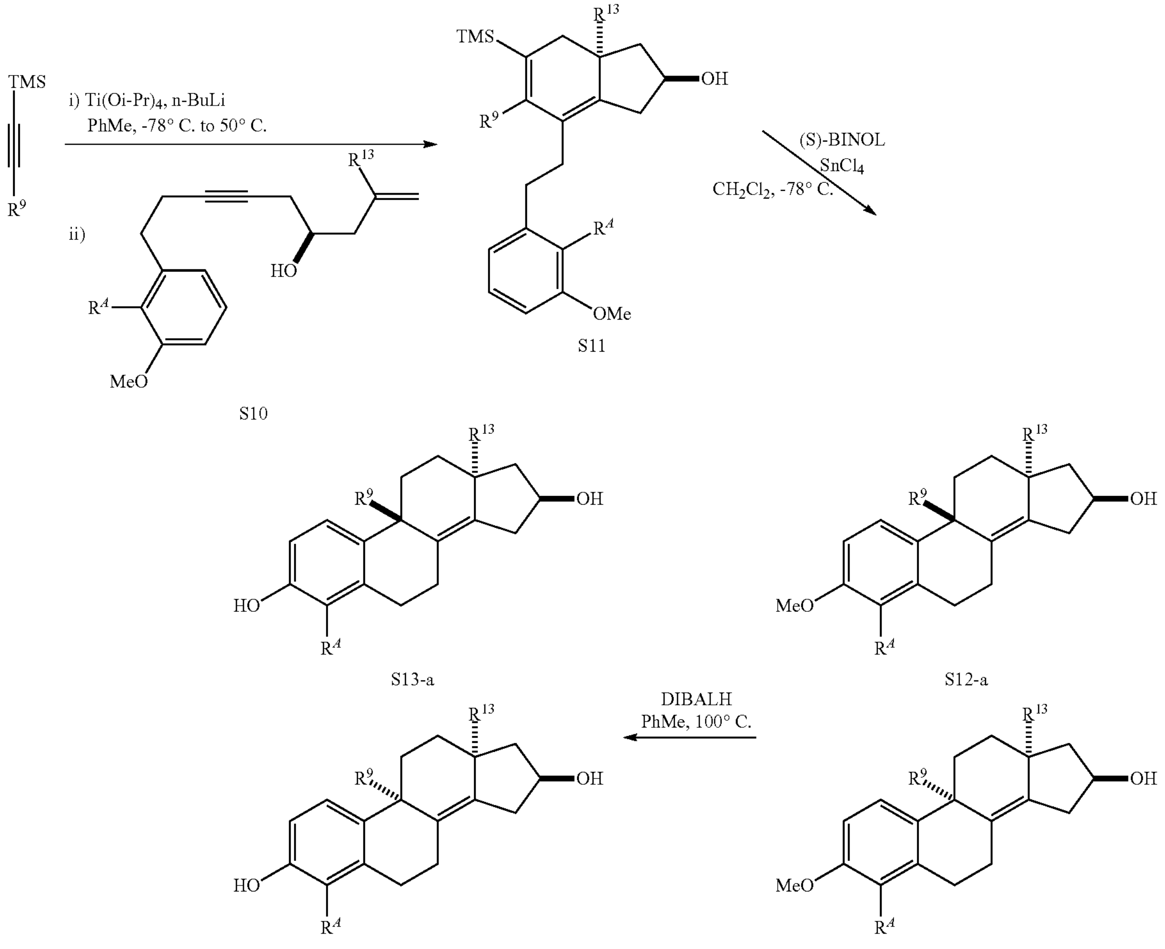

S10 S11 S12-a S13-a S12-s S13-s product, which was purified by flash column chromatography on silica gel with 90:10 to 50:50 hexanes-ethyl acetate gradient elution to afford the hydrindane S11.

Double Asymmetric Friedel-Crafts Cyclization: To a stirring solution of (R)- or (S)-Binol (1.2 equiv.) in $CH_2Cl_2$ (0.16 M) at −78° C. was added a solution of $SnCl_4$ (1.0 M in $CH_2Cl_2$, 1.0 equiv.) dropwise. The resulting mixture was stirred for approximately 30 min. at −78° C., and then a solution of the hydrindane S11 (1.0 equiv.) in $CH_2Cl_2$ (0.16 M) was added dropwise. The resulting mixture was stirred for approximately 1 hr at −78° C., and then warmed up to room temperature over another 1 hr. The reaction was then quenched by the addition of a saturated aqueous solution of $NH_4Cl$, and the resulting mixture was stirred vigorously for 30 mins. The aqueous and organic layers were separated, and the aqueous layer was extracted with $CH_2Cl_2$ (×3). The combined organic layers were washed with a 5% aqueous solution of NaOH, dried over anhydrous $Na_2SO_4$, filtered and concentrated in vacuo to afford crude product containing S12-a and S12-s, which was used in the subsequent step without further purification. The ration of these products varies as a function of substrate structure and absolute stereochemistry of the Binol used.

Demethylation: To a stirring solution of tetracycle S12-a and S-12-s (1.0 equiv.) in anhydrous toluene (0.1 M) at room temperature was added DIBAL-H (1.2 M in hexanes, 10 equiv.). The reaction mixture was warmed with a 100° C. oil bath, refluxed overnight, and then cooled to room temperature. The next morning, small chunks of ice were slowly added, and the resulting mixture was diluted with DI water, 1.0 M solution of HCl and ethyl acetate. The organic layer was separated, dried over anhydrous $Na_2SO_4$, filtered and concentrated in vacuo to afford crude product, which was purified by flash column chromatography on silica gel with 90:10 to 50:50 hexanes-ethyl acetate gradient elution to afford the phenols S13-a and S13-s.

The following exemplary Compounds 105-162 were synthesized following the General Procedure described above:

Compound 105

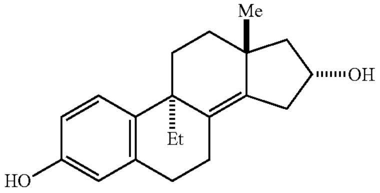

Compound 106

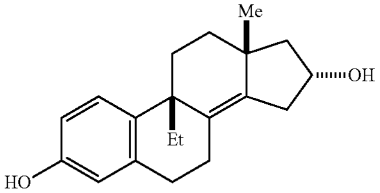

Compound 107

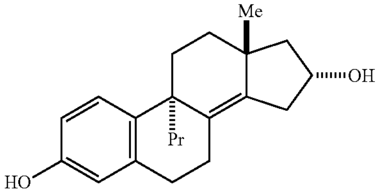

-continued

Compound 108

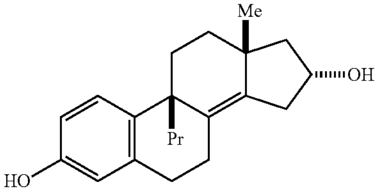

Compound 109

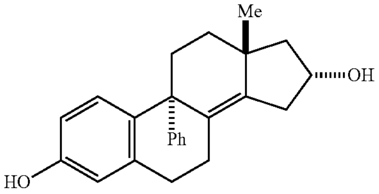

Compound 110

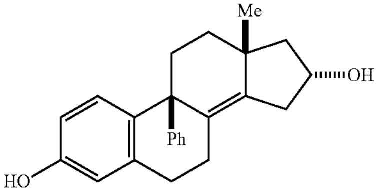

Compound 111

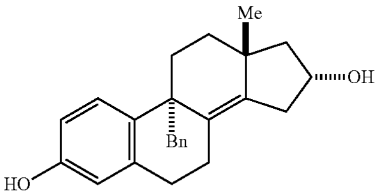

Compound 112

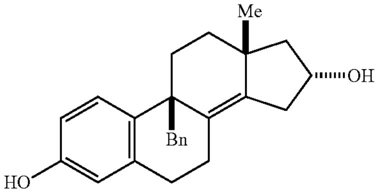

Compound 113

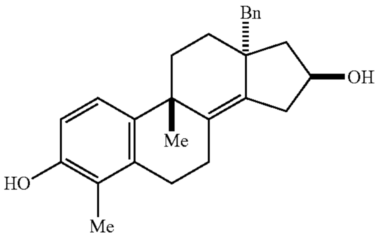

Compound 114

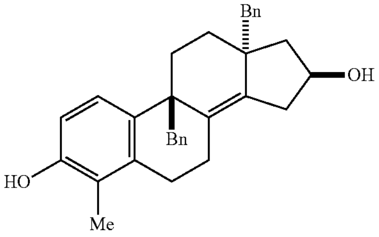

-continued
Compound 115
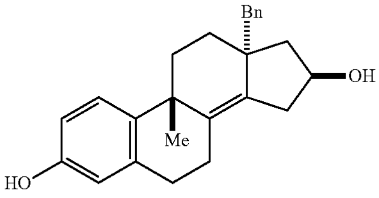
Compound 116
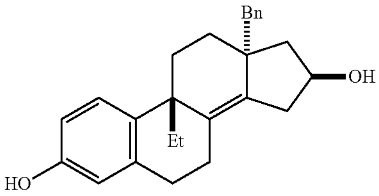
Compound 117
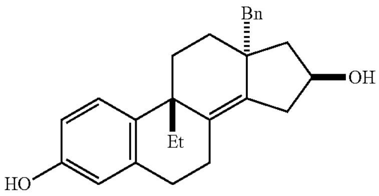
Compound 118
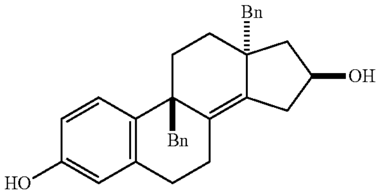
Compound 119
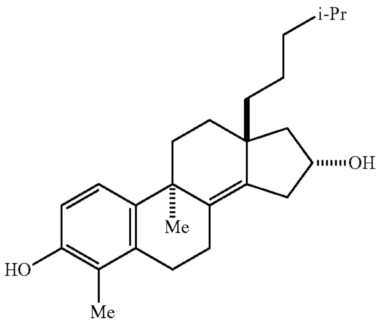
Compound 120
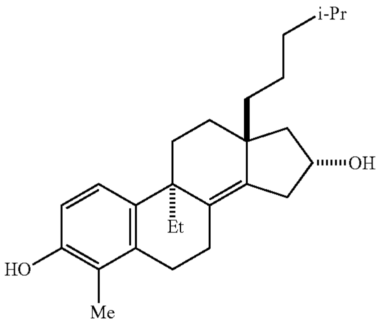
-continued
Compound 121
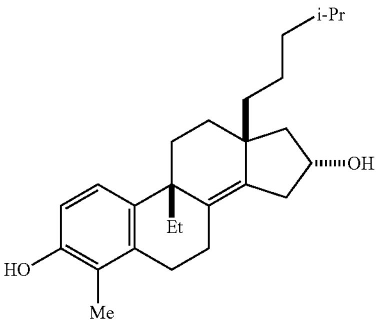
Compound 122
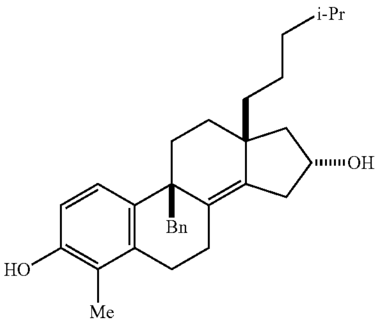
Compound 123
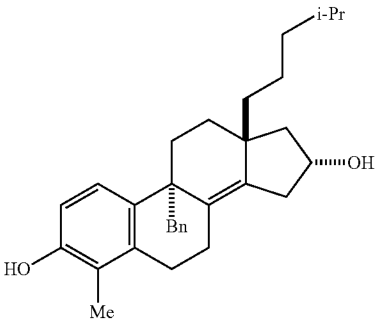
Compound 124
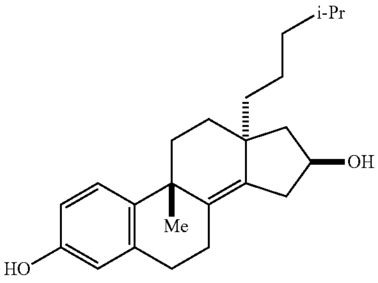
Compound 125
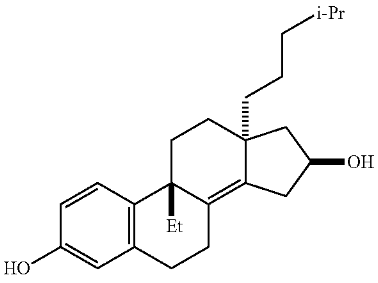

-continued
Compound 126
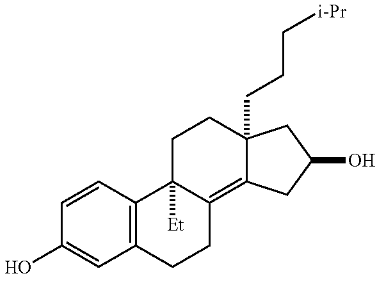
Compound 127
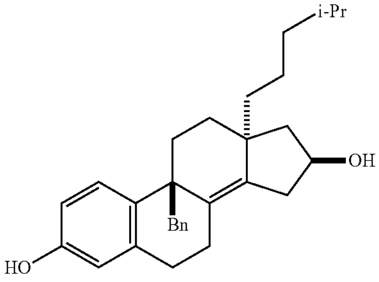
Compound 128
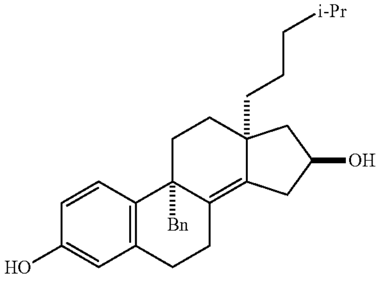
Compound 129
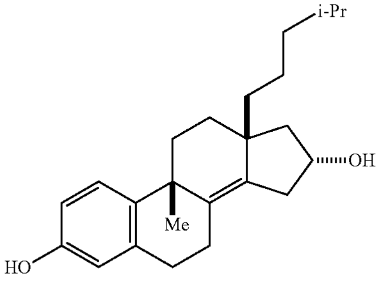
Compound 130
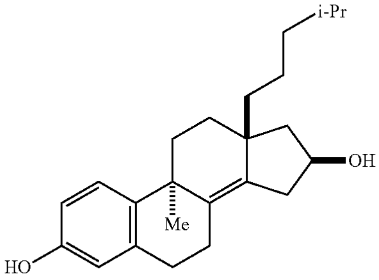
Compound 131
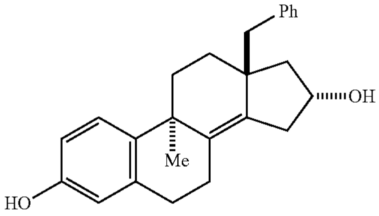
-continued
Compound 132
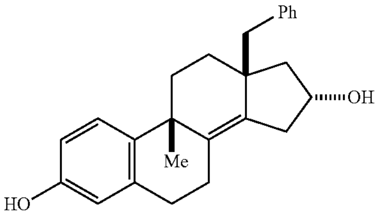
Compound 133
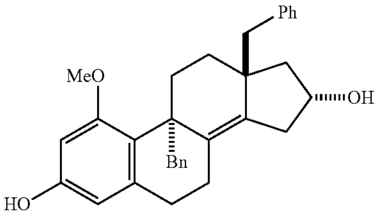
Compound 134
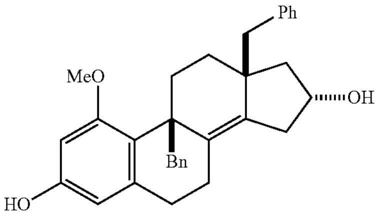
Compound 135
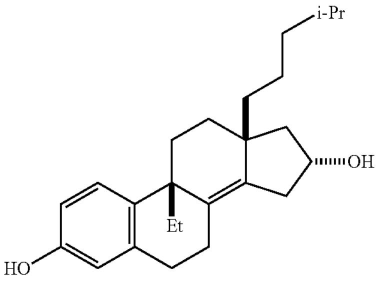
Compound 136
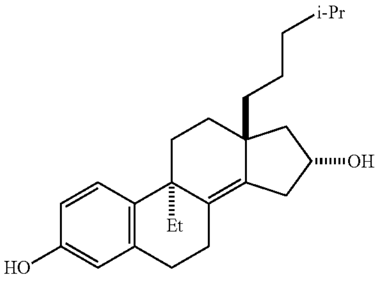
Compound 137
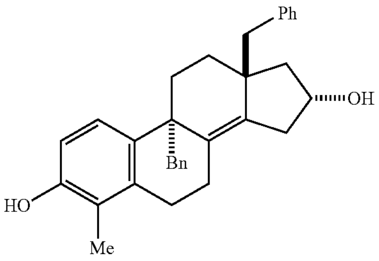

-continued
Compound 138
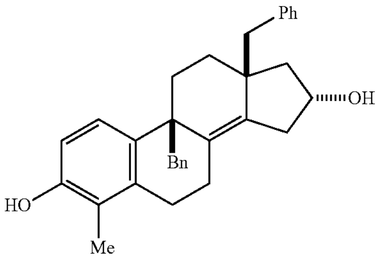
Compound 139
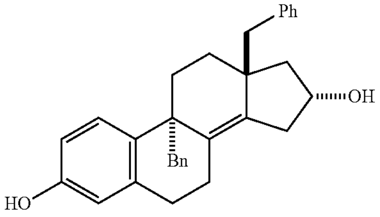
Compound 140
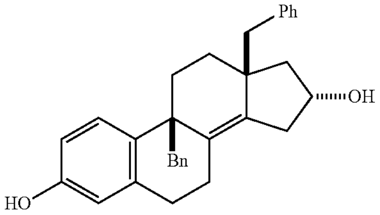
Compound 141
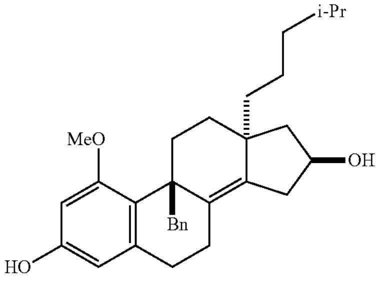
Compound 142
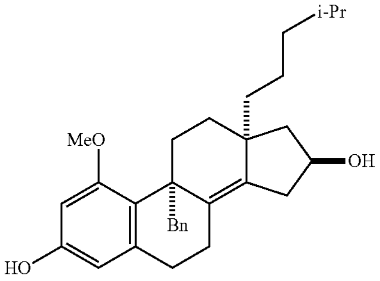
Compound 143
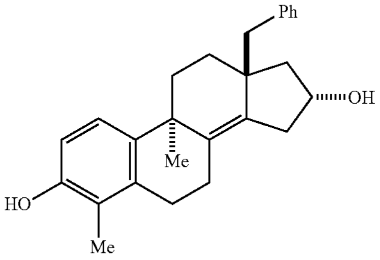
-continued
Compound 144
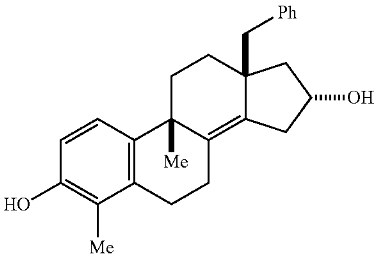
Compound 145
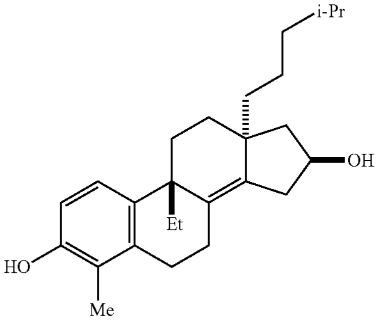
Compound 146
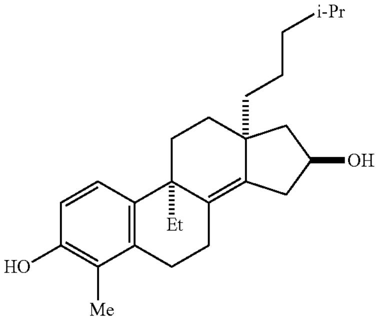
Compound 147
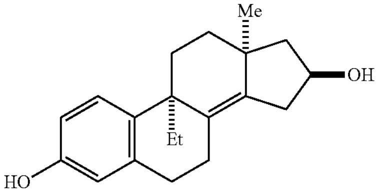
Compound 148
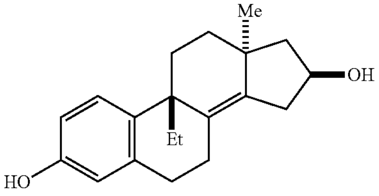
Compound 149
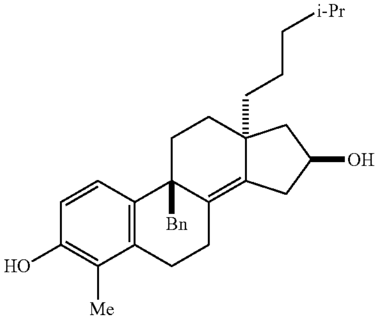

-continued
Compound 150
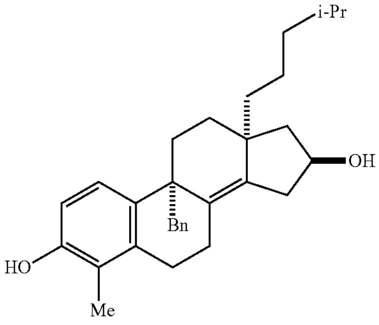
Compound 151
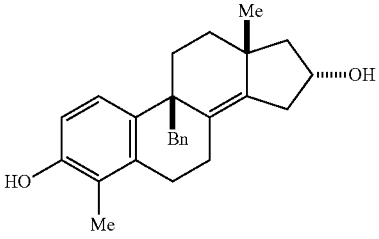
Compound 152
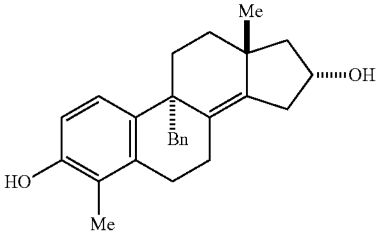
Compound 153
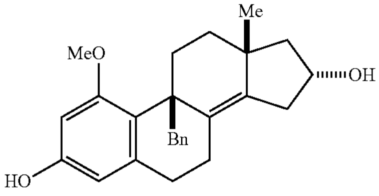
Compound 154
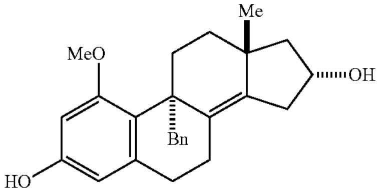
Compound 155
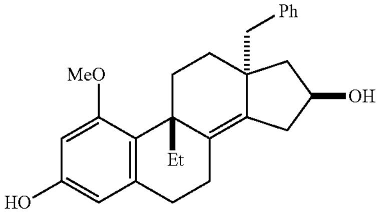
-continued
Compound 156
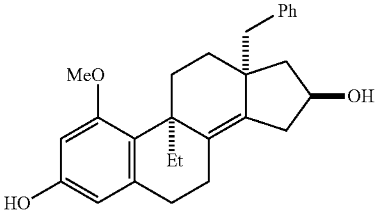
Compound 157
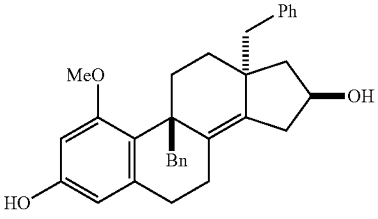
Compound 158
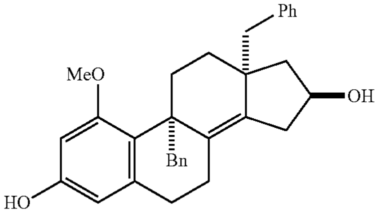
Compound 159
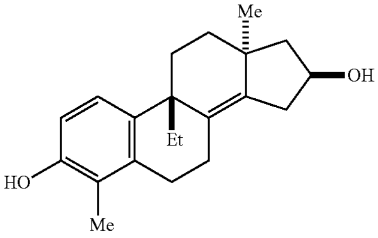
Compound 160
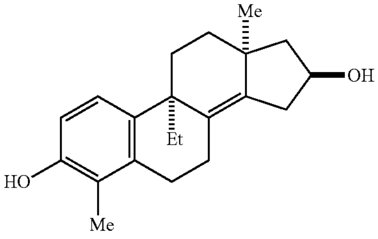
Compound 161
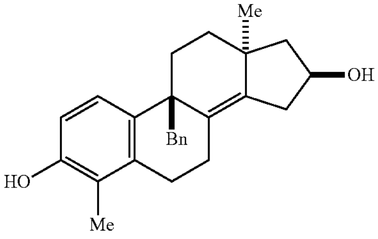

-continued

Compound 162

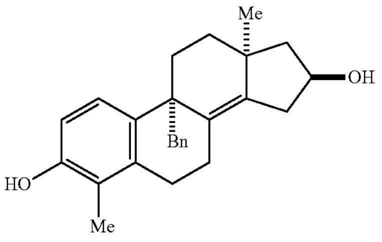

Example 2-1

Compound 200—(10S,13S,16R)-16-hydroxy-10,13-dimethyl-6,7,10,11,12,13,16,17-octahydro-3H-cyclopenta[a]phenanthren-3-one Compound 200

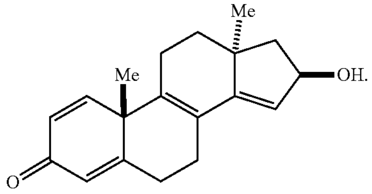

Compound 200 was prepared starting from Steroid 6 by way of an oxidative dearomatization with stereospecific alkyl-shift and regioselective loss of proton.

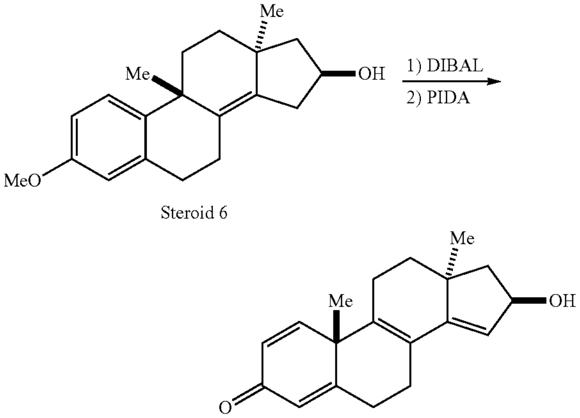

Steroid 6

Compound 200

Compound 200 can be a versatile intermediate for synthesis of unnatural or natural terpenoid or terpenoid-inspired (synthetic novel compositions of matter) agents.

An aspect of this disclosure is the advancement of tetracycles like Steroid 6 to steroidal products possessing a C10 quaternary center. It was found that deprotection proceeds by treatment with diisobutylaluminum hydride (DIBAL), and that exposure of the phenolic product to an oxidant [in this example, phenyliodo (III) diacetate (PIDA)] results in stereospecific migration of the C9 methyl substituent to C10. This oxidative migration process presumably generates a highly stabilized tertiary and allylic carbocation intermediate that is then converted to the product by regioselective loss of a proton. This type of oxidative rearrangement is novel, as PIDA-mediated oxidative dearomatization chemistry has previously been notoriously problematic/ineffective for migration of a methyl group.

The oxidative dearomatization with stereospecific 1,2-migration and regioselective proton loss to convert Steroid 6 to the steroidal tetracycle Compound 200 is a fundamentally new approach to the laboratory construction of such targets, and establishes this process as useful for the synthesis of fused carbocycles that contain an angular quaternary center at C10.

Example 2-2

Alternative Synthesis of Compound 200 from Compound 101

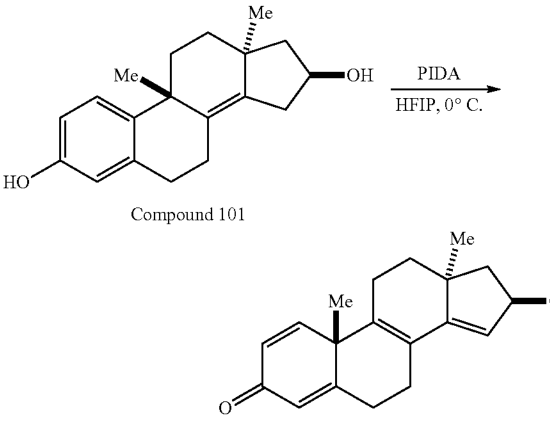

Compound 101

Compound 200

To a round bottom flask charged with Compound 101 (63 mg, 0.22 mmol, 1.0 equiv) at 0° C. under $N_2$ atmosphere was added 2 mL HFIP, and stirred for 6 min. PIDA (70 mg, 0.22 mmol, 1.0 equiv) was added to the reaction mixture, stirred for 1 min at the same temperature (PIDA was fully dissolved at this point), and then 1 mL saturated sodium bicarbonate solution was added. The resulting mixture was further diluted with 20 mL ethyl acetate, and the organic layer was separated. The aqueous layer was extracted with 15 mL ethyl acetate, and then the combined organic layers were concentrated in vacuo. The crude product was purified with $SiO_2$ flash column chromatography to afford 40 mg of the title Compound 200 as an amorphous white solid (64% isolated yield). (Prolonged stirring of more than 30 min after PIDA addition resulted in a significantly lower yield).

Spectral Data for Compound 200: $^1H$ NMR (500 MHZ, Chloroform-d) δ7.16 (d, J=10.1 Hz, 1H), 6.24 (dd, J=10.1, 1.9 Hz, 1H), 6.13 (s, 1H), 5.50 (s, 1H), 5.09-5.01 (m, 1H), 2.78-2.67 (m, 2H), 2.55-2.50 (m, 1H), 2.46-2.39 (m, 1H), 2.32 (dd, J=12.1, 6.5 Hz, 2H), 2.28-2.17 (m, 1H), 1.86-1.78 (m, 2H), 1.57 (td, J=12.4, 5.5 Hz, 1H), 1.46 (s, 3H), 1.40 (dd, J=12.1, 7.6 Hz, 1H), 0.88 (s, 3H); $^{13}C$ NMR (150 MHz, Chloroform-d) δ185.9, 166.6, 152.6, 149.5, 136.9, 128.2, 125.1, 124.7, 123.6, 76.4, 51.5, 44.7, 43.2, 36.1, 29.7, 29.0, 28.6, 24.5, 23.5; IR (thin film): 3388, 2952, 2923, 2851, 1662, 1624, 1057, 887, 731 $cm^{-1}$; HRMS (ESI-TOF): Calculated for $C_{19}H_{23}O_2$ [M+H$^+$] 283.1698. found 283.1693;

$[\alpha]_D^{23} = +128.0$ (c 0.042 g/mL, $CHCl_3$).

Example 2-3

Compound 201-(10S,13R,16S)-16-hydroxy-10,13-dimethyl-6,7,10,11,12,13,16,17-octahydro-3H-cyclopenta[a]phenanthren-3-one

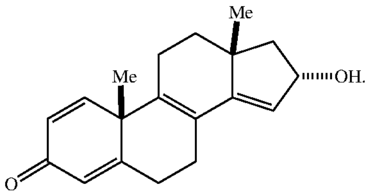 [SMILES: C[C@]12CCC3=C(CCC4=CC(=O)C=C[C@@]43C)C1=C[C@@H](O)C2]

Compound 201 was prepared as above, except starting from Steroid 3.

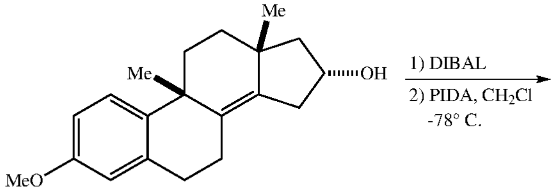

Steroid 3

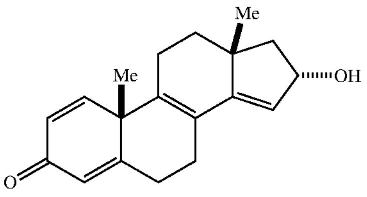

Compound 201

Reductive demethylation of the enantiodefined Steroid 3 with diisobutylaluminum hydride delivered the corresponding phenol in high yield. Oxidative rearrangement was then found to proceed in a highly controlled fashion by treatment with PIDA. As above, stereospecific 1,2-methyl shift from C9 to C10 is thought to deliver a highly stabilized tertiary allylic carbocation intermediate that is terminated by selective loss of a proton from C15, leading to production of the stereodefined dienone, Compound 201—a tetracyclic product that houses quaternary centers at C10 and C13.

Example 2-4

Compound 202-(10R,13S,16R)-16-hydroxy-4,10,13-trimethyl-6,7,10,11,12,13,16,17-octahydro-3H-cyclopenta[a]phenanthren-3-one

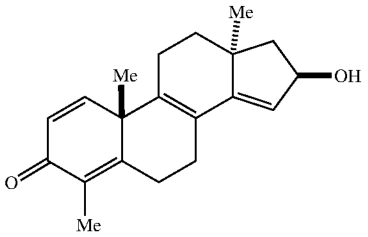 [SMILES: CC1=C2CCC3=C(CC[C@@]4(C)C[C@@H](O)C=C34)[C@@]2(C)C=CC1=O]

Compound 202 was prepared as above, except starting from Compound 102.

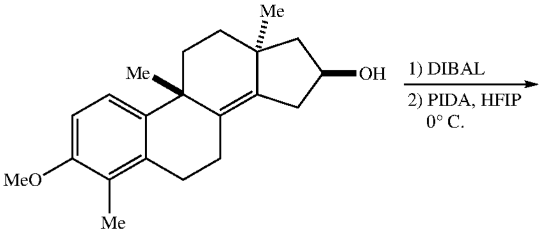

Compound 102

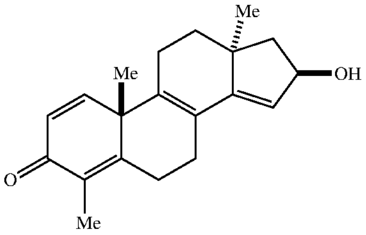

Compound 202

To a stirring solution of Compound 102 (1.5 g, 4.7 mmol, 1.0 equiv) in 50 mL anhydrous toluene at rt under $N_2$ atmosphere was added DIBAL-H (1.0 M in hexanes, 47 mL, 47 mmol, 10 equiv). The resulting mixture was warmed to 100° C., refluxed overnight (approx. 16 hr), and then cooled to rt. Small chunks of ice were slowly added, and the resulting mixture was diluted with 200 mL water, 10 mL 1 M solution of HCl, and 250 mL ethyl acetate. The separated organic layer was dried with $Na_2SO_4$, filtered, and concentrated in vacuo to afford 1.41 g of the crude product as an amorphous yellow solid. The crude product (1.4 g) at 0° C. under $N_2$ atmosphere was added 50 mL HFIP followed by PIDA (1.4 g, 4.3 mmol). The resulting mixture was stirred for 1 min at 0° C. (PIDA was fully dissolved at this point), and then 30 mL saturated solution of $NaHCO_3$ was added. HFIP was removed in vacuo, and the remaining aqueous mixture was extracted with 100 mL×3 ethyl acetate. The combined organic layers were dried over $Na_2SO_4$, filtered, and the filtrate was concentrated in vacuo. The crude product was purified with $SiO_2$ flash column chromatography to afford the title Compound 202 as an amorphous white solid (0.76 g, 54% over 2 steps).

Spectral data for 202: $^1H$ NMR (500 MHZ, Chloroform-d) δ7.14 (d, J=10.1 Hz, 1H), 6.28 (d, J=10.1 Hz, 1H), 5.50 (s, 1H), 5.11-5.02 (m, 1H), 2.97 (ddd, J=13.0, 6.0, 1.7 Hz, 1H), 2.71 (ddt, J=16.5, 6.3, 2.0 Hz, 1H), 2.53-2.39 (m, 2H), 2.34 (app dd, J=12.1, 6.5 Hz, 2H), 2.18 (ddtd, J=18.6, 10.3, 4.1, 2.0 Hz, 1H), 1.95 (s, 3H), 1.82 (ddd, J=12.6, 5.0, 1.4 Hz, 1H), 1.64 (s, 1H), 1.57 (td, J=12.4, 5.6 Hz, 2H), 1.45 (s, 3H), 1.40 (dd, J=12.1, 7.6 Hz, 1H), 0.88 (s, 3H); 13C NMR (150 MHz, Chloroform-d) δ185.4, 159.4, 151.9, 149.9, 137.9, 128.3, 127.6, 125.4, 124.3, 76.6, 51.7, 44.8, 43.3, 36.2, 28.8, 28.4, 25.4, 24.7, 23.6, 10.5; IR (thin film): 3404, 2923, 2851, 1659, 1625, 1607, 1449, 1051, 833, 753 $cm^{-1}$; HRMS (ESI-TOF): calculated for $C_{20}H_{25}O_2$ $[M+H]^+$297.1855. found 297.1856;

$$[\alpha]_D^{22} = +156.27\ (c\ 0.0032,\ CHCl_3).$$

Example 3

The introduction of unsaturated units at strategic locations within a steroid tetracyclic skeleton is challenging. While it is appreciated that there are examples of structures with such unsaturation in the chemistry and biology literature, exploration of this area remains quite cumbersome due to existing technology suitable for preparation of such agents.

The synthetic methods described herein provide access to molecules bearing unsaturated units at strategic locations within the steroid tetracyclic (e.g., C19) skeleton, offering subtle perturbation of three-dimensional structure in comparison to saturated variants, as well as having distinct solubility profiles.

This example demonstrates that introducing additional unsaturation to an exemplary pregnane skeleton (progesterone) can have a significant impact on predicted aqueous solubility (as indicated by the C Log P values reported herein, which were calculated from ChemDraw Professional) and be beneficial for designing more water soluble molecules in the class.

Notably, additional unsaturation of the agents induces subtle changes in overall shape of the molecules, which may impart different physical properties, such as molecular recognition. Such subtle changes may be exploited in projects aiming to identify synthetic compounds that display unique potency and selectivity profiles as modulators of medicinally relevant targets such as the GABAA receptor (GABAAR), pregnane X receptor (PXR), androgen receptor (AR), farnesoid X receptor (FXR), liver X receptor (LXR), and estrogen receptors, as well as other medicinally relevant biological targets (i.e., other nuclear hormone receptors or kinase targets like CDK8 and CDK19).

Comparative Compound 300 (progesterone). The CLogP was determined to be 4.0 (estimated using ChemDraw).

Comparative Compound 300

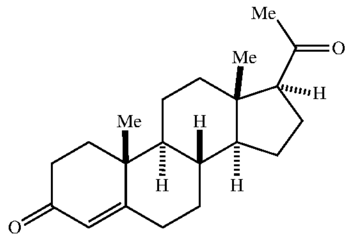

Compound 301 (8,9-unsaturated). The CLogP for Compound 301 was determined to be 3.5 (estimated using ChemDraw) and, therefore, Compound 301 would likely exhibit increased water solubility relative to progesterone.

Compound 301

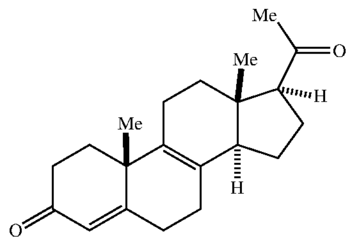

Compound 302 (8,9,14,15-polyunsaturated). The CLogP was determined to be 3.1 (estimated using ChemDraw) and, therefore, Compound 302 would likely exhibit increased water solubility relative to progesterone.

Compound 302

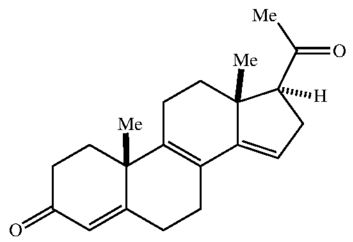

The introduction of unsaturated units at strategic locations within a steroid tetracyclic skeleton has a significant impact on predicted aqueous solubility. Both Compound 301 and Compound 302 exhibit minor, but likely exploitable changes in three-dimensional structure relative to progesterone. Similar perturbation of structure is obvious for ent-progesterone, a molecule that has been described as being of medicinal relevance for the treatment of traumatic brain injury, and other conditions.

Example 4

This example provides a chemical advance to access pharmaceutically relevant steroidal compounds. Steroid 6 was treated in Step (a) with an oxidative cleaving agent to yield Diketone B. Diketone B was subjected to a dehydration and ring-closing reaction to yield Tetracyclic Dienone D, a key intermediate for producing further unique compounds of great medicinal value. The overall sequence of reactions defines a chemical means to formally invert the stereochemistry of C13 of Steroid 6, while introducing medicinally relevant functionality at C15-C17 (an enone of value for subsequent functionalization).

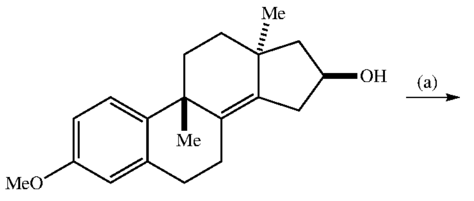

Steroid 6

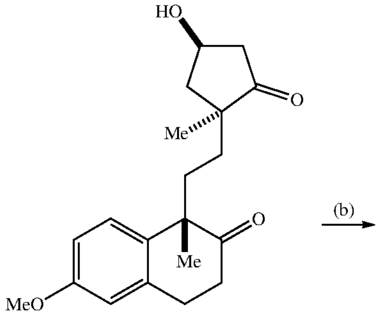

Diketone B

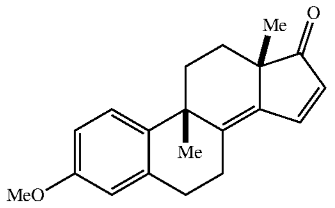

Tetracyclic Dienone D

Diketone B: To a stirring solution of Steroid 6 (0.25 g, 0.84 mmol, 1.0 equiv.) in a 5:1 mixture of MeOH (50 mL) and dichloromethane (10 mL) at −78° C. was introduced $O_3$ (stream of gas, bubbled into solution) for 2.75 min ($O_2$ pressure: 8 psi, flow rate: 1.0, 90 volt). After this period of time, dimethyl sulfide was added (1.0 mL, 14 mmol, 17 equiv.), and the reaction mixture was warmed to rt. The solvents were removed in vacuo, and the remaining residue was partitioned between ethyl acetate and water. The organic layer was separated, and the aqueous layer was extracted with ethyl acetate. The combined organic layers were dried over $MgSO_4$, filtered, and the resulting filtrate was concentrated in vacuo. A subsequent purification by $SiO_2$ flash column chromatography afforded 0.17 g of the title compound Diketone B as a yellow oil (61% isolated yield, 74% BRSM).

$^1$H NMR (600 MHZ, Chloroform-d) δ7.15 (d, J=8.7 Hz, 1H), 6.81 (dd, J=8.6, 2.8 Hz, 1H), 6.67 (d, J=2.7 Hz, 1H), 4.50 (p, J=5.6 Hz, 1H), 3.80 (s, 3H), 3.03-2.94 (m, 2H), 2.72 (ddd, J=14.9, 8.9, 6.9 Hz, 1H), 2.60-2.48 (m, 2H), 2.25 (ddd, J=18.5, 5.1, 1.3 Hz, 1H), 2.09-2.01 (m, 1H), 2.01-1.90 (m, 3H), 1.80-1.70 (m, 1H), 1.37 (s, 3H), 1.16-1.09 (m, 2H), 0.91 (s, 3H). $^{13}$C NMR (151 MHZ, Chloroform-d) δ220.7, 215.5, 158.0, 137.2, 133.5, 127.7, 113.3, 113.2, 67.2, 55.4, 51.2, 48.9, 47.1, 44.6, 38.4, 34.3, 32.9, 28.7, 28.4, 22.0; IR: 3453, 2960, 2932, 2867, 1736, 1708, 1609, 1577, 1503, 1458, 1273, 1076, 1033, 819, 735, 700. HRMS (ESI-TOF): Calculated for $C_{20}H_{27}O_4$ $[M+H]^+$331.1909. found 331.1903;

$$[\alpha]_D^{23} = -29.9\ (c\ 0.0039,\ \text{MeOH}).$$

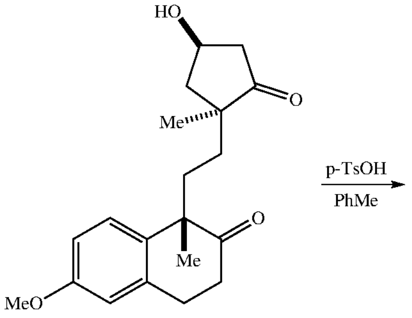

B

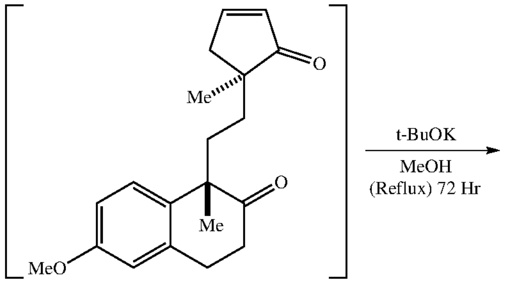

C

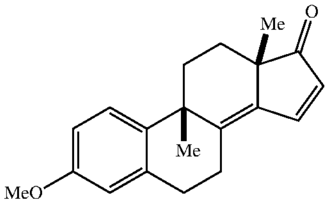

D

55% (2 steps)

Tetracyclic Dienone D: To a stirring solution of Diketone B (0.36 g, 1.1 mmol, 1.0 equiv.) in 36 mL PhMe was added p-TsOH (0.27 g, 1.6 mmol, 1.5 equiv.). The resulting mixture was warmed in a 60° C. oil bath, stirred for 45 min, and then cooled to rt. The reaction mixture was then diluted with 40 mL dichloromethane, and then 50 mL water. The organic layer was separated, and the aqueous layer was extracted with 3×30 mL dichloromethane. The combined organic layers were dried over $Na_2SO_4$, filtered and then concentrated in vacuo. The residue (0.369 g) was dissolved in 55 mL MeOH, and KOt-Bu (0.40 g, 3.5 mmol) was added. The resulting mixture was warmed with an 82° C. oil bath and stirred for 72 hr. After this period, the reaction mixture was cooled to rt, and then quenched with 40 mL saturated solution of $NH_4Cl$. MeOH was removed in vacuo, and the resulting residue was further diluted with 60 mL ethyl acetate and 100 mL water. The organic layer was separated, and the aqueous layer was extracted with 6×125 mL ethyl acetate. The combined organic layers were dried over $Na_2SO_4$, filtered, and then concentrated in vacuo. A subsequent purification by $SiO_2$ flash column chromatography afforded 0.18 g of the title compound Tetracyclic Dienone D as a yellow oil (55% isolated yield).

$^1$H NMR (500 MHZ, Chloroform-d) δ8.04 (d, J=5.8 Hz, 1H), 7.30-7.18 (m, 1H), 6.76 (dd, J=8.7, 2.8 Hz, 1H), 6.52 (d, J=2.8 Hz, 1H), 6.07 (d, J=5.8 Hz, 1H), 3.76 (s, 3H), 2.93 (ddd, J=15.8, 5.8, 2.2 Hz, 1H), 2.88 (ddd, J=12.6, 5.5, 2.2 Hz, 1H), 2.82-2.72 (m, 1H), 2.57 (dt, J=12.6, 6.3 Hz, 1H), 2.50 (dt, J=14.6, 3.7 Hz, 1H), 2.18 (td, J=14.3, 4.0 Hz, 1H), 1.71 (dt, J=12.8, 3.7 Hz, 1H), 1.51 (s, 3H), 1.27 (s, 3H), 1.22-1.13 (m, 1H). $^{13}C$ NMR (126 MHZ, Chloroform-d) δ212.05, 157.50, 153.09, 141.40, 138.91, 138.35, 137.52, 129.38, 127.47, 113.15, 112.89, 55.30, 46.59, 40.93, 35.34, 33.95, 33.04, 26.43, 24.66, 22.83. IR: 2960, 2925, 2857, 2360, 2332, 1703, 1497, 1231, 1038, 830. HRMS (ESI-TOF): Calculated for $C_{20}H_{23}O_2$ $[M+H]^+$295.1698. found 295.1693;

$$[\alpha]_D^{23} = -56.9\ (c\ 0.0035,\ CHCl_3).$$

Notably, Tetracyclic Dienone D has been shown to be prepared through a chemical sequence that involves a conceptually novel rearrangement including a formal inversion of C13 and installation/establishment of a C17 ketone.

From key Tetracyclic Dienone D, many further compounds may be prepared.

For example, Compound 400, a novel pregnane, is uniquely accessible in a concise and asymmetric fashion with the chemical technology described herein.

Compound 400 (10S,13R,17S)-17-((S)-1-hydroxyethyl)-10,13-dimethyl-6,7,10,11,12,13,16,17-octahydro-3H-cyclopenta[a]phenanthren-3-one

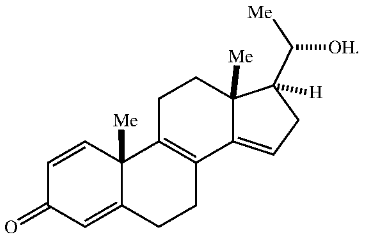 [SMILES: C[C@H](O)[C@H]1CC=C2C3=C(CC[C@@]21C)[C@@]1(C)C=CC(=O)C=C1CC3]

Compound 400 was prepared starting from Tetracyclic Dienone D as shown below.

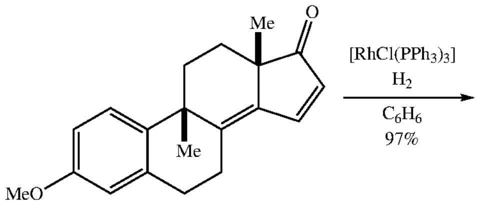

D

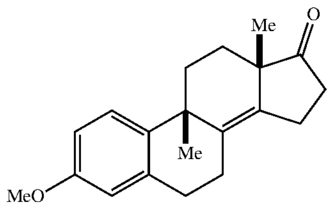

E

Tetracyclic Ketone E: To a stirring solution of Wilkinson's catalyst (45 mg, 0.049 mmol, 0.1 equiv.) and D (145 mg, 0.49 mmol, 1 equiv.) in dry benzene (5 mL) was bubbled $N_2$ for a period of 15 minutes. Subsequently, $H_2$ gas was bubbled into the solution while stirring for three minutes and then the reaction mixture was stirred under 1 ATM $H_2$ for 5 hours until the starting material was consumed (as indicated by TLC analysis). The solvent was then removed under reduced pressure and the crude material was purified by flash column chromatography to yield 134 mg of the title compound E as a clear film (97% isolated yield).

$^1H$ NMR (500 MHZ, Chloroform-d) δ7.22 (d, J=8.7 Hz, 1H), 6.73 (dd, J=8.6, 2.8 Hz, 1H), 6.59-6.56 (m, 1H), 3.76 (s, 3H), 2.90-2.83 (m, 1H), 2.82-2.65 (m, 3H), 2.65-2.54 (m, 2H), 2.44-2.34 (m, 1H), 2.20-2.06 (m, 1H), 1.95-1.84 (m, 1H), 1.83-1.78 (m, 1H), 1.78-1.72 (m, 1H), 1.71-1.63 (m, 1H), 1.37 (s, 3H), 1.17 (s, 3H). $^{13}C$ NMR (126 MHZ, Chloroform-d) δ219.53, 157.35, 138.03, 137.95, 137.54, 126.87, 113.53, 112.34, 55.31, 48.52, 38.98, 36.34, 35.03, 31.70, 30.55, 26.74, 24.62, 24.09, 22.90. IR: 2958, 2926, 2863, 1740, 1608, 1498, 1450, 1272, 1234, 1039, 814. Calculated for $C_{20}H_{25}O_2$ $[M+H]^+$297.1855. found 297.1854;

$$[\alpha]_D^{23} = 71.1\ (c\ 0.003,\ CHCl_3).$$

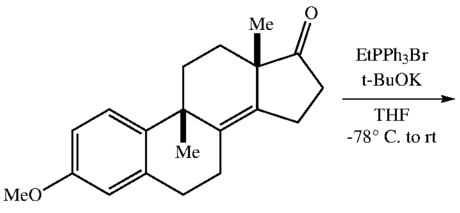

E

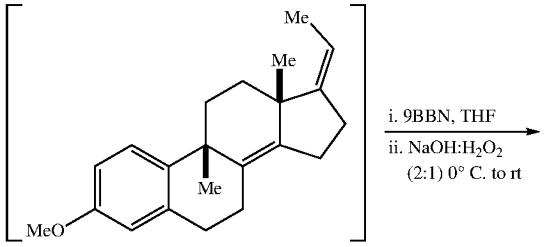

F

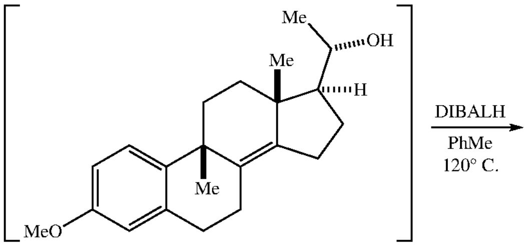

G

-continued

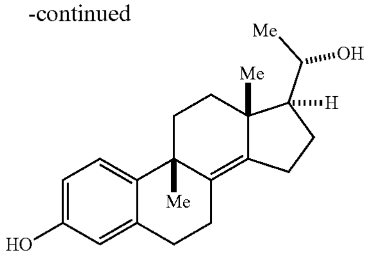

H
31% (3 steps)

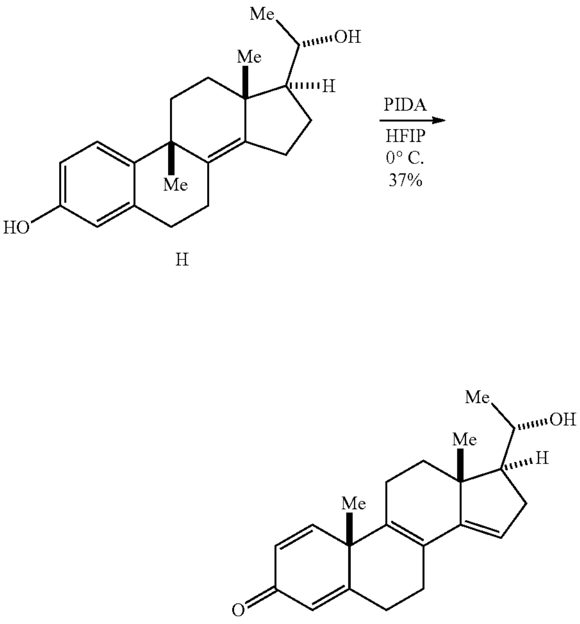

H

I

Tetracyclic Phenol H: To a round bottom flask under $N_2$, containing t-BuOK (360 mg, 3.2 mmol, 5 equiv.) and $EtPPh_3Br$ (1.40 g, 3.2 mmol, 5 equiv.) was delivered 6.5 mL THF. The resulting suspension was cooled to −78° C., and E (190 mg, 0.64 mmol, 1 equiv.) was subsequently introduced as a solution in THF (1.5 mL) in a dropwise manner. The resulting solution was stirred for 15 minutes at −78° C. (dry ice/acetone bath), then allowed to warm to room temperature overnight. After the reaction was judged to be complete by TLC analysis, the solvent was removed under reduced pressure. The resulting solid residue was dissolved in 1:5 EtOAc: hexanes (45 mL) and filtered through a thin pad of silica. The filtrate was concentrated to yield a clear oil to which 9BBN (0.5 M in THF, 9 mL, 4.5 mmol, 7 equiv.) was delivered. The resulting solution was stirred at ambient temperature under $N_2$ for 36 hours. The reaction was quenched with 15 mL of a 2:1 solution of aqueous 10% NaOH: 30% $H_2O_2$ in $H_2O$, and the resulting opaque solution was allowed to stir overnight. The solution was then diluted with 20 mL ethyl acetate and 15 mL water. The organic layer was separated, and the aqueous layer was extracted with 4×40 mL ethyl acetate. The combined organic layers were dried over $Na_2SO_4$, filtered, and then concentrated in vacuo. To a stirring solution of the resulting crude material in 9 mL anhydrous toluene at rt under $N_2$ atmosphere was added DIBAL-H (1.0 M in hexanes, 9.0 mL, 9.0 mmol, 14 equiv.). The resulting mixture was refluxed for approx. 20 hr (oil bath maintained at ~120° C.) and then cooled to rt. Small chunks of ice were slowly added, and the resulting mixture was further diluted with 5 mL $H_2O$ and 10 mL EtOAc, then acidified with 1M aqueous hydrochloric acid (15 mL). The organic layer was separated, and the aqueous layer was extracted with 4×20 mL ethyl acetate. The combined organic layers were dried over $Na_2SO_4$, filtered, and then the resulting filtrate was concentrated in vacuo. The crude product was purified by $SiO_2$ flash column chromatography to afford 88 mg of the title compound H as an amorphous white solid (31% isolated yield over 3 steps).

Spectral Data for H: $^1H$ NMR (600 MHZ, Methanol-$d_4$) δ7.11 (d, J=8.6 Hz, OH), 6.54 (dd, J=8.5, 2.7 Hz, OH), 6.41 (d, J=2.7 Hz, OH), 3.68 (dq, J=7.9, 6.3 Hz, OH), 2.80-2.62 (m, 1H), 2.46 (ddd, J=13.3, 6.0, 2.9 Hz, OH), 2.39-2.31 (m, 1H), 2.27 (ddd, J=14.3, 5.0, 3.4 Hz, OH), 2.02-1.84 (m, 1H), 1.76-1.63 (m, 1H), 1.28 (s, 1H), 1.23 (dt, J=11.7, 7.6 Hz, OH), 1.18 (d, J=6.3 Hz, 1H), 1.09 (td, J=13.0, 12.6, 3.0 Hz, OH), 0.96 (s, 1H). $^{13}C$ NMR (151 MHZ, Chloroform-d) δ185.68, 166.56, 153.34, 146.44, 135.17, 127.99, 126.26, 123.52, 118.34, 82.16, 47.12, 46.32, 46.27, 44.63, 29.84, 29.23, 28.95, 27.16, 24.78, 24.71, 23.45, 17.51.

Compound 400 (Pregnane I): The tetracyclic phenol H (50 mg, 0.16 mmol, 1 equiv.) was dissolved in 1.6 mL HFIP, cooled to 0° C. under $N_2$ atmosphere, and stirred for 20 min. PIDA (49 mg, 0.15 mmol, 0.95 equiv.) was added to the reaction mixture, stirred for 1 min at the same temperature (until PIDA appeared to be fully dissolved), and then 1 mL saturated solution of $NaHCO_3$ was added. HFIP was subsequently removed from the reaction mixture under vacuum, and the resulting material was diluted with 10 mL ethyl acetate. The organic layer was separated, and the aqueous layer was extracted with 3×20 mL ethyl acetate. The organic layers were combined and dried over $Na_2SO_4$, then filtered, and the filtrate was concentrated in vacuo. The crude product was purified with $SiO_2$ flash column chromatography to afford 18 mg of the polyunsaturated pregnane I as a clear film (37% isolated yield).

$^1H$ NMR (600 MHz, Chloroform-d) δ7.23 (d, J=10.2 Hz, 1H), 6.25 (dd, J=10.2, 1.9 Hz, 1H), 6.13 (d, J=1.7 Hz, 1H), 5.49 (t, J=2.6 Hz, 1H), 3.91 (dt, J=8.7, 5.6 Hz, 1H), 2.79-2.69 (m, 1H), 2.58-2.46 (m, 6H), 2.40-2.32 (m, 2H), 1.97 (dt, J=12.8, 3.2 Hz, 1H), 1.75 (dt, J=10.0, 8.2 Hz, 1H), 1.49-1.40 (m, 4H), 1.27 (d, J=6.0 Hz, 4H), 0.89 (s, 3H). $^{13}C$ NMR (151 MHZ, Chloroform-d) δ185.71, 166.57, 153.43, 148.69, 134.25, 127.93, 125.64, 123.45, 120.13, 69.12, 58.94, 44.51, 44.29, 35.60, 34.04, 29.94, 29.86, 28.84, 23.73, 23.48, 16.34.

The general scheme for preparing Compound 400 is summarized below:

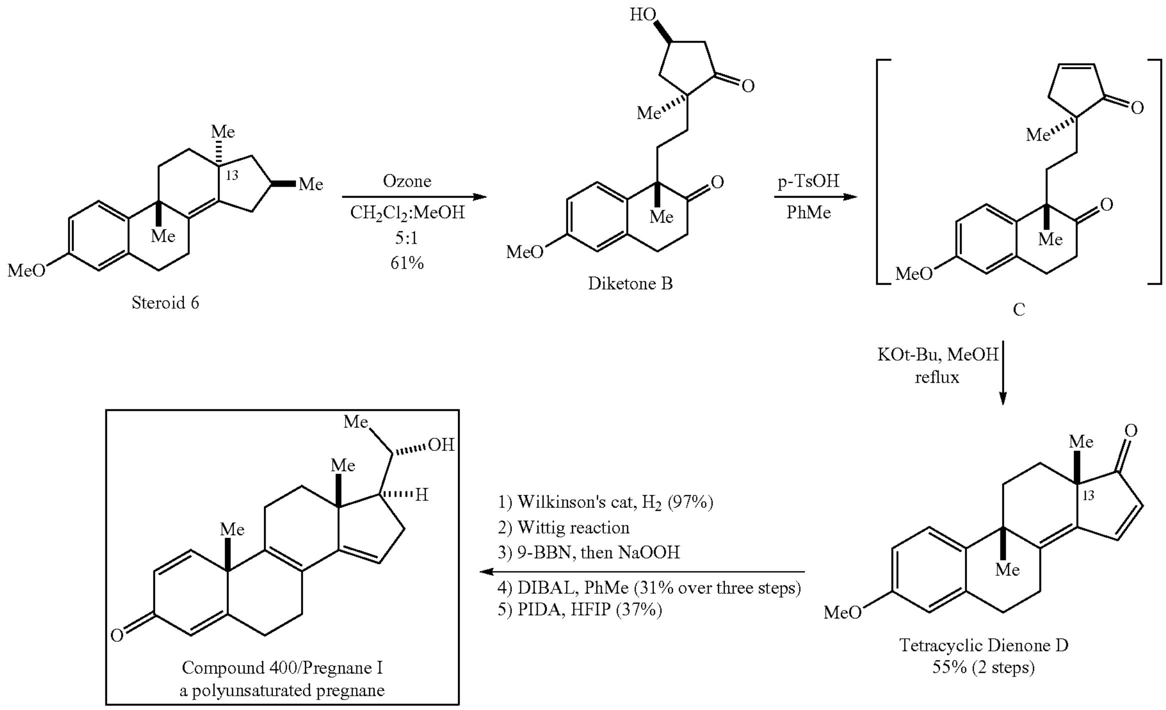

Steroid 6

Diketone B

C

Tetracyclic Dienone D
55% (2 steps)

Compound 400/Pregnane I
a polyunsaturated pregnane

Likewise, Compound 401, an androstane, is uniquely accessible in a concise and asymmetric fashion with the chemical technology described herein.

Compound 401-(10S,13S,17S)-17-hydroxy-10,13-dimethyl-6,7,10,11,12,13,16,17-octahydro-3H-cyclopenta[a]phenanthren-3-one

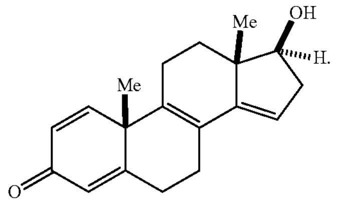

Compound 401 was prepared from Tetracyclic Dienone D as shown below. In particular, Tetracyclic Dienone D was treated in Step (c) (1. Wilkinson's cat, $H_2$; 2. DIBALH, PhMe; 3. PIDA, HFIP) to yield Compound 401.

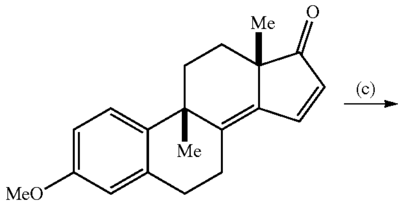

Tetracyclic Dienone D

-continued

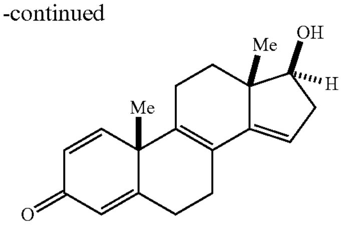

Compound 401

This example built on the chemistry previously described herein, particularly in Example 1 by providing a novel sequence of ring-opening, dehydration, and ring-closing to alter the stereochemistry at C13 as well as install a ketone functional group at C17.

The processes and intermediates described herein, particularly Tetracyclic Dienone D, are valuable as a means of accessing both polyunsaturated pregnane and androstane skeletons through simple sequences of reactions.

In sum, the technology described herein greatly expands the type of tetracyclic terpenoid skeletons that can be easily prepared. Because compounds accessible with this technology are in a pharmaceutically privileged space, such compounds may be useful as active pharmaceutical agents (API) or in the synthesis/production of an API.

Example 5

This example describes enhanced levels of stereoselection in the mismatched double asymmetric Friedel-Crafts Cyclization, which is also effective for the matched double asymmetric reaction.

Highest selectivities for the mismatched double asymmetric Friedel-Crafts cyclization have been observed with substrates that do not have a free hydroxy group. It is believed that substrates bearing suitably acidic functional groups can be problematic in this double asymmetric cyclization owing to the fact that the substrate itself can serve as a source of Brønstead acid for the cationic cyclization. In the example shown below, the hydrindane substrate 14 possesses a methyl ether at the steroidal C16 position rather than a free hydroxy group.

Mismatched double asymmetric reaction

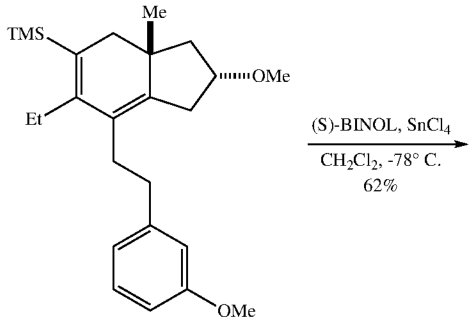

14

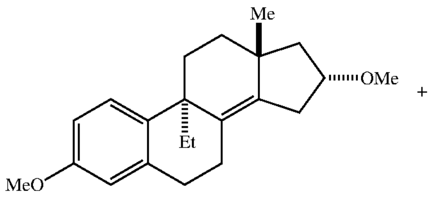

+

Compound 500

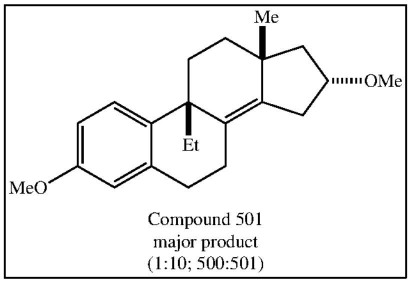

Compound 501
major product
(1:10; 500:501)

Mismatched double asymmetric reaction: Selective generation of tetracycle 501—To a stirred solution of (S)-BINOL (132 mg, 0.461 mmol, 1.2 equiv.) in $CH_2Cl_2$ (3 mL) cooled with a −78° C. dry ice/acetone bath was added $SnCl_4$ (0.384 mL, 0.384 mmol, 1.0 M in $CH_2Cl_2$, 1.0 equiv.). The solution was stirred for ~30 minutes at −78° C. before the addition of hydrindane 14 (153 mg, 0.384 mmol, 1 equiv.) in $CH_2Cl_2$ (1 mL). The reaction mixture was stirred at −78° C. for 1 hour before being warmed to rt where it was stirred for another hour before adding sat. aq. $NH_4Cl$ (1 mL). The biphasic solution was stirred for 1 hour before being transferred to a separatory funnel. The phases were separated, and the aqueous phase was extracted with $CH_2Cl_2$ (3×10 mL). The combined organic phase was washed with 5% NaOH (1 mL), dried over $Na_2SO_4$, filtered, and concentrated in vacuo. The resulting crude product was purified by flash chromatography with a BIOTAGE® Snap Ultra 25 g column and a gradient from 0-20% EtOAc in hexanes to afford the corresponding tetracycles as a mixture of the anti-(500) to syn-(501) isomers (62%, dr 1:10) as a white foam.

Analytical data for Compound 501: $^1H$ NMR (600 MHZ, $CDCl_3$): δ7.15 (d, J=8.6 Hz, 1H), 6.71 (dd, J=8.6, 2.8 Hz, 1H), 6.60 (d, J=2.8 Hz, 1H), 4.15-4.08 (m, 1H), 3.77 (s, 3H), 3.33 (s, 3H), 2.96-2.90 (m, 1H), 2.78-2.71 (m, 2H), 2.5-2.43 (m, 1H), 2.41-2.35 (m, 1H), 2.32-2.21 (m, 2H), 2.16-2.12 (m, 1H), 1.80-1.74 (m, 1H), 1.71-1.60 (m, 4H), 1.33-1.29 (m, 1H), 0.88 (s, 3H), 0.72 (t, J=7.5 Hz, 3H); $^{13}C$ NMR (150 MHZ, $CDCl_3$): δ157.2 (C), 138.3 (C), 137.8 (C), 137.0 (C), 131.0 (C), 127.8 (CH), 113.3 (CH), 111.4 (CH), 80.2 (CH), 57.0 ($CH_3$), 55.2 ($CH_3$), 48.7 (C), 41.1 (C), 34.5 ($CH_2$), 33.7 ($CH_2$), 33.3 ($CH_2$), 30.9 ($CH_2$), 30.0 ($CH_2$), 25.8 ($CH_3$), 24.8 ($CH_2$), 10.0 ($CH_3$); IR (neat, $cm^{-1}$): 2934 (s), 1608 (m), 1576 (w), 1497 (s), 1464 (m), 1371 (m), 1309 (w), 1260 (m), 1231 (m), 1192 (w), 1167 (w), 1101 (s), 1043 (m), 865 (w), 815 (w); HRMS (ESI-TOF) (m/z): $[M+H]^+$ calcd for $C_{22}H_{31}O_2$ 327.2324; found, 327.2312;

$$[\alpha]^{22.0}_{589}: -93.462\ (c\ 0.0015,\ CHCl_3),$$

Analytical data for Compound 500: $^1H$ NMR (600 MHZ, $CDCl_3$): δ7.21 (d, J=7.3 Hz, 1H), 6.70 (dd, J=8.7, 2.8 Hz, 1H), 6.58 (d, J=2.8 Hz, 1H), 4.14-4.07 (m, 1H), 3.77 (s, 3H), 3.30 (s, 3H), 2.91-2.80 (m, 3H), 2.46-2.40 (m, 1H), 2.36-2.25 (m, 2H), 2.14-2.08 (m, 1H), 2.04-1.93 (m, 2H), 1.69-1.50 (m, 3H), 1.22-1.14 (m, 2H), 1.04 (s, 3H), 0.77 (t, J=14.7 Hz, 3H); $^{13}C$ NMR (150 MHz, $CDCl_3$): δ157.3 (C), 138.7 (C), 138.6 (C), 138.3 (C), 131.1 (C), 125.9 (CH), 114.0 (CH), 111.4 (CH), 79.8 (CH), 56.9 ($CH_3$), 55.2 ($CH_3$), 48.2 ($CH_2$), 43.2 (C), 41.1 (C), 36.0 ($CH_2$), 34.7 ($CH_2$), 33.7 ($CH_2$), 31.4 ($CH_2$), 28.2 ($CH_2$), 25.6 ($CH_3$), 24.3 ($CH_2$), 9.5 ($CH_3$); IR (neat, $cm^{-1}$): 2955 (s), 1606 (m), 1497 (s), 1463 (m), 1371 (m), 1338 (m), 1245 (s), 1206 (w), 1168 (w), 1144 (m), 1121 (m), 1099 (m), 1040 (m), 999 (m), 867 (s), 848 (s), 816 (m), 749 (m); HRMS (ESI-TOF) (m/z): $[M+H]^+$ calcd for $C_{22}H_{31}O_2$ 327.2324; found, 327.2319;

$$[\alpha]^{21.8}_{589}: +95.617\ (c\ 0.00016,\ CHCl_3).$$

Matched double asymmetric reaction

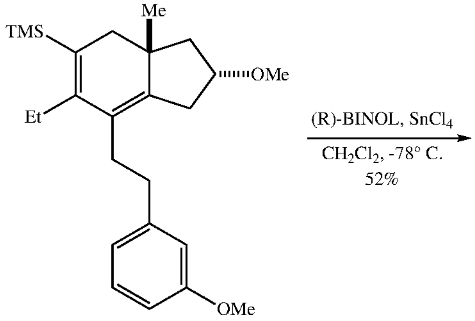

14

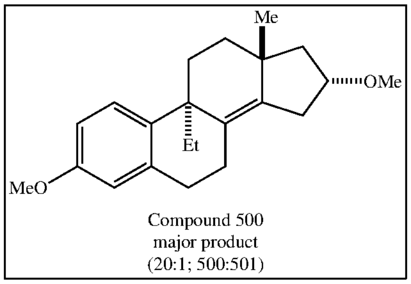

+

Compound 500
major product
(20:1; 500:501)

-continued

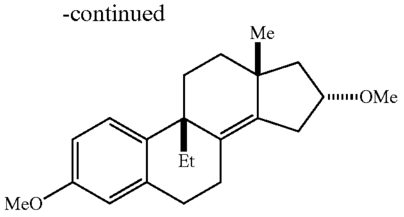

Compound 501

Matched double asymmetric reaction: Selective generation of tetracycle 500—To a stirred solution of (R)-BINOL (61 mg, 0.212 mmol, 1.2 equiv.) in $CH_2Cl_2$ (1 mL) cooled with a −78° C. dry ice/acetone bath was added $SnCl_4$ (0.177 mL, 0.177 mmol, 1.0 M in $CH_2Cl_2$, 1.0 equiv.). The solution was stirred for 30 minutes at −78° C. before the addition of hydrindane (70 mg, 0.177 mmol, 1 equiv.) in $CH_2Cl_2$ (1 mL). The reaction mixture was stirred at −78° C. for 1 hour before being warmed to rt where it was stirred for another hour before sat. aq. $NH_4Cl$ (1 mL) was added. The biphasic solution was stirred for 1 hour before being transferred to a separatory funnel. The phases were separated, and the aqueous phase was extracted with $CH_2Cl_2$ (3×10 mL). The combined organic phase was washed with 5% NaOH (1 mL), dried over $MgSO_4$, filtered, and concentrated in vacuo. The resulting crude product was purified by flash chromatography with a BIOTAGE® Snap Ultra 25 g column and a gradient from 0-20% EtOAc in hexanes to afford the corresponding tetracycles as a mixture of the anti-(500) to syn-(501) isomers (52%, dr 20:1) as a white foam.

Example 6

This example explored the utility of intramolecular Heck reactions for C9-C10 bond formation. Reactions (1)-(4) are depicted below.

(1)

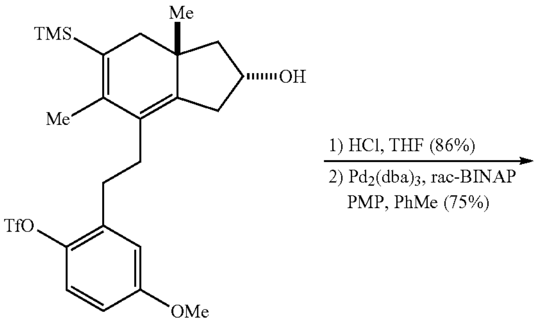

Hydrindane 6-1

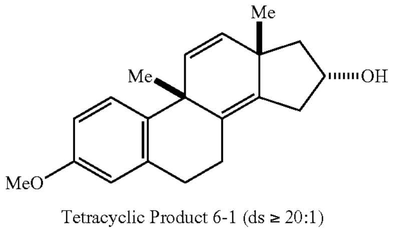

Tetracyclic Product 6-1 (ds ≥ 20:1)

(2)

-continued

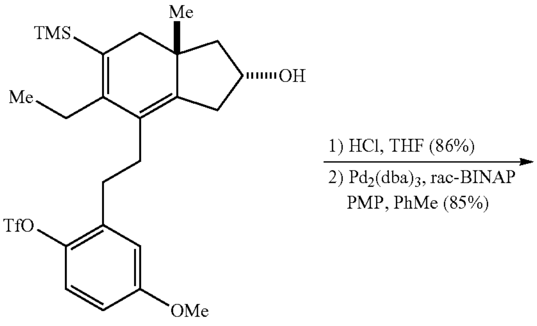

Hydrindane 6-2

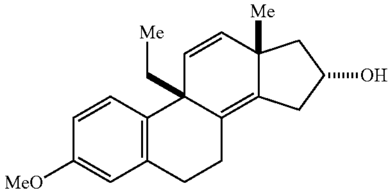

Tetracyclic Product 6-2 (ds ≥ 20:1)

(3)

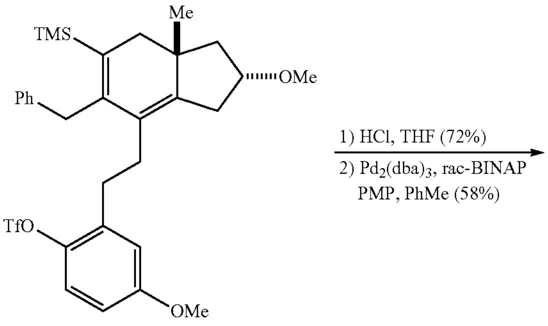

Hydrindane 6-3

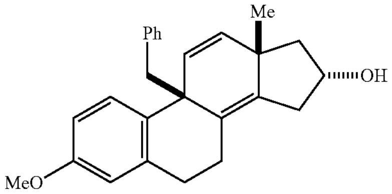

Tetracyclic Product 6-3 (ds ≥ 20:1)

(4)

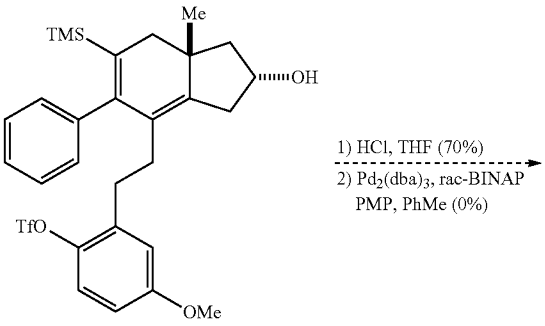

Hydrindane 6-4

-continued

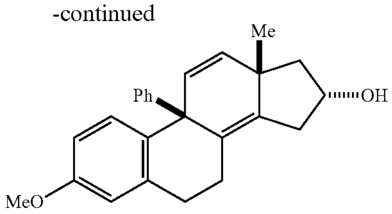

Tetracyclic Product 6-4 (ds ≥ 20:1)

Triflate-containing hydrindane substrates 6-1, 6-2, 6-3, and 6-4 were first desilylated at $C_{11}$ by the action of HCl in THF, and subsequent Heck reaction was accomplished by treatment with $Pd_2(dba)_3$ rac-BINAP and 1,2,2,6,6-pentamethylpiperidine in toluene at 110° C. In most cases, the cyclization proceeded with exquisite levels of stereoselectivity in favor of the C9/13-syn isomers (ds≥20:1), providing access to the Tetracyclic Products 6-1, 6-2, and 6-3 in 42-73% yield over the two-step process. This sequence of reactions was not effective for producing the C9 Ph-substituted tetracycle, Tetracyclic Product 6-4.

Example 7

Prostatic epithelial hyperplasia is evident in mice lacking ERβ suggesting that ERβ may play a role in limiting proliferation in the prostate. These data suggest that pharmacological activation of ERβ may be useful in treatment of prostate cancer. The DU-145 prostate cancer cell line only expresses ERβ and can be used as a model to examine the activation of ERβ in the absence of any potential confounding signal driven by ERα. Alkaline phosphatase (ALP) expression is induced in an ER-dependent manner and has been used to characterize the activity of synthetic ER agonists and antagonists.

Figure 2:
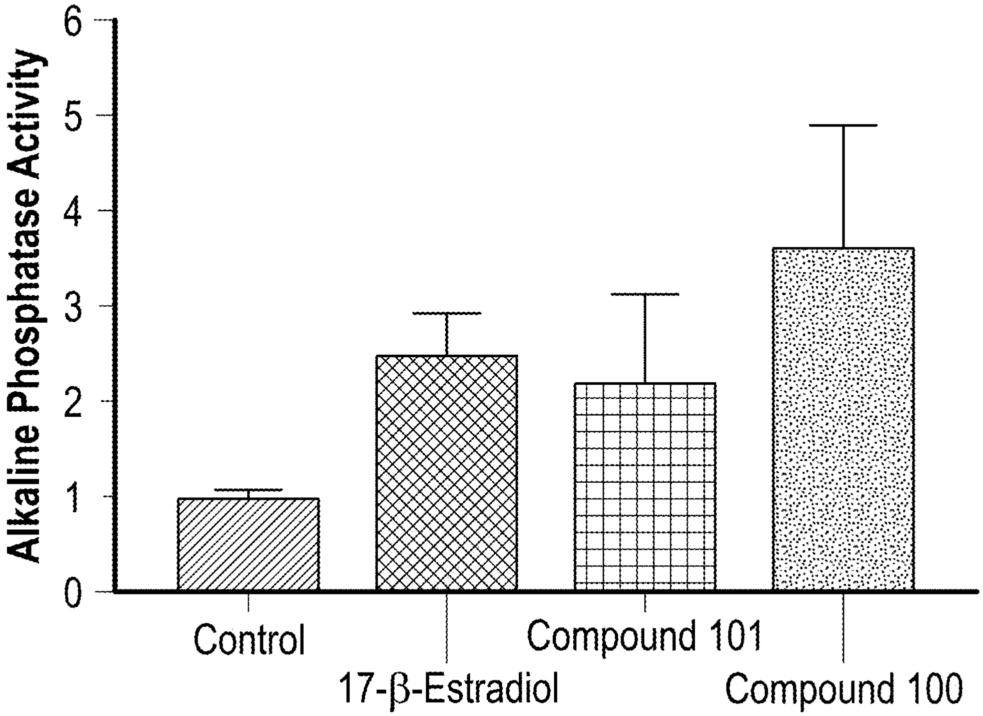
FIG. 2 is a bar graph showing alkaline phosphatase activity in human DU-145 prostate cancer cells (17β-estradiol, Compound 100, and Compound 101 were evaluated at 5 μM).

In order to examine the ability of Compound 100 and Compound 101 to activate ERβ in the context of a cell line expressing endogenous ERβ, DU-145 cells were treated for 24 hours with either 17β-estradiol, Compound 100, or Compound 101 and ALP activity derived from the cells was examined. As shown in FIG. 2, 17β-estradiol was effective in inducing ALP activity as expected. Additionally, both Compound 100 and Compound 101 were effective at inducing ALP to levels comparable to 17β-estradiol. These data are consistent with Compound 100 and Compound 101 functioning as ERβ agonists.

Example 8

Figure 3A:
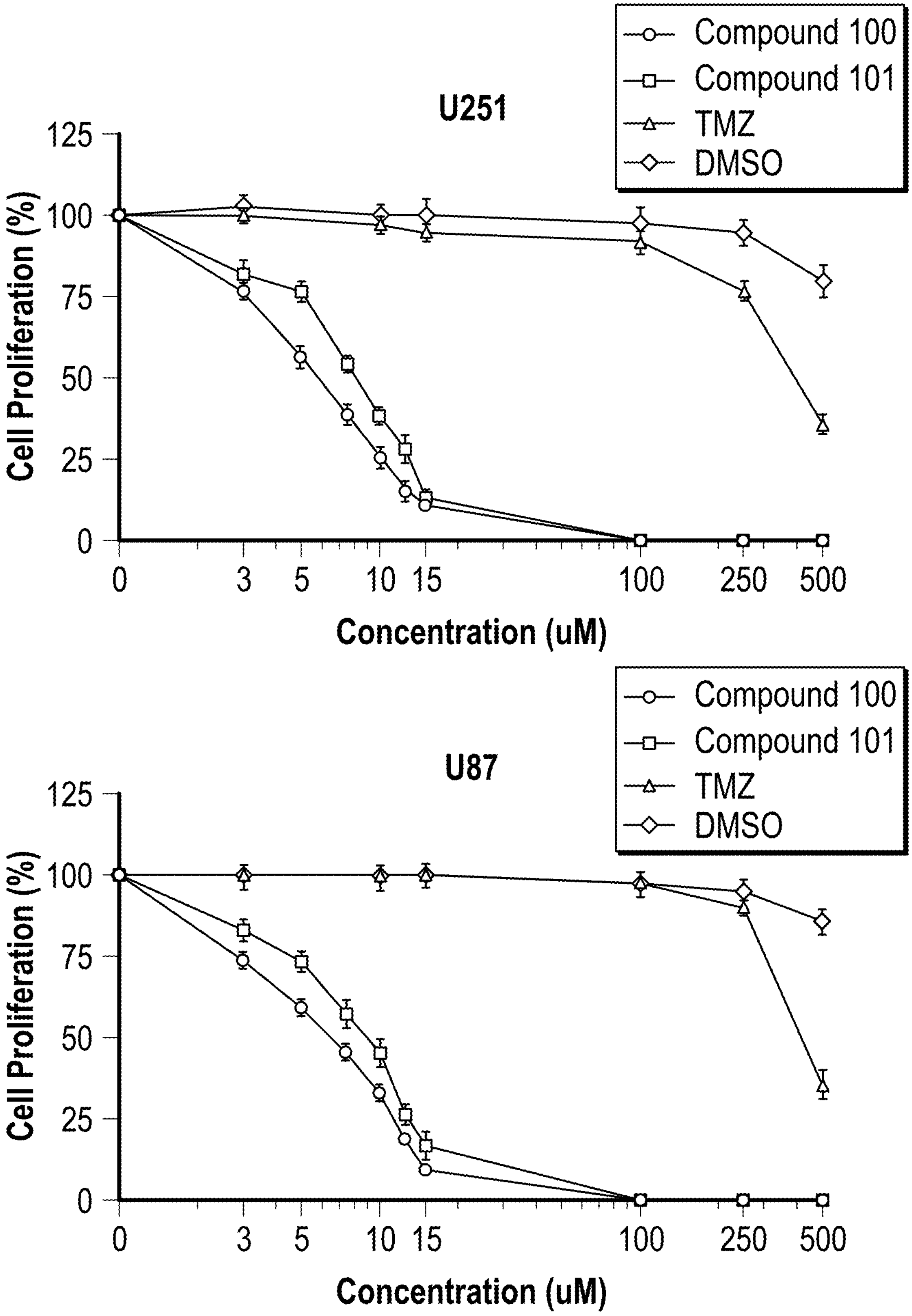
FIG. 3A-3B are line graphs depicting (A) dose dependent growth inhibition of U251 and U87 cells treated with Compound 100, Compound 101, TMZ, and vehicle control DMSO (n=4) and (B) viable cell counts of U251 and U87 cells treated with Compound 100, Compound 101, TMZ, and vehicle control DMSO determined every 24 hours for 96 hours (n=4)
Figure 3B:
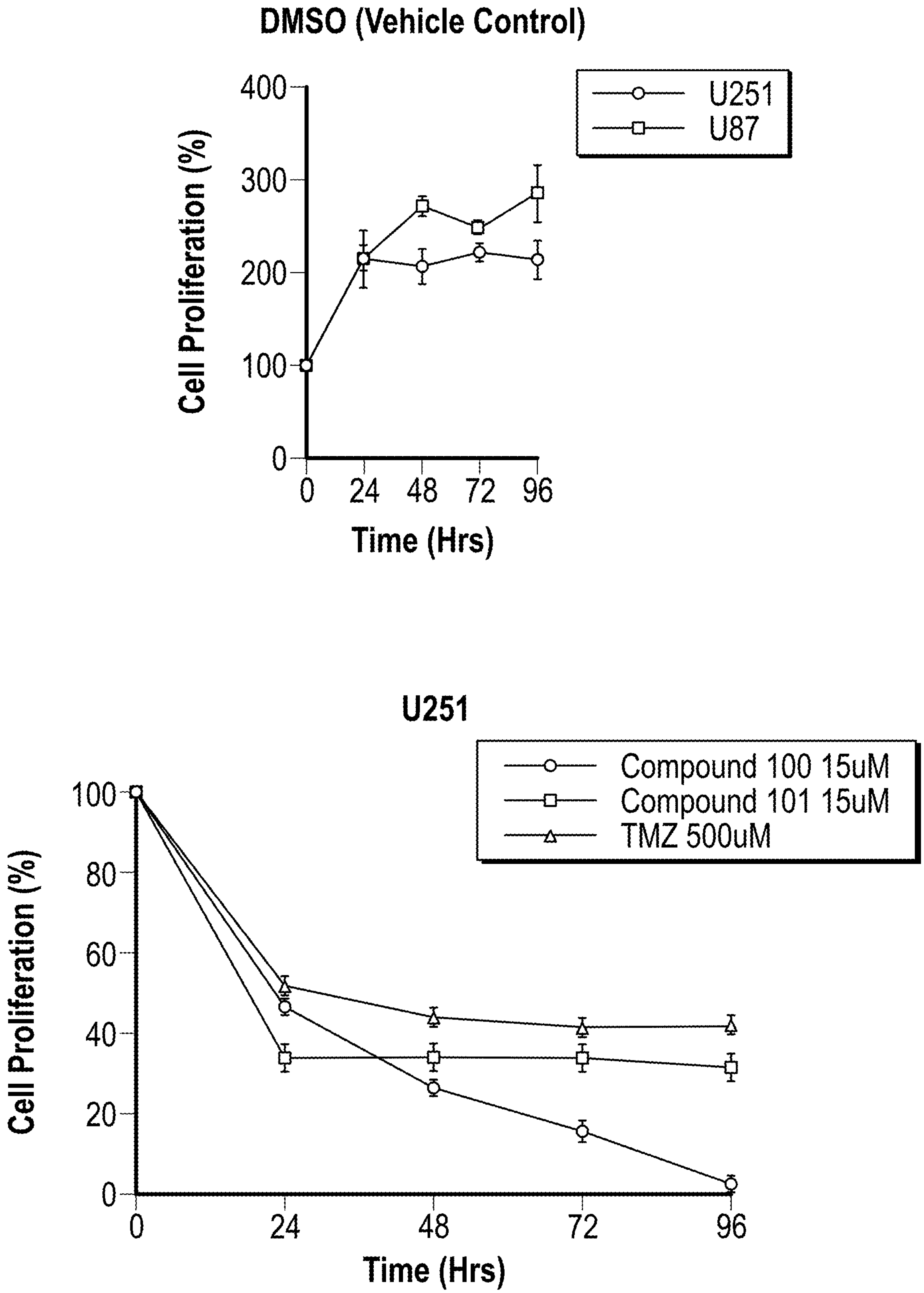
Figure 3B:
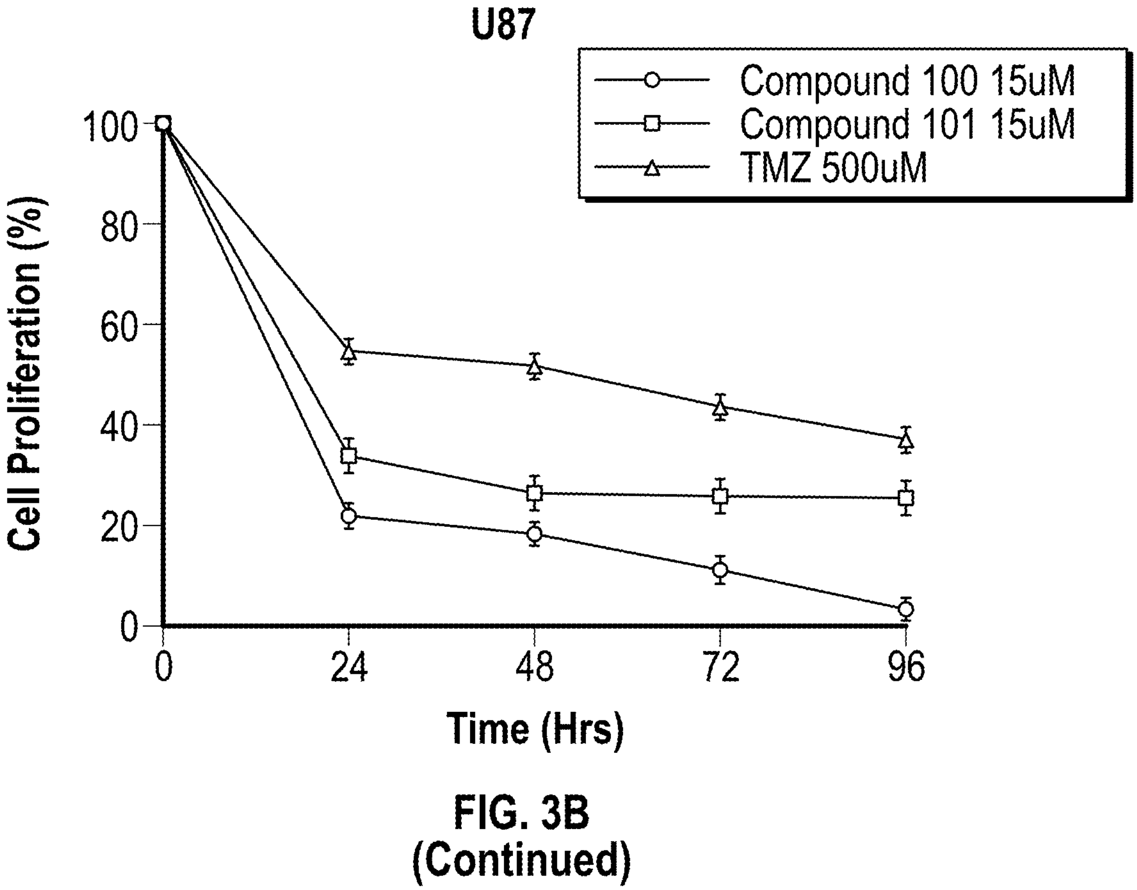

To determine the biological effect of Compound 100 and Compound 101, human glioblastoma-derived cell lines U251 and U87 were treated with varying concentrations of Compound 100, Compound 101, temazolomide (TMZ; a standard of care chemotherapeutic agent), or vehicle-toxicity control, dimethylsulfoxide (DMSO) used at final volumes that were identical to those used to attain all concentrations tested of Compound 100 and Compound 101. Remarkably, Compound 100 and Compound 101 demonstrated inhibition of glioma cell growth ($IC_{50}$) at a 50-fold lower concentration when compared to TMZ after 24 hours (FIG. 3A). Furthermore, when cell viability was assessed every 24 hours for 5 days, Compound 100 and Compound 101 reduced viability and the resulting proliferation of glioblastoma lines in a dose dependent manner compared to cells that were incubated with TMZ or DMSO (FIG. 3B). More importantly, cell viability of human neural stem cells as well as human astrocytes was not affected at the equivalent concentration, demonstrating that both Compound 100 and Compound 101 have glioma-specific cytotoxic activity. This was further confirmed by MTT cell viability assays wherein Compound 100 and Compound 101 treatment significantly reduced the growth of glioblastoma cell lines in a dose-dependent manner.

Figure 3C:
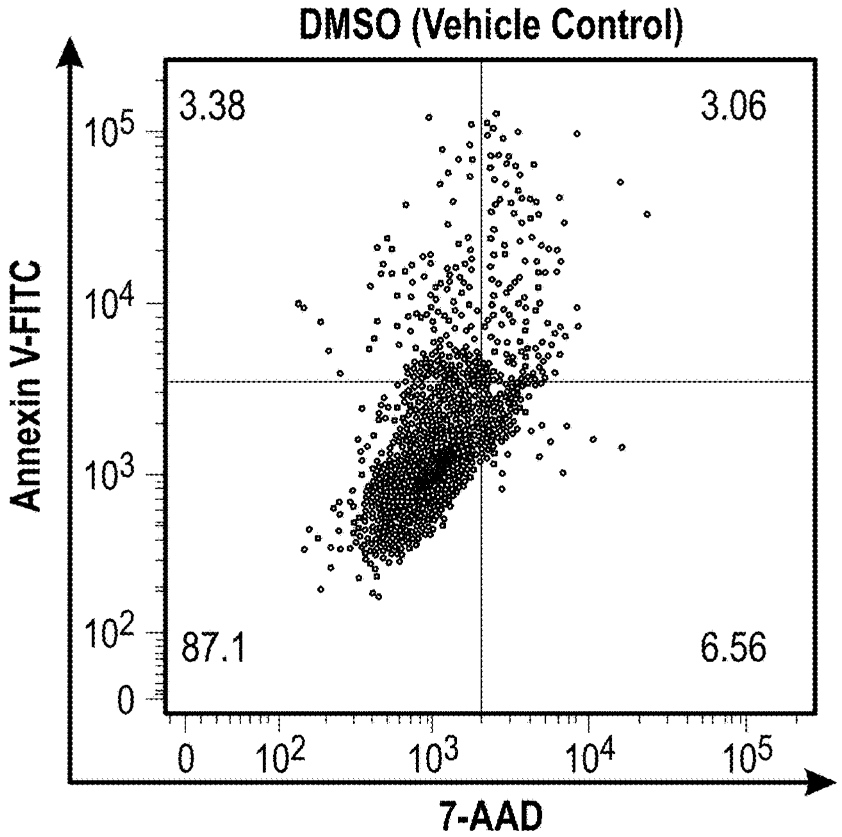
FIG. 3C is a flow cytometric analysis of U251 and U87 co-stained with Annexin V-FITC/7-AAD after treatment with Compound 100, Compound 101, TMZ, and vehicle control DMSO (n=4).
Figure 3C:
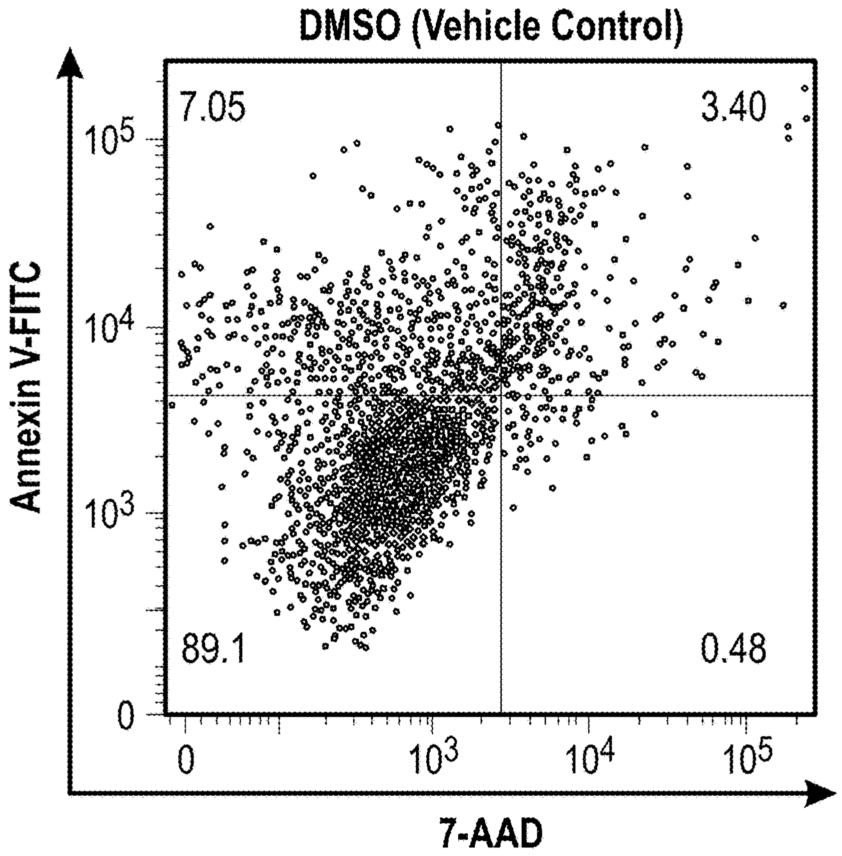
Figure 3C:
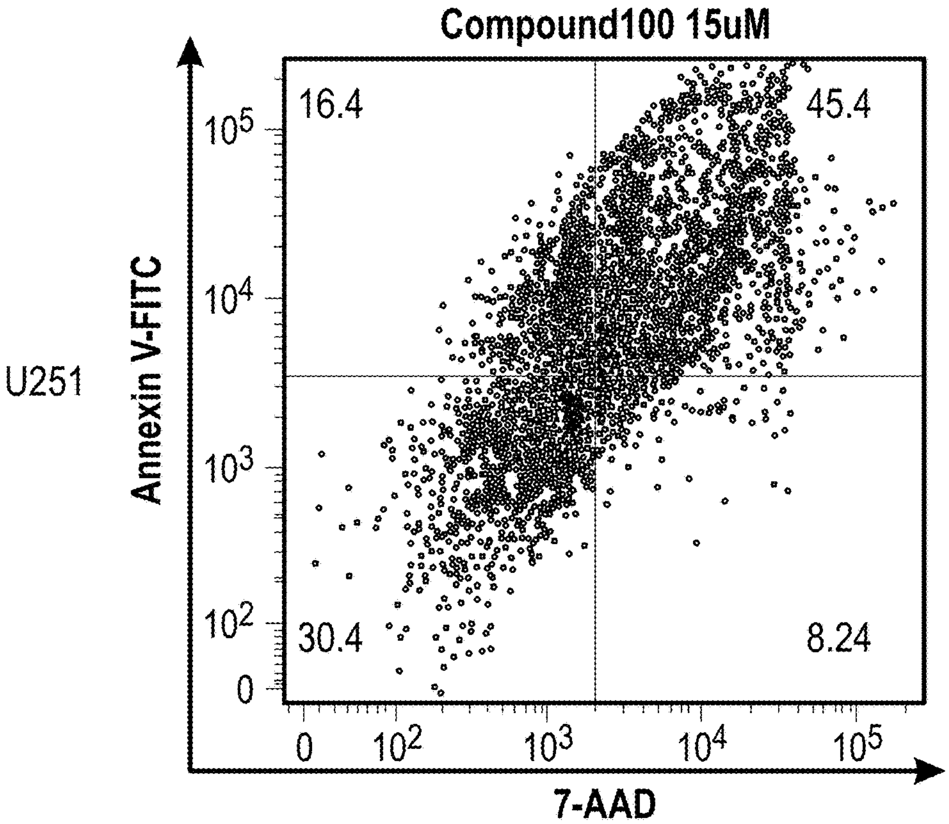
Figure 3C:
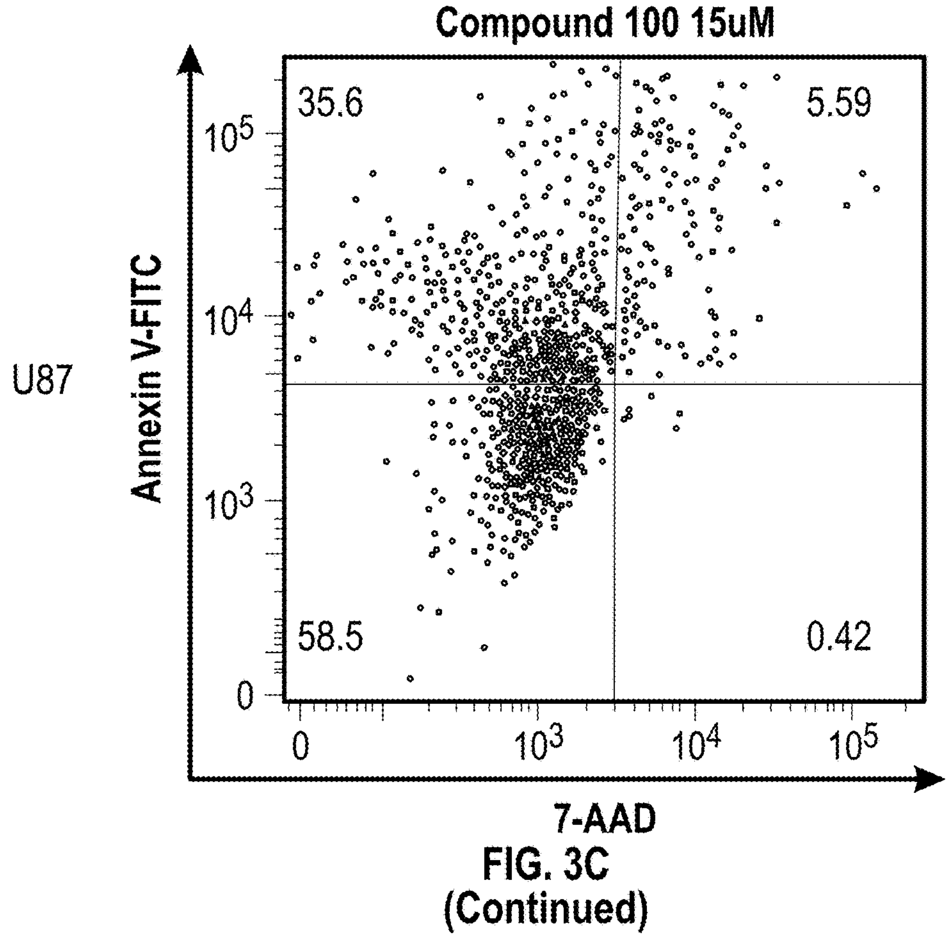
Figure 3C:
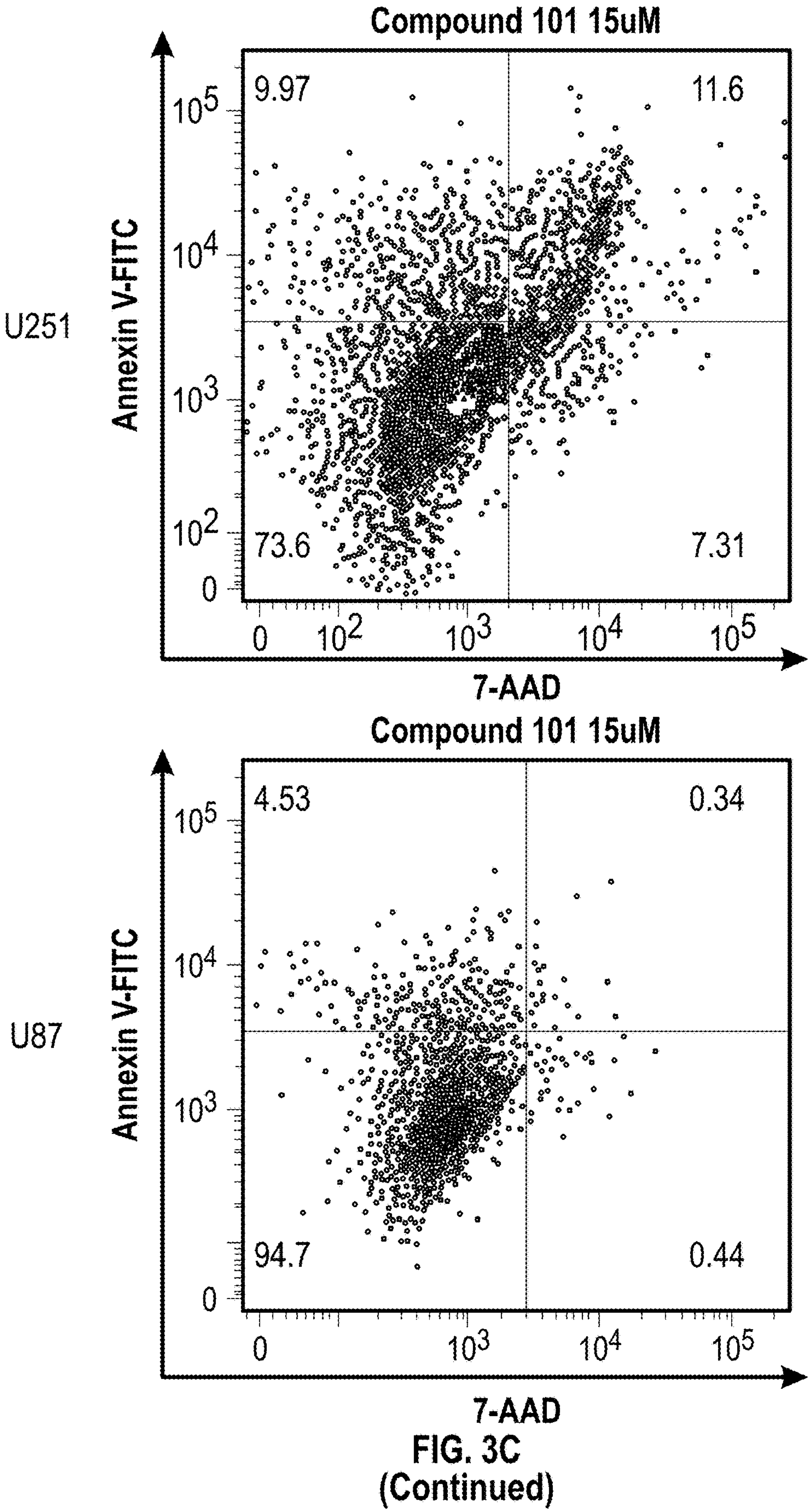
Figure 3C:
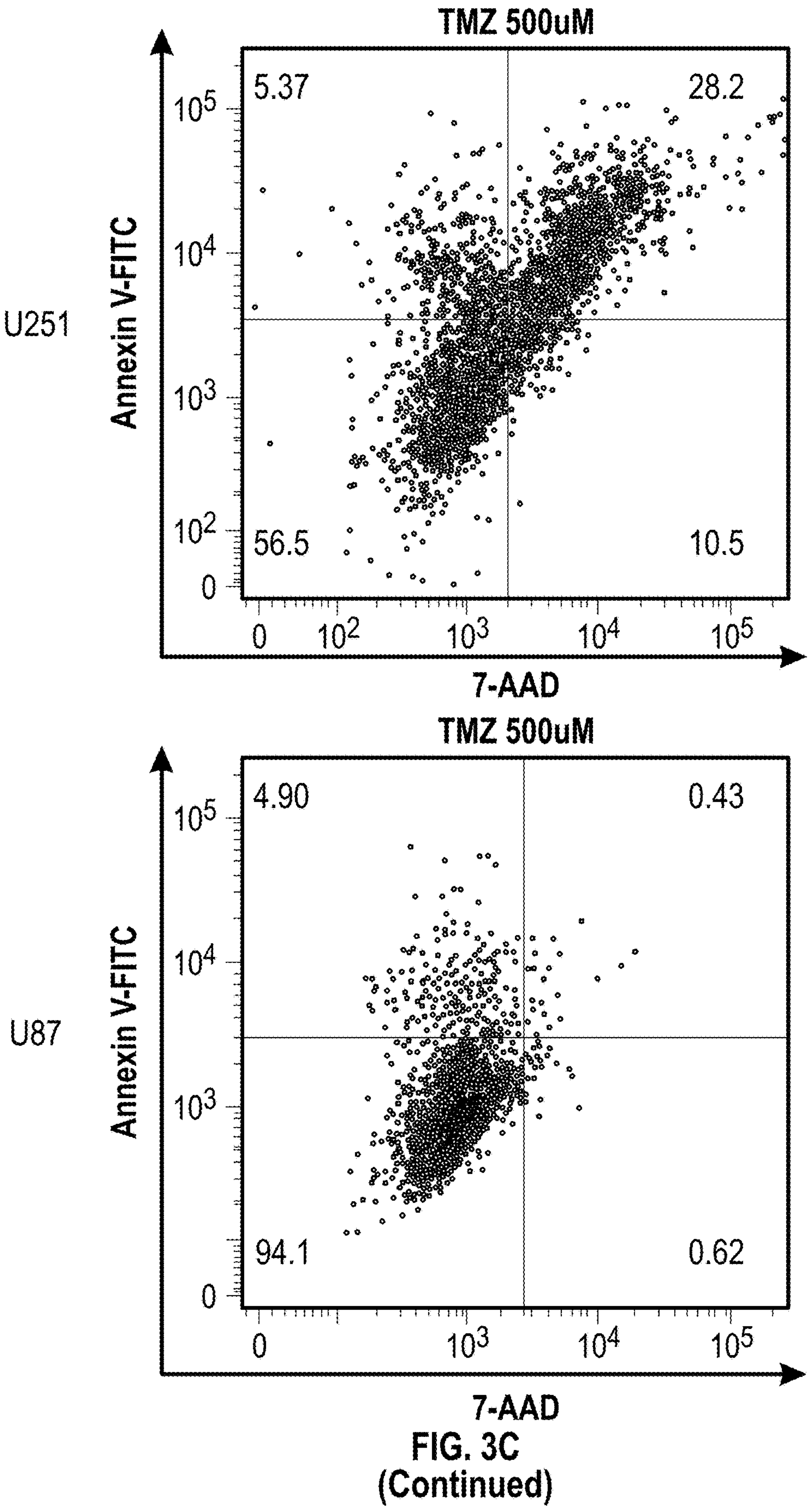
Figure 3D:
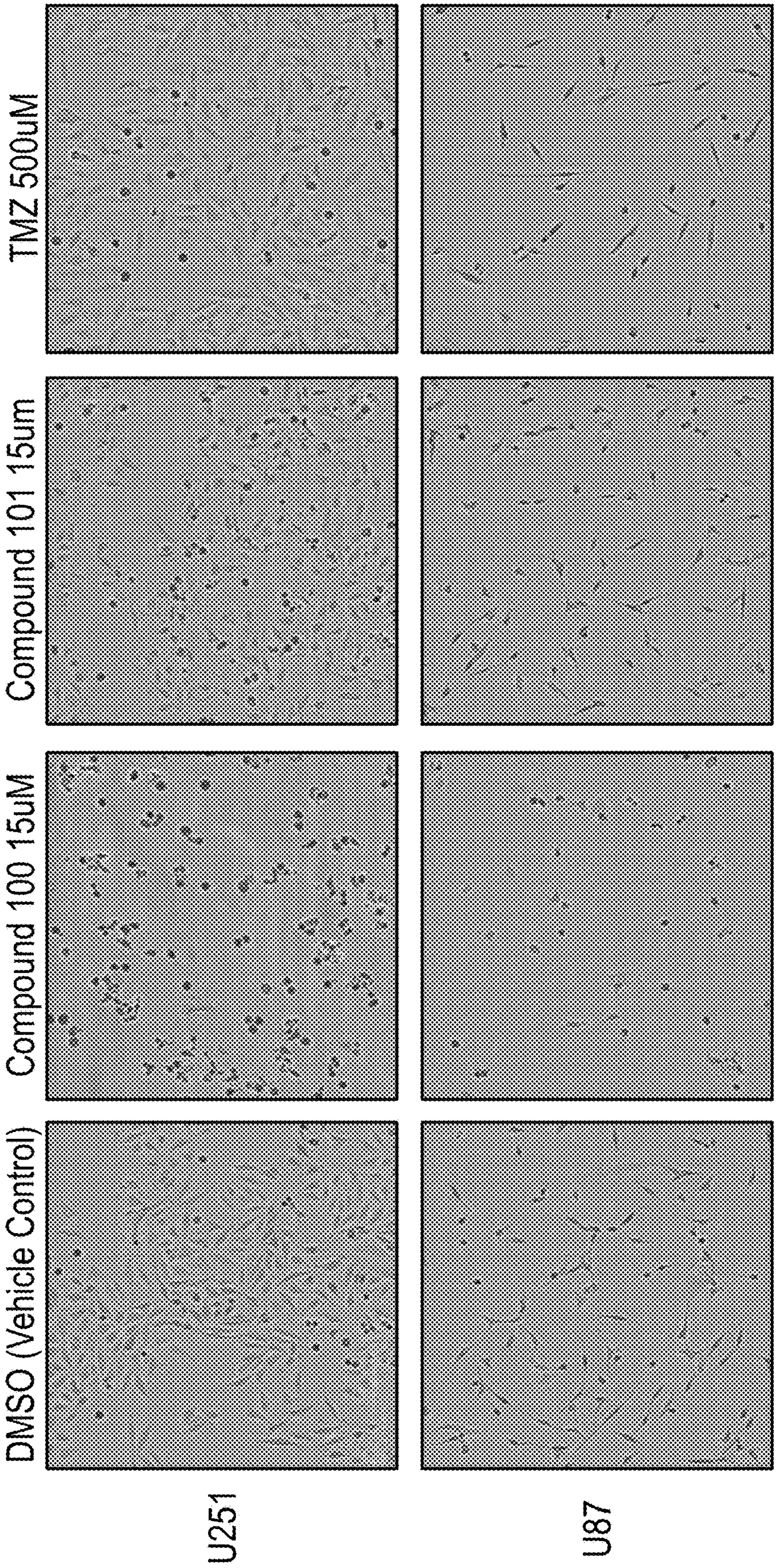
FIG. 3D depicts phase-contrast images using Incucyte for live cell tracking of U251 and U87 cells in response to treatment with Compound 100, Compound 101, TMZ, and vehicle control DMSO. Live cells were tracked and imaged for 96 hours (data not shown). Scale bar=300 μm. All data in FIG. 3A-3D are representative of four independent experiments and four replicates of each treatment condition were analyzed per experiment.

In order to elucidate the mechanism of this cell death, glioblastoma cells treated for 24 hours with Compound 100, Compound 101, TMZ, or DMSO control were analyzed for early and late apoptosis markers (Annexin V and 7-Amino-actinomycin D) by FACS analyses. These experiments revealed a 7-fold higher induction of apoptosis in U251 and U87 cells treated with Compound 100 or Compound 101 compared to cells treated with either TMZ or DMSO controls (FIG. 3C). Additionally, over a period of five days, morphological changes in U251 and U87 cells treated with Compound 100 and Compound 101 were tracked using the Incucyte live cell imaging system. Increased loss of adherence and cellular integrity were observed following treatment of U251 and U87 with Compound 100 and Compound 101, correlating with the decreased viability and increased cell death observed previously; similar behavior was not seen with human neural stem cells as well as human astrocytes (FIG. 3D).

Compound 100 and Compound 101 each demonstrated inhibition of glioma cell growth ($IC_{50}$) at a 50-fold lower concentration when compared to TMZ after 24 hours. Moreover, Compound 100 and Compound 101 each reduced viability and the resulting proliferation of glioblastoma lines in a dose dependent manner compared to cells that were incubated with TMZ or DMSO. Finally, cell viability of human neural stem cells as well as human astrocytes was not affected at the equivalent concentration, demonstrating that both Compound 100 and Compound 101 have glioma-specific cytotoxic activity.

Data presented herein show that Compound 100 and Compound 101 each reduce cell viability, decrease survival, and induce apoptosis selectively in glioblastoma cells. In comparison to 17β-estradiol, Compound 100 and Compound 101 have a unique profile for selective agonism of ERβ (FIG. 1). Furthermore, initial in vivo toxicity studies with Compound 100 and Compound 101 suggest that (i) neither compound is toxic and (ii) each compound reduces the growth of established tumors.

The data support the use of Compound 100 and Compound 101 as therapeutic agents against gliomas that are resistant to all currently available treatment modalities.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A method for treating a disease or condition selected from cancer, inflammation, neurodegeneration, spinal cord injury (SCI), multiple sclerosis (MS), Parkinson's disease (PD), or Alzheimer's disease (AD), the method comprising administering to a subject in need thereof a compound or salt thereof, wherein the compound has a structure corresponding to Formula (X-A1):

(X-A1)

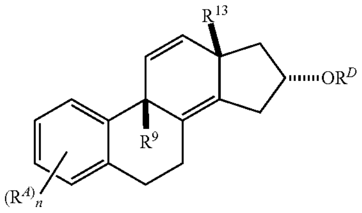

m is an integer selected from the group consisting of 1, 2, or 3;

n is an integer selected from the group consisting of 0, 1, 2, 3, and 4;

each $R^A$ is independently selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —S(O) $R^{Z1}$, —$NR^{Z1}R^{Z2}$, —$N(R^{Z1})$ C(O) $R^{Z2}$, —$N(R^{Z1})$ $S(O)_2R^{Z2}$, $C_{6-10}$-aryl, and 5- to 10-membered heteroaryl, wherein $R^{AX}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, —$S(O)_2NR^{Z1}R^{Z2}$, —$S(O)_2R^{21}$, $C_{6-10}$-aryl, or 5- to 10-membered heteroaryl, wherein $R^{AY}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, $C_{6-10}$-aryl, or 5- to 10-membered heteroaryl, wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy;

$R^9$ is selected from the group consisting of $C_{1-10}$-alkyl, $C_{2-10}$-alkenyl, $C_{2-10}$-alkynyl, $C_{1-10}$-haloalkyl, halogen, —$(CH_2)_m$—$C_{6-10}$-aryl, and —$(CH_2)_m$— 5- to 10-membered heteroaryl;

$R^{13}$ is selected from the group consisting of $C_{1-10}$-alkyl, $C_{2-10}$-alkenyl, $C_{2-10}$-alkynyl, $C_{1-10}$-haloalkyl, —$(CH_2)_m$—$C_{6-10}$-aryl, and —$(CH_2)_m$— 5- to 10-membered heteroaryl; and $R^D$ is selected from the group consisting of hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, $C_{6-10}$-aryl, and 5- to 10-membered heteroaryl;

wherein any $C_{6-10}$-aryl or 5- to 10-membered heteroaryl is optionally substituted with one or more halogen, hydroxy, $C_{1-6}$-alkyl, $C_{1-6}$-haloalkyl, or $C_{1-6}$-alkoxy.

2. The method of claim 1, wherein $R^A$ is —$OR^{AX}$ and $R^{AX}$ is hydrogen or $C_{1-6}$-alkyl.

3. The method of claim 1, wherein $R^9$ is $C_{1-6}$-alkyl, $C_{1-6}$-haloalkyl, —$(CH_2)_m$—$C_{6-10}$-aryl, or —$(CH_2)_m$— 5- to 10-membered heteroaryl.

4. The method of claim 1, wherein $R^{13}$ is $C_{1-6}$-alkyl or $C_{1-6}$-haloalkyl.

5. The method of claim 1, wherein $R^D$ is hydrogen, $C_{1-6}$-alkyl, or $C_{1-6}$-haloalkyl.

6. The method of claim 1, wherein n is 1, $R^A$ is —$OR^{AX}$, $R^{AX}$ is hydrogen or $C_{1-6}$-alkyl; $R^9$ is $C_{1-6}$-alkyl, $C_{1-6}$-haloalkyl, —$(CH_2)_m$—$C_{6-10}$-aryl, or —$(CH_2)_m$— 5- to 10-membered heteroaryl; $R^{13}$ is $C_{1-6}$-alkyl or $C_{1-6}$-haloalkyl; and $R^D$ is hydrogen, $C_{1-6}$-alkyl, or $C_{1-6}$-haloalkyl.

7. The method of claim 1, wherein the compound has a structure corresponding to:

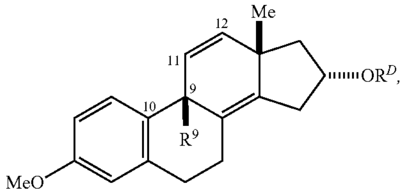

wherein $R^9$ is selected from the group consisting of $C_{1-10}$-alkyl, $C_{2-10}$-alkenyl, $C_{2-10}$-alkynyl, $C_{1-10}$-haloalkyl, halogen, —$(CH_2)_m$—$C_{6-10}$-aryl, and —$(CH_2)_m$— 5- to 10-membered heteroaryl; and $R^D$ is selected from the group consisting of hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, $C_{6-10}$-aryl, and 5- to 10-membered heteroaryl;

wherein any $C_{6-10}$-aryl or 5- to 10-membered heteroaryl is optionally substituted with one or more halogen, hydroxy, $C_{1-6}$-alkyl, $C_{1-6}$-haloalkyl, or $C_{1-6}$-alkoxy.

8. The method of claim 7, wherein $R^9$ is $C_{1-6}$-alkyl, $C_{1-6}$-haloalkyl, —$(CH_2)_m$—$C_{6-10}$-aryl, or —$(CH_2)_m$— 5- to 10-membered heteroaryl.

9. The method of claim 1, wherein the compound has a structure corresponding to:

Tetracyclic Product 6-1

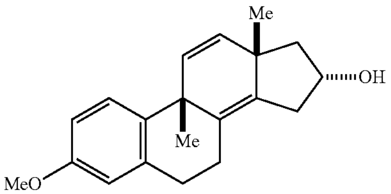

Tetracyclic Product 6-2

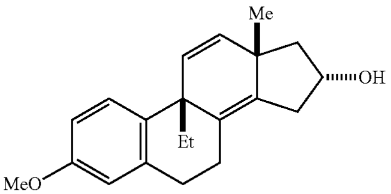

-continued

Tetracyclic Product 6-3

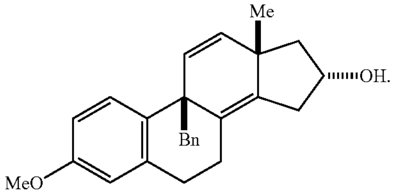

10. The method of claim 1, wherein the disease or condition is cancer and the cancer is breast cancer, prostate cancer, ovarian cancer, acute myeloid leukemia, or glioma.

11. The method of claim 1, wherein the disease or condition is inflammation.

12. The method of claim 1, wherein the disease or condition is neurodegeneration.

13. The method of claim 1, wherein the disease or condition is spinal cord injury (SCI).

14. The method of claim 1, wherein the disease or condition is multiple sclerosis (MS).

15. The method of claim 1, wherein the disease or condition is Parkinson's disease (PD).

16. The method of claim 1, wherein the disease or condition is Alzheimer's disease (AD).

* * * * *